US011602390B2

(12) United States Patent
Gogolin et al.

(10) Patent No.: US 11,602,390 B2
(45) Date of Patent: Mar. 14, 2023

(54) ELECTROSURGICAL APPARATUS WITH FLEXIBLE SHAFT

(71) Applicant: Apyx Medical Corporation, Clearwater, FL (US)

(72) Inventors: Gary G. Gogolin, Tampa, FL (US); Eric J. Hoegstrom, Dunedin, FL (US); Gregory Goliszek, Oldsmar, FL (US)

(73) Assignee: Apyx Medical Corporation, Clearwater, FL (US)

( * ) Notice: Subject to any disclaimer, the term of this patent is extended or adjusted under 35 U.S.C. 154(b) by 714 days.

(21) Appl. No.: 16/481,699

(22) PCT Filed: Jan. 30, 2018

(86) PCT No.: PCT/US2018/015948
§ 371 (c)(1),
(2) Date: Jul. 29, 2019

(87) PCT Pub. No.: WO2018/140944
PCT Pub. Date: Aug. 2, 2018

(65) Prior Publication Data
US 2019/0388135 A1 Dec. 26, 2019

Related U.S. Application Data

(60) Provisional application No. 62/468,496, filed on Mar. 8, 2017, provisional application No. 62/451,822, filed on Jan. 30, 2017.

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1477* (2013.01); *A61B 2017/00862* (2013.01);
(Continued)

(58) Field of Classification Search
CPC .............. A61B 18/042; A61B 18/1477; A61B 2018/00862; A61B 2018/00077;
(Continued)

(56) References Cited

U.S. PATENT DOCUMENTS

| 1,813,902 A | 7/1931 | Bovie |
| 2,435,442 A | 2/1948 | Gurewitsch |

(Continued)

FOREIGN PATENT DOCUMENTS

| CN | 110719759 A | 1/2020 |
| DE | 2429021 A1 | 1/1976 |

(Continued)

OTHER PUBLICATIONS

International Search Report and Written Opinion for PCT Application No. PCT/US2018/015948; dated Jun. 25, 2018; fourteen (14) pages.

(Continued)

*Primary Examiner* — Linda C Dvorak
*Assistant Examiner* — Annabeth E Rodriguez
(74) *Attorney, Agent, or Firm* — Gerald Hespos; Michael Porco

(57) ABSTRACT

An electrosurgical apparatus is provided including a housing, a flexible shaft, and a distal tip. The housing may further be coupled to an electrosurgical generator and gas supply. The distal tip of the electrosurgical apparatus may be grasped by a grasping tool, such that the orientation and position of the distal tip relative to the housing may be manipulated to achieve a plurality of positions. The electrosurgical apparatus provides electrosurgical energy and inert gas to an electrode within the distal tip of the electrosurgical apparatus to generate a plasma beam. In one aspect, the electrode is a retractable blade such that the electrosurgical apparatus can be used for mechanical and electrosur- (Continued)

gical cutting during surgery when the electrode is in an extended position and for cold plasma applications during surgery when the electrode is in a retracted position.

16 Claims, 57 Drawing Sheets

(51) Int. Cl.
*A61B 18/00* (2006.01)
*A61B 17/00* (2006.01)

(52) U.S. Cl.
CPC ............ *A61B 2017/00973* (2013.01); *A61B 2018/00077* (2013.01); *A61B 2018/00101* (2013.01); *A61B 2018/00583* (2013.01); *A61B 2018/00589* (2013.01); *A61B 2218/007* (2013.01)

(58) Field of Classification Search
CPC ........... A61B 2018/00101; A61B 2017/00973; A61B 2218/007
See application file for complete search history.

(56) References Cited

U.S. PATENT DOCUMENTS

| | | | |
|---|---|---|---|
| 3,239,730 A | 3/1966 | George | |
| 3,801,766 A | 4/1974 | Morrison | |
| 4,127,110 A | 11/1978 | Bullara | |
| 4,196,734 A | 4/1980 | Harris | |
| 4,545,375 A | 10/1985 | Cline | |
| 4,580,562 A | 4/1986 | Goof et al. | |
| 4,619,258 A | 10/1986 | Pool | |
| 4,625,723 A | 12/1986 | Altnether et al. | |
| 4,632,109 A | 12/1986 | Paterson | |
| 4,708,137 A | 11/1987 | Tsukagoshi | |
| 4,827,927 A | 5/1989 | Newton | |
| 4,884,557 A | 12/1989 | Takehana et al. | |
| 4,905,691 A | 3/1990 | Rydell | |
| 4,930,494 A | 6/1990 | Takehana et al. | |
| 5,088,997 A | 2/1992 | Delahuerga et al. | |
| 5,098,430 A | 3/1992 | Fleenor | |
| 5,207,675 A | 5/1993 | Canady | |
| 5,254,117 A * | 10/1993 | Rigby .................. | A61M 1/774 606/46 |
| 5,256,138 A | 10/1993 | Burek et al. | |
| 5,257,451 A | 11/1993 | Edwards et al. | |
| 5,269,780 A | 12/1993 | Roos | |
| 5,306,238 A | 4/1994 | Fleenor | |
| 5,400,267 A | 3/1995 | Denen et al. | |
| 5,403,342 A | 4/1995 | Tovey et al. | |
| 5,413,575 A * | 5/1995 | Haenggi ............ | A61B 18/1402 606/39 |
| 5,425,375 A | 6/1995 | Chin et al. | |
| 5,445,635 A | 8/1995 | Denen et al. | |
| 5,449,356 A | 9/1995 | Walbrink et al. | |
| 5,496,314 A | 3/1996 | Eggers | |
| 5,514,157 A | 5/1996 | Nicholas et al. | |
| 5,626,575 A | 5/1997 | Crenner | |
| 5,647,869 A | 7/1997 | Goble et al. | |
| 5,651,780 A | 7/1997 | Jackson et al. | |
| 5,660,657 A | 8/1997 | Rajala et al. | |
| 5,693,042 A | 12/1997 | Boiarski et al. | |
| 5,693,044 A | 12/1997 | Cosmescu | |
| 5,697,909 A | 12/1997 | Eggers et al. | |
| 5,720,745 A | 2/1998 | Farin et al. | |
| 5,743,880 A | 4/1998 | Hlavka | |
| 5,776,092 A | 7/1998 | Farin et al. | |
| 5,800,427 A | 9/1998 | Zamba | |
| 5,908,381 A | 6/1999 | Aznoian et al. | |
| 5,916,213 A | 6/1999 | Haissaguerre et al. | |
| 5,921,915 A | 7/1999 | Aznoian et al. | |
| 5,922,003 A | 7/1999 | Anctil et al. | |
| 6,017,340 A | 1/2000 | Cassidy et al. | |
| 6,063,081 A | 5/2000 | Mulier et al. | |
| 6,099,523 A | 8/2000 | Kim et al. | |
| 6,146,380 A | 11/2000 | Racz et al. | |
| 6,193,715 B1 | 2/2001 | Wrublewski et al. | |
| 6,225,593 B1 | 5/2001 | Howieson et al. | |
| 6,231,571 B1 | 5/2001 | Ellman et al. | |
| 6,293,945 B1 * | 9/2001 | Parins ................ | A61B 18/1402 606/45 |
| 6,293,960 B1 | 9/2001 | Ken | |
| 6,325,799 B1 | 12/2001 | Goble | |
| 6,391,027 B1 | 5/2002 | Farin et al. | |
| 6,409,724 B1 | 6/2002 | Penny et al. | |
| 6,451,016 B1 | 9/2002 | Karakozian | |
| 6,458,125 B1 | 10/2002 | Cosmescu | |
| 6,475,215 B1 | 11/2002 | Tanrisever | |
| 6,508,815 B1 | 1/2003 | Strul et al. | |
| 6,558,383 B2 | 5/2003 | Cunningham et al. | |
| 6,578,579 B2 | 6/2003 | Burnside et al. | |
| 6,652,514 B2 | 11/2003 | Ellman et al. | |
| 6,740,079 B1 | 5/2004 | Eggers et al. | |
| 6,743,239 B1 | 6/2004 | Kuehn et al. | |
| 6,770,071 B2 | 8/2004 | Woloszko et al. | |
| 6,852,112 B2 | 2/2005 | Platt | |
| 6,899,538 B2 | 5/2005 | Matoba | |
| 6,958,063 B1 | 10/2005 | Soll et al. | |
| 6,994,707 B2 | 2/2006 | Ellman et al. | |
| 7,033,353 B2 | 4/2006 | Stoddard et al. | |
| 7,070,596 B1 | 7/2006 | Woloszko et al. | |
| 7,115,121 B2 | 10/2006 | Novak | |
| 7,156,842 B2 | 1/2007 | Sartor et al. | |
| 7,156,844 B2 | 1/2007 | Reschke et al. | |
| 7,169,144 B2 | 1/2007 | Hoey et al. | |
| 7,244,257 B2 | 7/2007 | Podhajsky et al. | |
| 7,306,614 B2 | 12/2007 | Weller et al. | |
| 7,316,682 B2 | 1/2008 | Konesky | |
| 7,335,199 B2 | 2/2008 | Goble et al. | |
| 7,354,435 B2 | 4/2008 | Farin et al. | |
| 7,422,585 B1 | 9/2008 | Eggers et al. | |
| 7,443,296 B2 | 10/2008 | Mezhinsky et al. | |
| 7,479,140 B2 | 1/2009 | Ellman et al. | |
| 7,481,809 B2 | 1/2009 | Stern et al. | |
| 7,503,917 B2 | 3/2009 | Sartor et al. | |
| 7,568,619 B2 | 8/2009 | Todd et al. | |
| 7,578,817 B2 | 8/2009 | Canady | |
| 7,654,975 B2 | 2/2010 | Mantell | |
| 7,749,221 B2 | 7/2010 | Rontal | |
| 7,815,638 B2 | 10/2010 | Farin et al. | |
| 8,016,824 B2 | 9/2011 | Buchman et al. | |
| 8,022,327 B2 | 9/2011 | Blomeyer | |
| 8,096,943 B2 | 1/2012 | Melville | |
| 8,177,782 B2 | 5/2012 | Beller et al. | |
| 8,216,220 B2 | 7/2012 | Jensen et al. | |
| 8,319,134 B2 | 11/2012 | Blomeyer | |
| 8,328,804 B2 | 12/2012 | Heard et al. | |
| 8,337,521 B2 | 12/2012 | Cooper et al. | |
| 8,353,905 B2 | 1/2013 | Jensen et al. | |
| 8,562,598 B2 | 10/2013 | Falkenstein et al. | |
| 8,568,400 B2 | 10/2013 | Gilbert | |
| 8,579,802 B2 | 11/2013 | Robertson | |
| 8,689,606 B2 | 4/2014 | Schellekens et al. | |
| 8,998,899 B2 | 4/2015 | Shilev et al. | |
| 9,005,112 B2 | 4/2015 | Hasser et al. | |
| 9,060,750 B2 | 6/2015 | Lam | |
| 9,060,765 B2 | 6/2015 | Rencher et al. | |
| 9,095,333 B2 | 8/2015 | Konesky et al. | |
| 9,144,453 B2 | 9/2015 | Rencher et al. | |
| 9,326,810 B2 | 5/2016 | Shilev et al. | |
| 9,492,219 B2 | 11/2016 | Konesky et al. | |
| 9,763,724 B2 | 9/2017 | Konesky et al. | |
| 9,770,281 B2 | 9/2017 | Rencher et al. | |
| 9,770,285 B2 | 9/2017 | Zoran et al. | |
| 10,064,675 B2 | 9/2018 | Rencher et al. | |
| 10,441,369 B2 | 10/2019 | Shelton, IV et al. | |
| 11,272,973 B2 | 3/2022 | Gogolin | |
| 2001/0025177 A1 | 9/2001 | Woloszko | |
| 2002/0013582 A1 | 1/2002 | Mulier et al. | |
| 2003/0018318 A1 | 1/2003 | Melsky | |
| 2003/0018323 A1 | 1/2003 | Wallace et al. | |
| 2003/0050633 A1 | 3/2003 | Ellman et al. | |

(56) References Cited

U.S. PATENT DOCUMENTS

| | | |
|---|---|---|
| 2003/0130655 A1 | 7/2003 | Woloszko et al. |
| 2004/0148903 A1 | 8/2004 | Cash |
| 2004/0162553 A1* | 8/2004 | Peng ............... A61B 18/1402 606/42 |
| 2004/0181150 A1 | 9/2004 | Evans et al. |
| 2004/0243120 A1 | 12/2004 | Orszulak et al. |
| 2005/0075630 A1 | 4/2005 | Truckai et al. |
| 2005/0113820 A1 | 5/2005 | Goble et al. |
| 2005/0148903 A1 | 7/2005 | Diamantopoulos |
| 2005/0267459 A1 | 12/2005 | Belhe et al. |
| 2006/0036237 A1 | 2/2006 | Davison et al. |
| 2006/0095074 A1 | 5/2006 | Lee et al. |
| 2006/0122595 A1 | 6/2006 | Farin et al. |
| 2006/0161190 A1 | 7/2006 | Gadberry et al. |
| 2007/0010809 A1 | 1/2007 | Hovda et al. |
| 2007/0028669 A1 | 2/2007 | Brewster |
| 2007/0034211 A1* | 2/2007 | Hug ............... A61B 18/042 128/876 |
| 2007/0049922 A1 | 3/2007 | Rontal |
| 2007/0049926 A1 | 3/2007 | Sartor |
| 2007/0083247 A1 | 4/2007 | Wyeth et al. |
| 2007/0093810 A1 | 4/2007 | Sartor et al. |
| 2007/0135812 A1 | 6/2007 | Sartor |
| 2007/0158209 A1 | 7/2007 | Kang et al. |
| 2007/0260239 A1 | 11/2007 | Podhajsky et al. |
| 2007/0270797 A1 | 11/2007 | Lu et al. |
| 2007/0282303 A1 | 12/2007 | Nash et al. |
| 2007/0282358 A1 | 12/2007 | Remiszewski et al. |
| 2008/0071261 A1 | 3/2008 | Orszulak |
| 2008/0108985 A1 | 5/2008 | Konesky |
| 2008/0132893 A1 | 6/2008 | D'Amelio et al. |
| 2008/0140066 A1 | 6/2008 | Davison et al. |
| 2008/0300593 A1 | 12/2008 | Mulier et al. |
| 2009/0005772 A1 | 1/2009 | Penny |
| 2009/0062791 A1 | 3/2009 | Lee et al. |
| 2009/0125023 A1 | 5/2009 | Stephen et al. |
| 2009/0143778 A1 | 6/2009 | Sartor et al. |
| 2009/0149851 A1 | 6/2009 | Craig |
| 2009/0248022 A1 | 10/2009 | Falkenstein et al. |
| 2009/0253959 A1 | 10/2009 | Yoshie et al. |
| 2009/0270796 A1 | 10/2009 | Perry et al. |
| 2009/0306658 A1 | 12/2009 | Nobis et al. |
| 2010/0016856 A1 | 1/2010 | Platt, Jr. |
| 2010/0022824 A1* | 1/2010 | Cybulski ............... A61B 1/051 600/104 |
| 2010/0023008 A1 | 1/2010 | Heard et al. |
| 2010/0094288 A1 | 4/2010 | Kerr |
| 2010/0168827 A1 | 7/2010 | Schultz |
| 2010/0262139 A1 | 10/2010 | Beller et al. |
| 2011/0009856 A1 | 1/2011 | Jorgensen et al. |
| 2011/0118601 A1 | 5/2011 | Barnes et al. |
| 2011/0137115 A1 | 6/2011 | Suzuki |
| 2011/0238053 A1 | 9/2011 | Brannan et al. |
| 2011/0276113 A1 | 11/2011 | Cybulski |
| 2012/0046682 A1* | 2/2012 | Nelson ............... A61B 18/148 606/180 |
| 2012/0116397 A1* | 5/2012 | Rencher ............... A61B 18/042 606/45 |
| 2012/0123405 A1 | 5/2012 | Moua et al. |
| 2012/0197246 A1 | 8/2012 | Mauch |
| 2012/0232540 A1 | 9/2012 | Baur et al. |
| 2012/0303016 A1 | 11/2012 | Fischer et al. |
| 2012/0330305 A1 | 12/2012 | Zoran et al. |
| 2012/0330307 A1 | 12/2012 | Ladtkow et al. |
| 2013/0046290 A1 | 2/2013 | Palmer et al. |
| 2013/0218005 A1 | 8/2013 | Desai et al. |
| 2013/0237982 A1 | 9/2013 | Rencher et al. |
| 2013/0253498 A1 | 9/2013 | Germain et al. |
| 2013/0296846 A1 | 11/2013 | Canady et al. |
| 2014/0005665 A1 | 1/2014 | Konesky et al. |
| 2014/0018795 A1 | 1/2014 | Shilev et al. |
| 2014/0236144 A1 | 8/2014 | Krueger et al. |
| 2014/0257276 A1 | 9/2014 | Sartor |
| 2014/0276393 A1 | 9/2014 | Park et al. |
| 2015/0038790 A1 | 2/2015 | Rontal et al. |
| 2015/0073342 A1 | 3/2015 | Pacheco et al. |
| 2015/0088060 A1 | 3/2015 | Wang et al. |
| 2015/0209047 A1 | 7/2015 | Whitman |
| 2015/0216582 A1* | 8/2015 | Nagtegaal ............ A61B 18/042 604/23 |
| 2015/0238254 A1 | 8/2015 | Seddon et al. |
| 2015/0335388 A1 | 11/2015 | Iida et al. |
| 2015/0366602 A1* | 12/2015 | Rencher ............... A61B 18/042 606/45 |
| 2016/0022347 A1 | 1/2016 | Rencher et al. |
| 2016/0228171 A1* | 8/2016 | Boudreaux ............ A61B 18/00 |
| 2016/0331438 A1 | 11/2016 | Staneker et al. |
| 2017/0273733 A1 | 9/2017 | Weber |
| 2017/0312003 A1 | 11/2017 | Canady et al. |
| 2018/0014869 A1 | 1/2018 | Gogolin |
| 2018/0146925 A1 | 5/2018 | Mogul |
| 2019/0388135 A1 | 12/2019 | Gogolin et al. |
| 2020/0085491 A1 | 3/2020 | Goliszek et al. |

FOREIGN PATENT DOCUMENTS

| | | |
|---|---|---|
| DE | 9117111 | 11/1995 |
| DE | 102010061059 | 4/2012 |
| EP | 0186369 A1 | 7/1986 |
| EP | 0878263 A1 | 11/1998 |
| EP | 1764057 A1 | 3/2007 |
| EP | 1764057 B1 | 4/2009 |
| EP | 2263728 A2 | 12/2010 |
| EP | 2449992 A1 | 5/2012 |
| JP | 2007068596 A | 3/2007 |
| WO | 03001986 A2 | 1/2003 |
| WO | 2003082134 A1 | 10/2003 |
| WO | 2004096315 A2 | 11/2004 |
| WO | 2004096315 A3 | 7/2006 |
| WO | 2014031800 A1 | 2/2014 |
| WO | 2018222562 A1 | 12/2018 |

OTHER PUBLICATIONS

EP Search Report and Written Opinion for EP Application No. 18 74 4923.6; dated Jul. 30, 2020; four (4) pages.

* cited by examiner

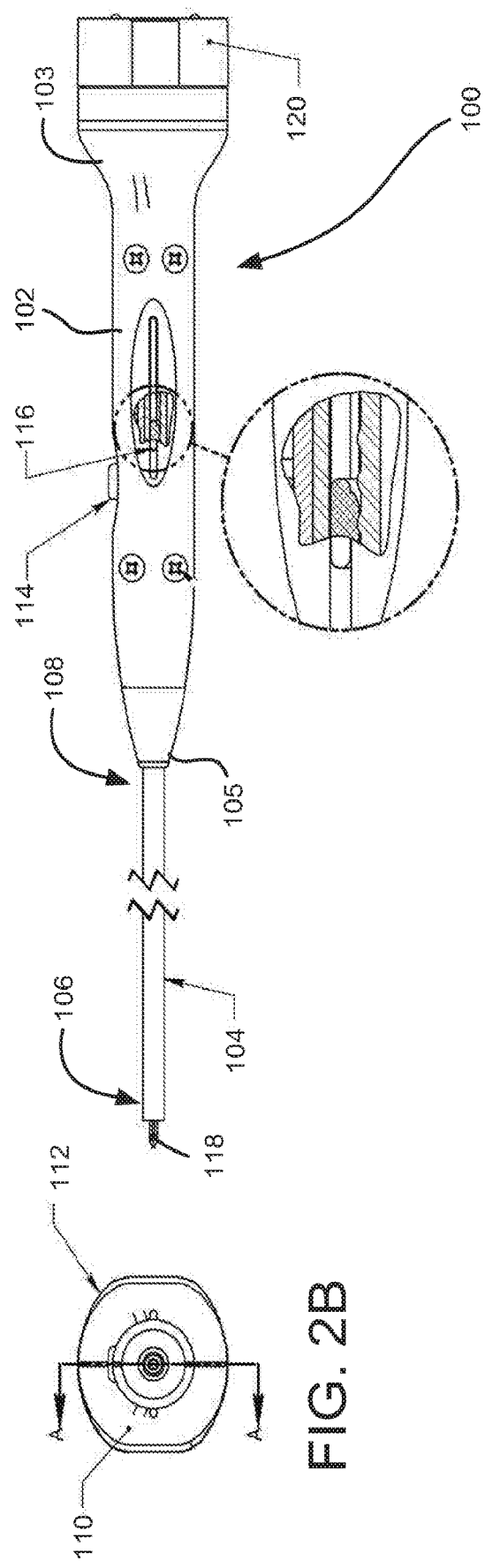

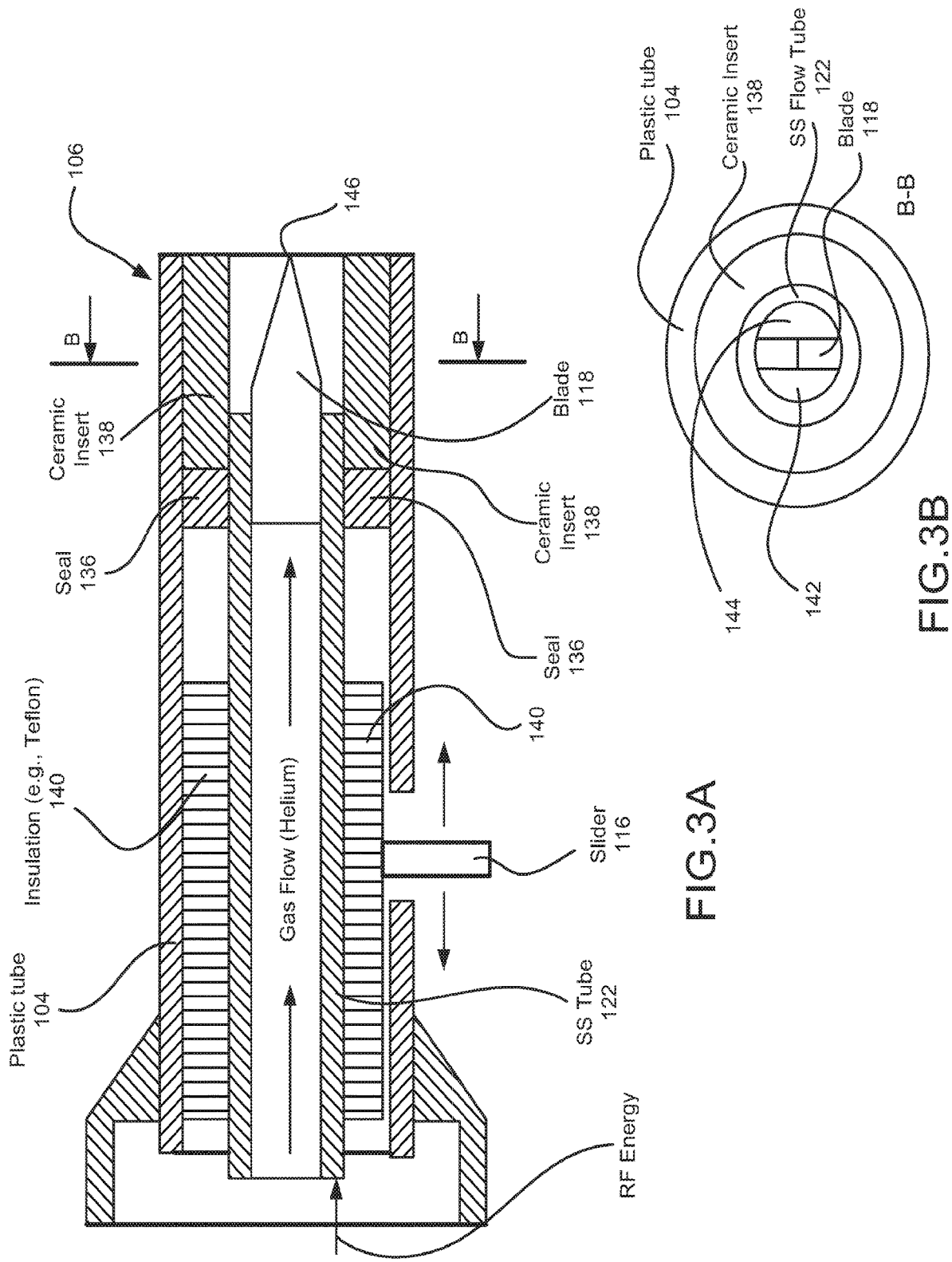

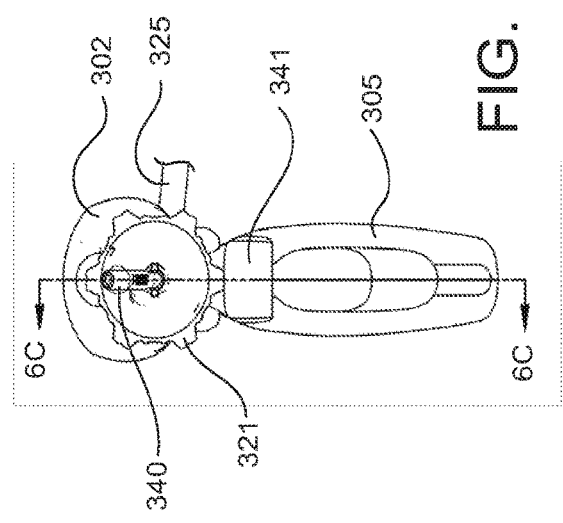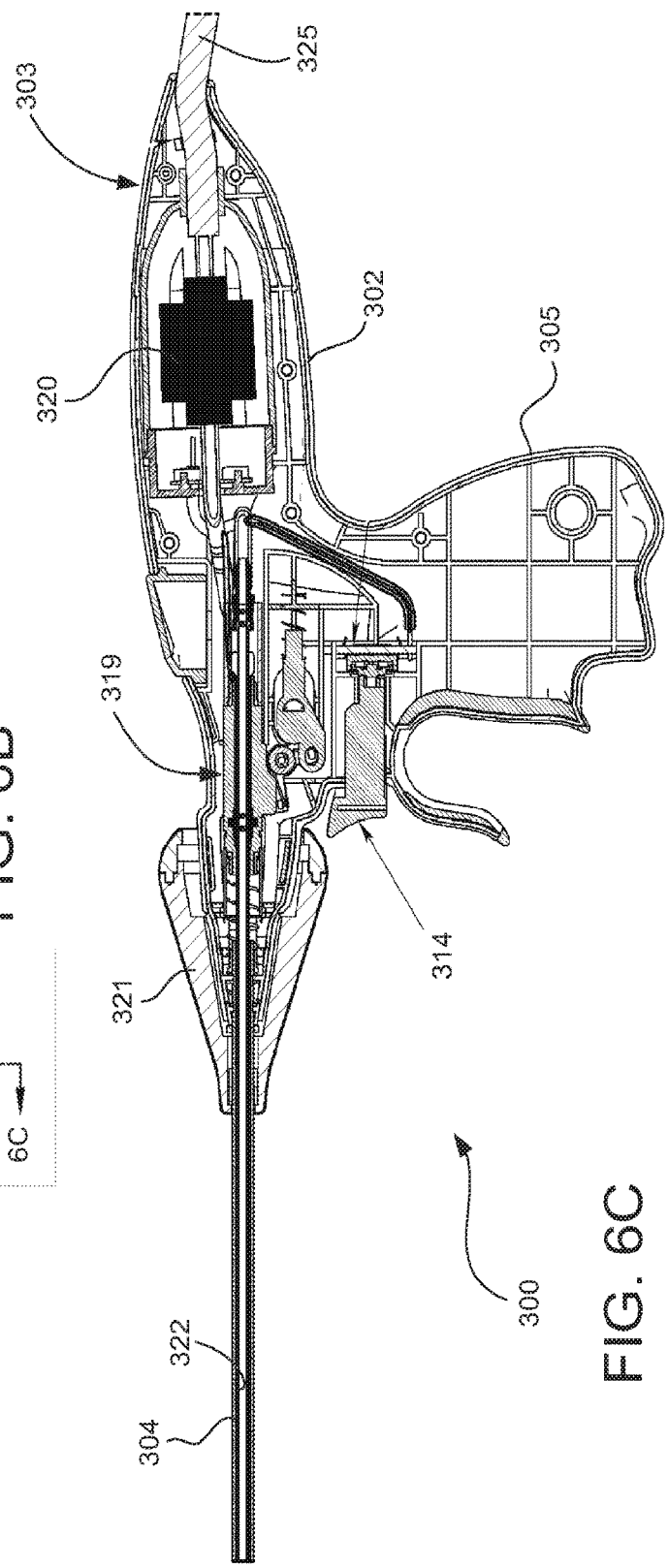

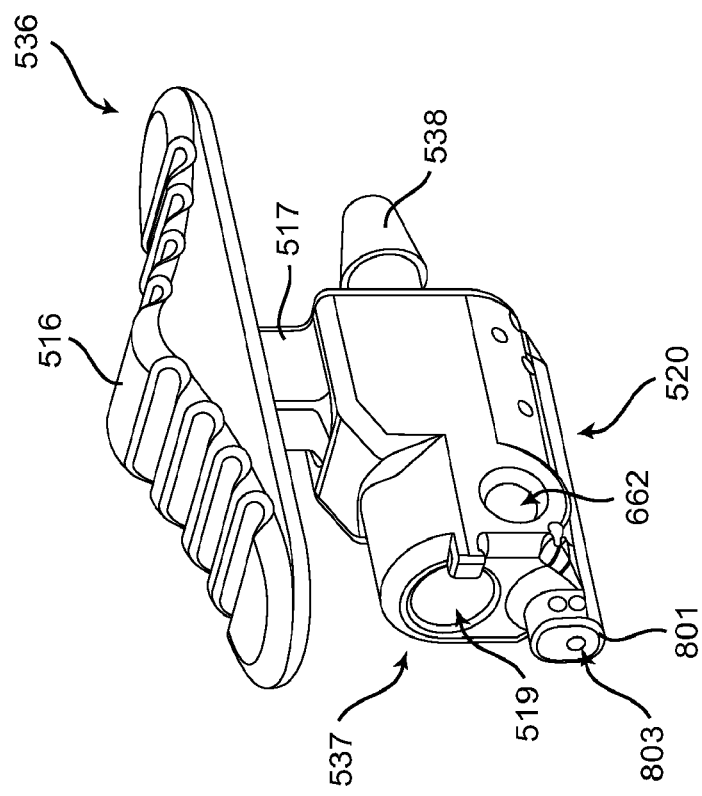
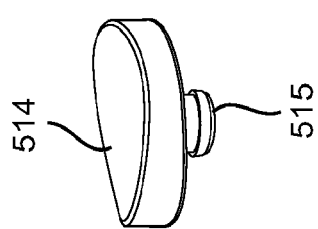
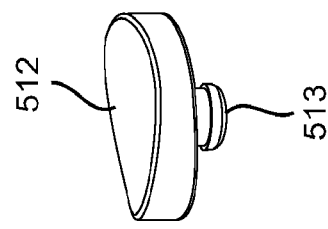
FIG. 12C

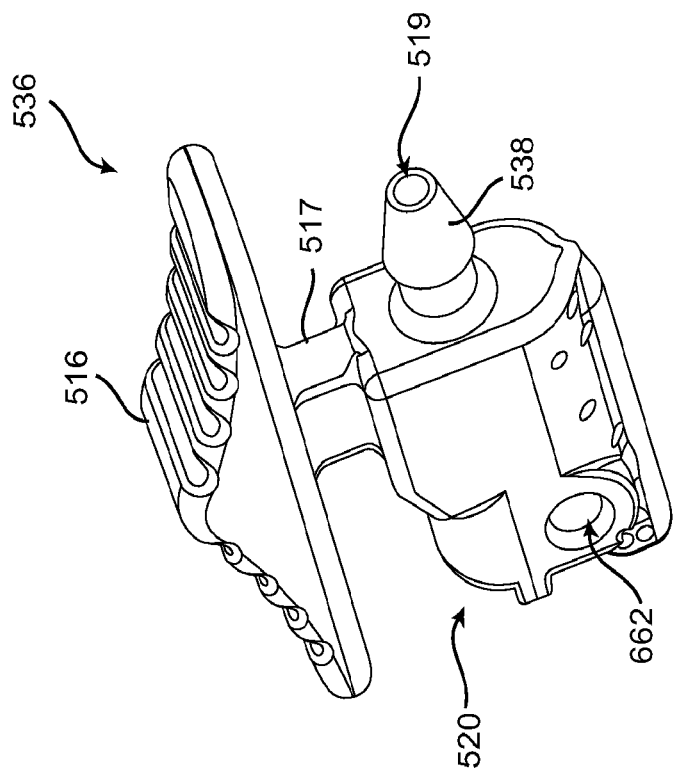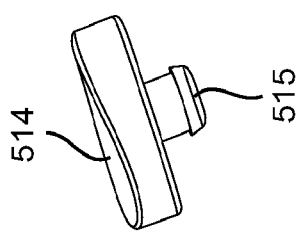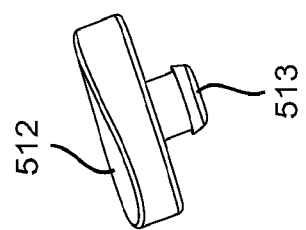
FIG. 12D

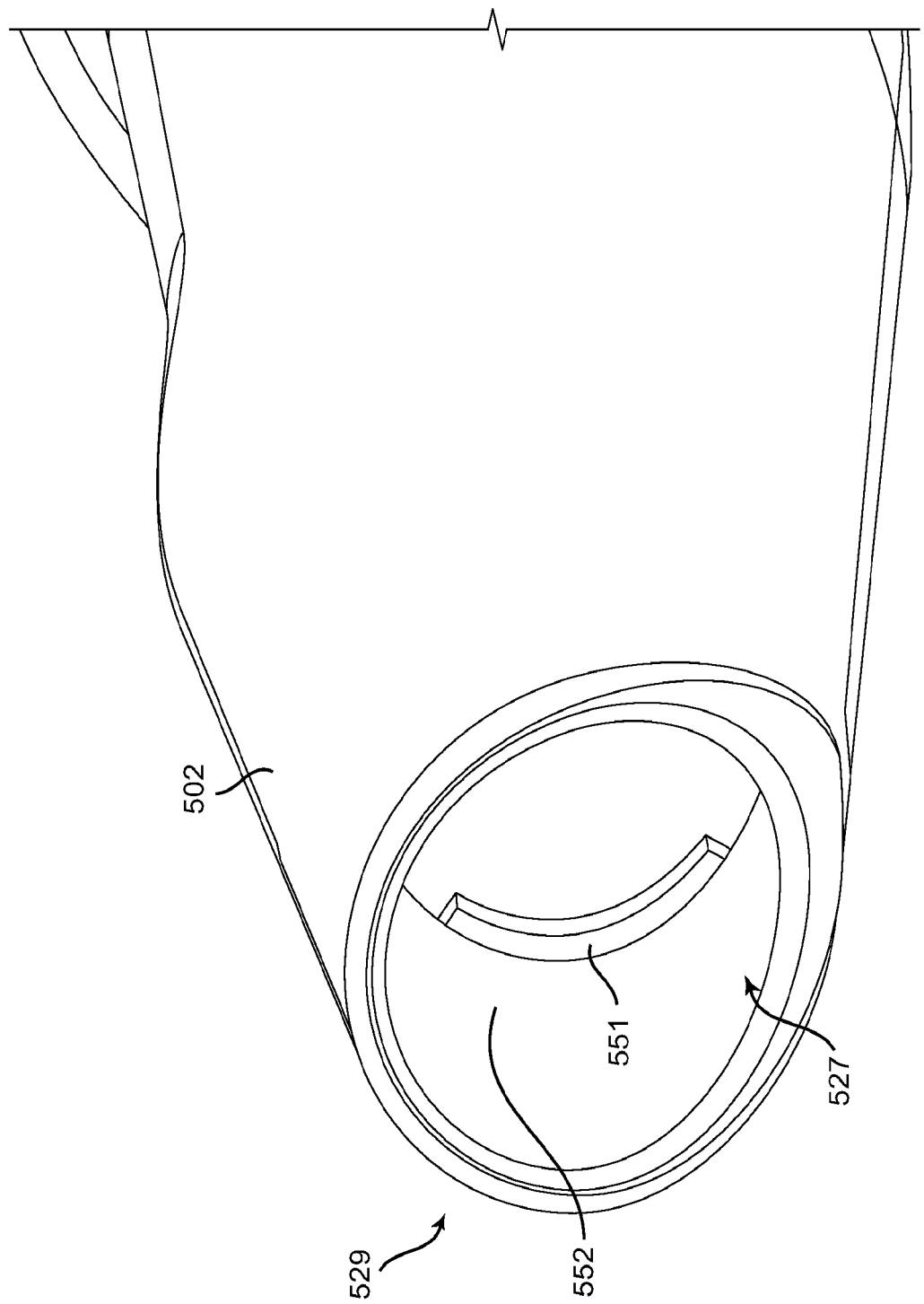

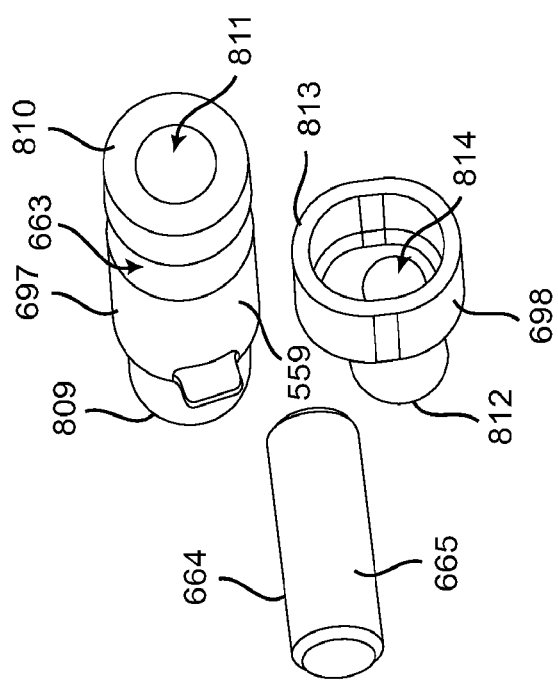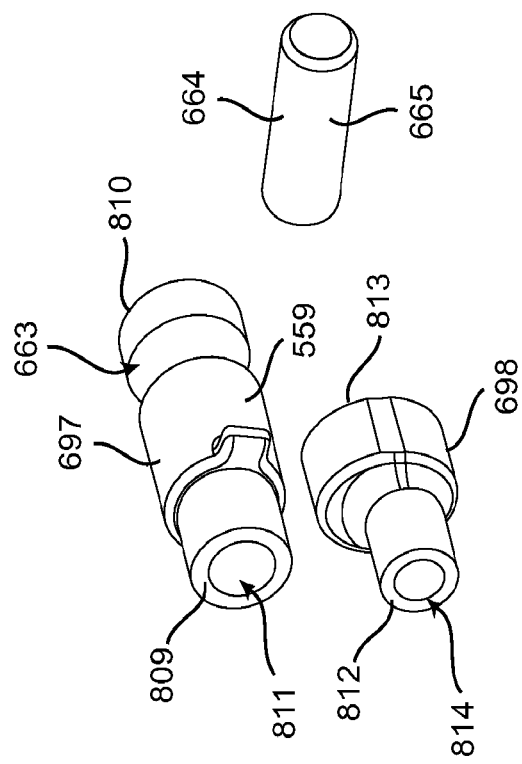
FIG. 13H

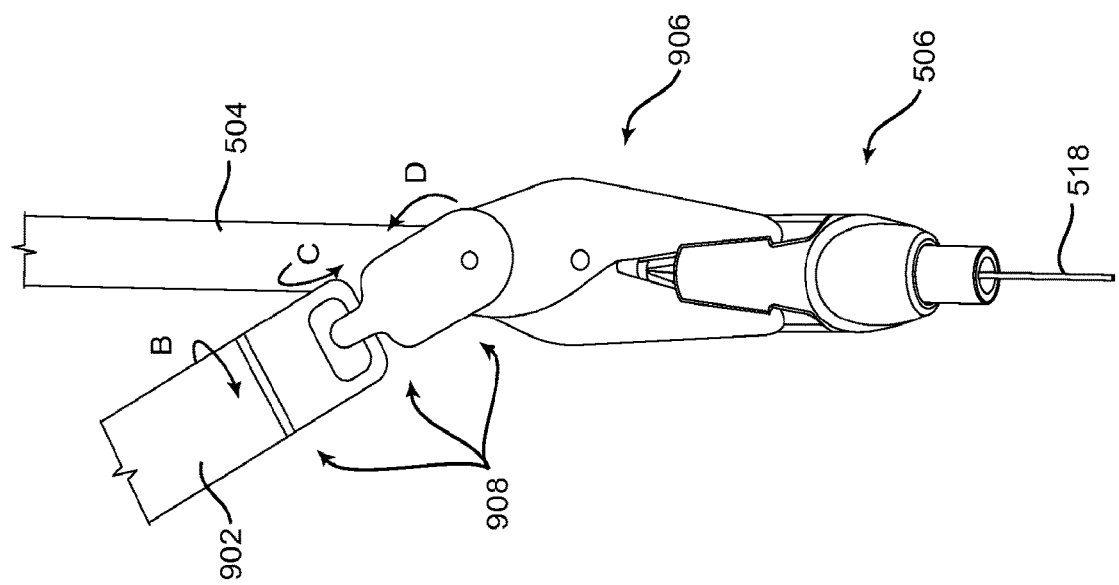

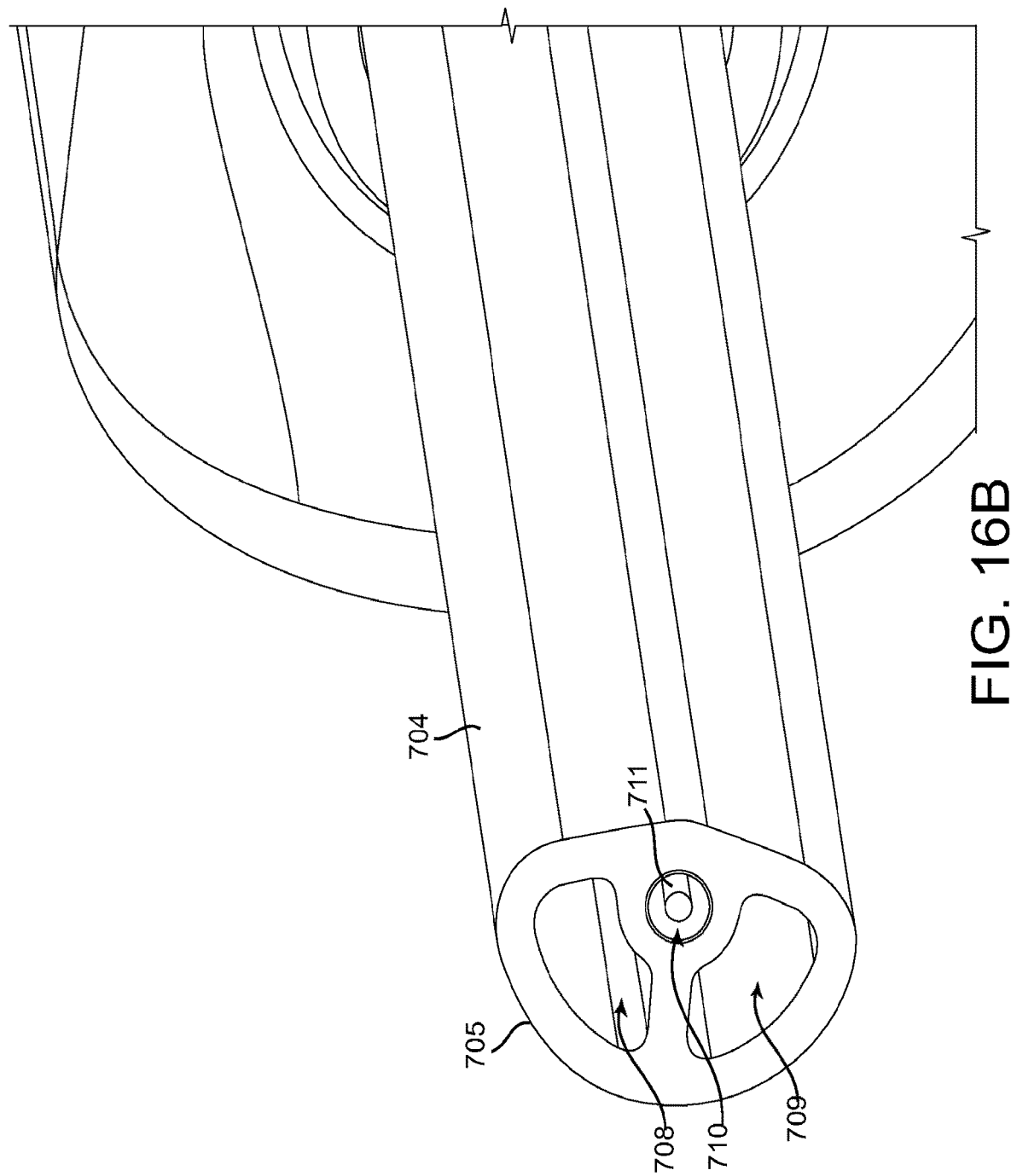

ELECTROSURGICAL APPARATUS WITH FLEXIBLE SHAFT

PRIORITY

This application claims priority to U.S. Provisional Patent Application No. 62/451,822, filed Jan. 30, 2017, entitled "ELECTROSURGICAL APPARATUS WITH FLEXIBLE SHAFT", the contents of which are hereby incorporated by reference in its entirety. This application also claims priority to U.S. Provisional Patent Application No. 62/468,496, filed Mar. 8, 2017, entitled "ELECTROSURGICAL APPARATUS WITH FLEXIBLE SHAFT", the content of which are hereby incorporated by reference in its entirety.

BACKGROUND

Field

The present disclosure relates generally to electrosurgery and electrosurgical systems and apparatuses, and more particularly, to an electrosurgical apparatus with a flexible shaft and a retractable electrode, e.g., an electrosurgical blade, needle, etc., for use in cold plasma applications, electrosurgical cutting and mechanical cutting.

Description of the Related Art

High frequency electrical energy has been widely used in surgery and is commonly referred to as electrosurgical energy. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures. In the latter case, it is often desirable to be able to redirect the position of the cold plasma beam tip to a specific operative site. The external incision and pathway for the endoscopic tool may be chosen to avoid major blood vessels and non-target organs, and may not coincide with an optimum alignment for the target internal tissue site. A means of redirecting the cold plasma beam is essential in these situations.

Elaborate mechanisms have been developed to change the direction of the plasma beam by the surgeon as needed. However, these mechanisms are mechanically complicated, expensive to produce and, in some cases, unwieldy to operate effectively. The small diameter of the endoscopic trocar through which this surgical tool must be inserted places even more severe restrictions on these issues.

SUMMARY

In one aspect of the present disclosure, an electrosurgical apparatus is provided. The electrosurgical apparatus of the present disclosure includes a housing, a flexible shaft, and a distal tip. The housing may further be coupled to an electrosurgical generator and gas supply. The distal tip of the electrosurgical apparatus may be configured to be grasped by a grasping tool, such as forceps, such that, the orientation of the distal tip of the electrosurgical apparatus may be manipulated about the flexible shaft in a plurality of ways. The electrosurgical apparatus is configured to provide electrosurgical energy and inert gas to an electrode within the distal tip of the electrosurgical apparatus to generate a plasma beam.

In one aspect, the electrode is configured as a retractable blade, such that the electrosurgical apparatus is configured for use in mechanical and electrosurgical cutting during surgery when the electrode is in an extended position and for cold plasma applications during surgery when the electrode is in a retracted position.

In another aspect of the present disclosure, an electrosurgical apparatus is provided including: a housing including a proximal end and a distal end; a flexible insulating outer tube including a proximal end and a distal end, the proximal end of the flexible insulating outer tube coupled to the distal end of the housing; a distal tip including a proximal end and a distal end, the proximal end of the distal tip coupled to the distal end of the flexible insulating outer tube, the distal tip including an electrode; and a flexible electrically conducting member disposed through the flexible insulating outer tube and including a proximal end and a distal end, the distal end of the flexible electrically conducting member coupled to the electrode and configured to provide electrosurgical energy thereto; wherein the flexible insulating outer tube and the flexible electrically conducting member are configured to enable the distal tip to achieve a plurality of positions relative to the housing.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram showing a side view of an electrosurgical apparatus in accordance with an embodiment of the present disclosure;

FIG. 2B is a front view of the electrosurgical apparatus shown in FIG. 2A:

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

FIG. 6B is a front view of the electrosurgical apparatus shown in FIG. 6A;

FIG. 6C is a cross sectional view of the electrosurgical apparatus shown in FIG. 6B taken along line 6C-6C;

FIG. 10A illustrates a distal end of the electrosurgical apparatus before insertion into a trocar, FIG. 10B illustrates the distal end of the electrosurgical apparatus passing through the trocar, and FIG. 10C illustrates the distal end of the applicator emerging from the distal end of the trocar when fully inserted;

FIGS. 12C and 12D are perspective views of a slider and two buttons of the apparatus of FIG. 11A in accordance with the present disclosure;

FIG. 12G is a partial perspective view of a distal end of the housing of FIG. 12A in accordance with an embodiment of the present disclosure;

FIG. 13H includes perspective views of several components of the electrosurgical apparatus of FIG. 11A in accordance with the present disclosure;

FIG. 14H is a partial perspective view of a distal portion of electrosurgical apparatus of FIG. 11A coupled to the forceps of FIG. 11B in accordance with the present disclosure;

FIG. 16B is a partial perspective view of a distal end of a multi-lumen shaft of the electrosurgical apparatus of FIG. 16A in accordance with the present disclosure;

Figure 1:
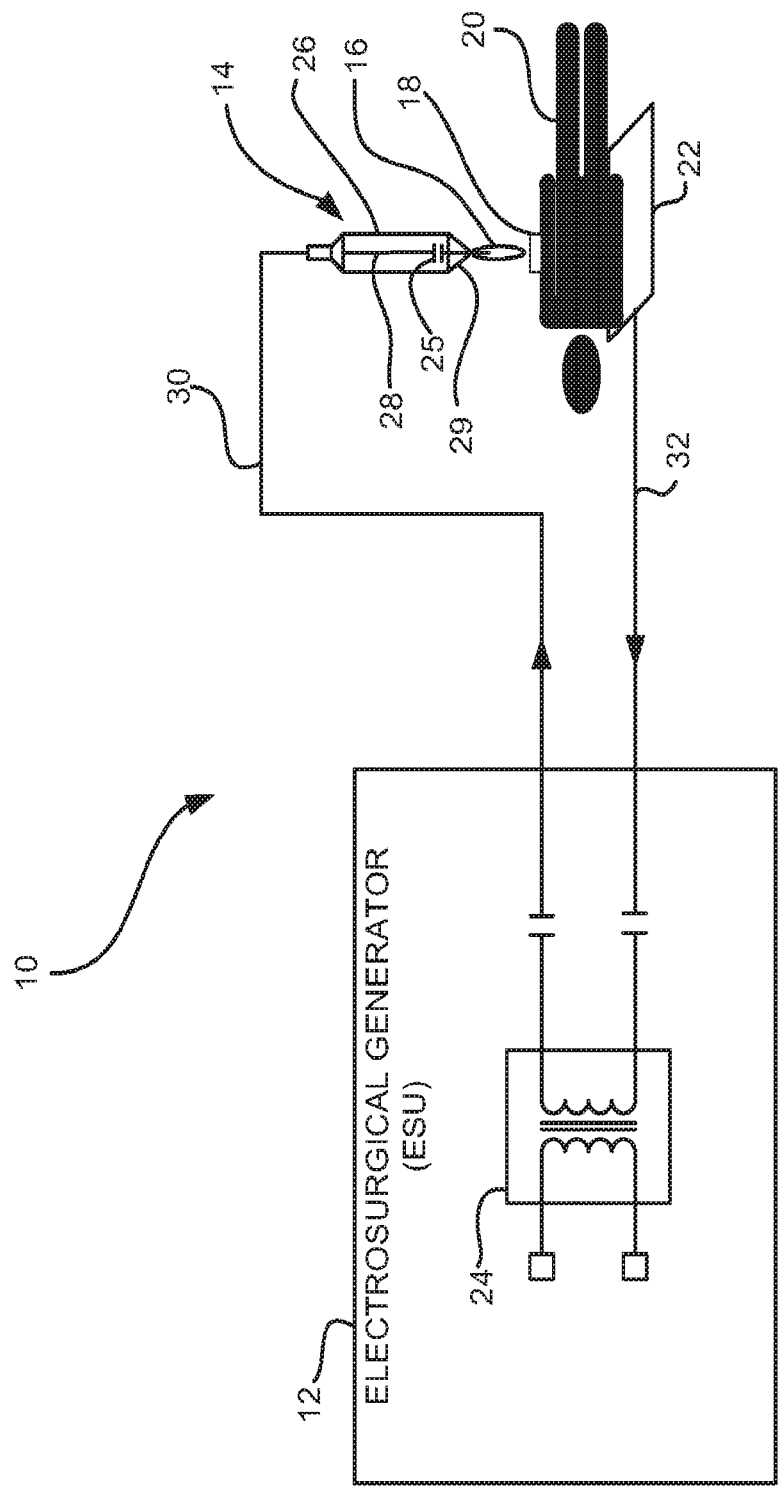
FIG. 1 is an illustration of an exemplary monopolar electrosurgical system in accordance with an embodiment of the present disclosure.

It should be understood that the drawings are for purposes of illustrating the concepts of the disclosure and are not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, in some embodiments, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece 26, e.g., a step-down transformer, a step-up transformer or any combination thereof.

Figure 2C:
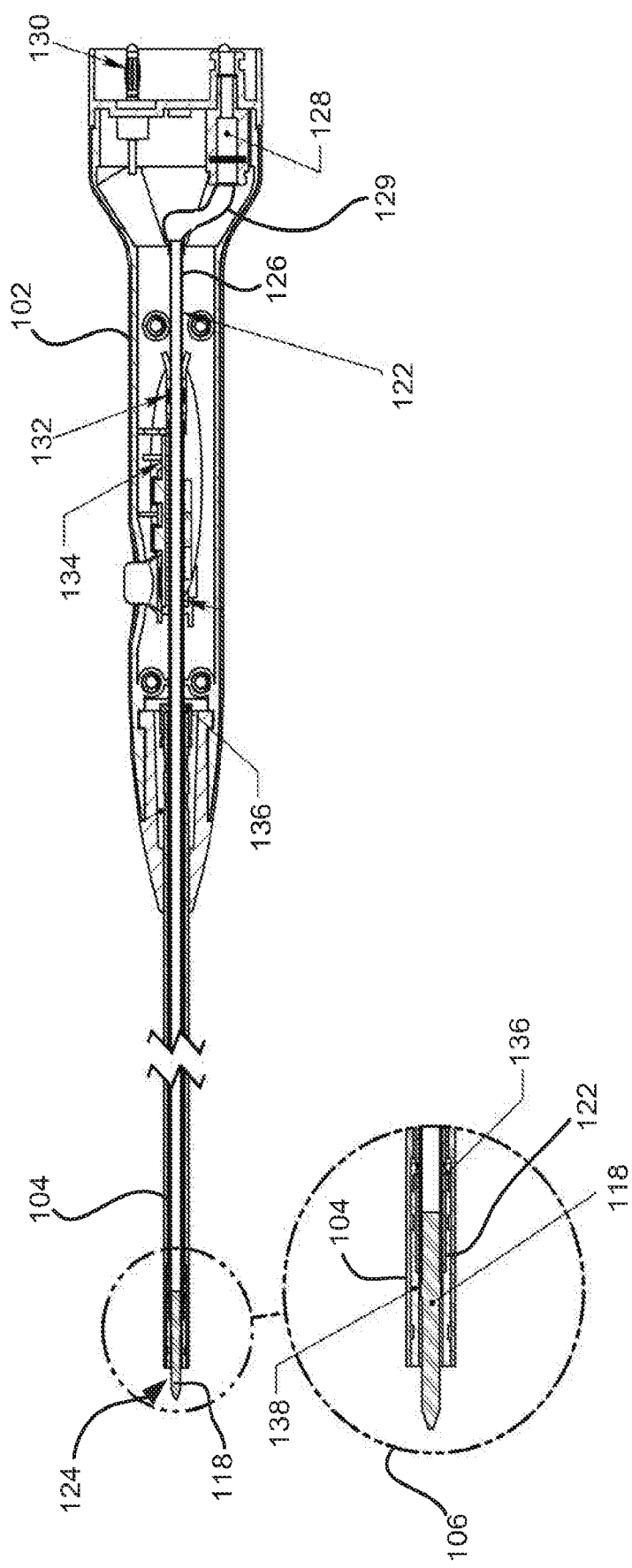
FIG. 2C is a cross sectional view of the electrosurgical apparatus shown in FIG. 2A taken along line A-A.

Referring to FIGS. 2A-2C, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 may be provided on the proximal end 103 of the housing 102 for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, in some embodiments, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2C. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran™. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2C. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen In FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end of the outer tube 104.

When the blade is in the retracted position as shown in FIG. 3A, the apparatus 102 is suitable for generating plasma. In the retracted position, RF energy is conducted to a tip 146 of the blade 118 from an electrosurgical generator (not shown) via the flow tube 122. An inert gas, such as helium or argon, is then supplied through the flow tube 122 from either the electrosurgical generator or an external gas source. As the inert gas flows over the sharp point 146 of the blade 118 held at high voltage and high frequency, a cold plasma beam is generated.

Figure 4:
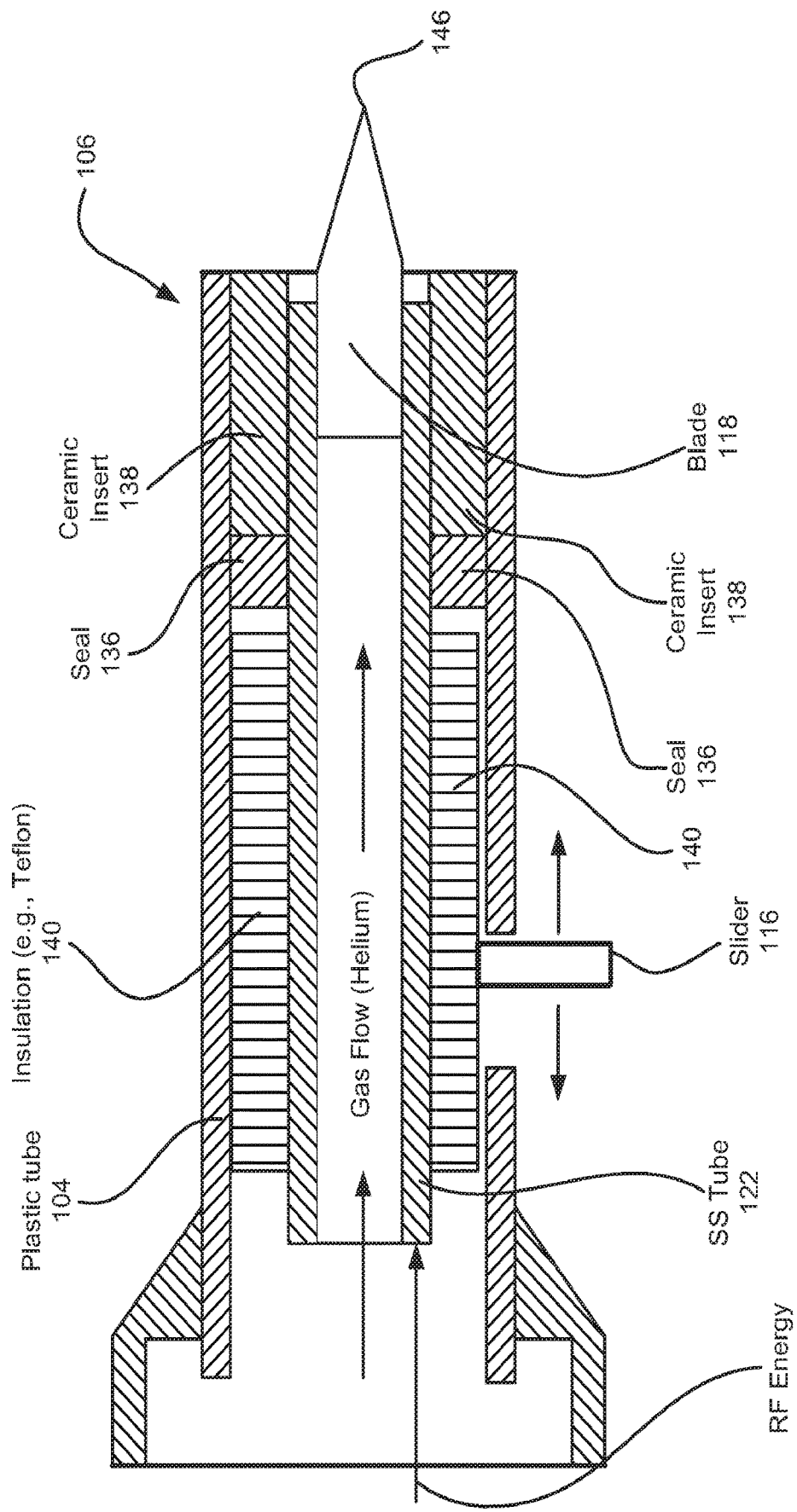
FIG. 4 is an enlarged cross sectional view of the electrosurgical apparatus shown in FIG. 3A with a blade extended.

Referring to FIG. 4, the blade 118 is advanced, via slider 116, so the tip 146 is extended pass the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used to excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and enveloped with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
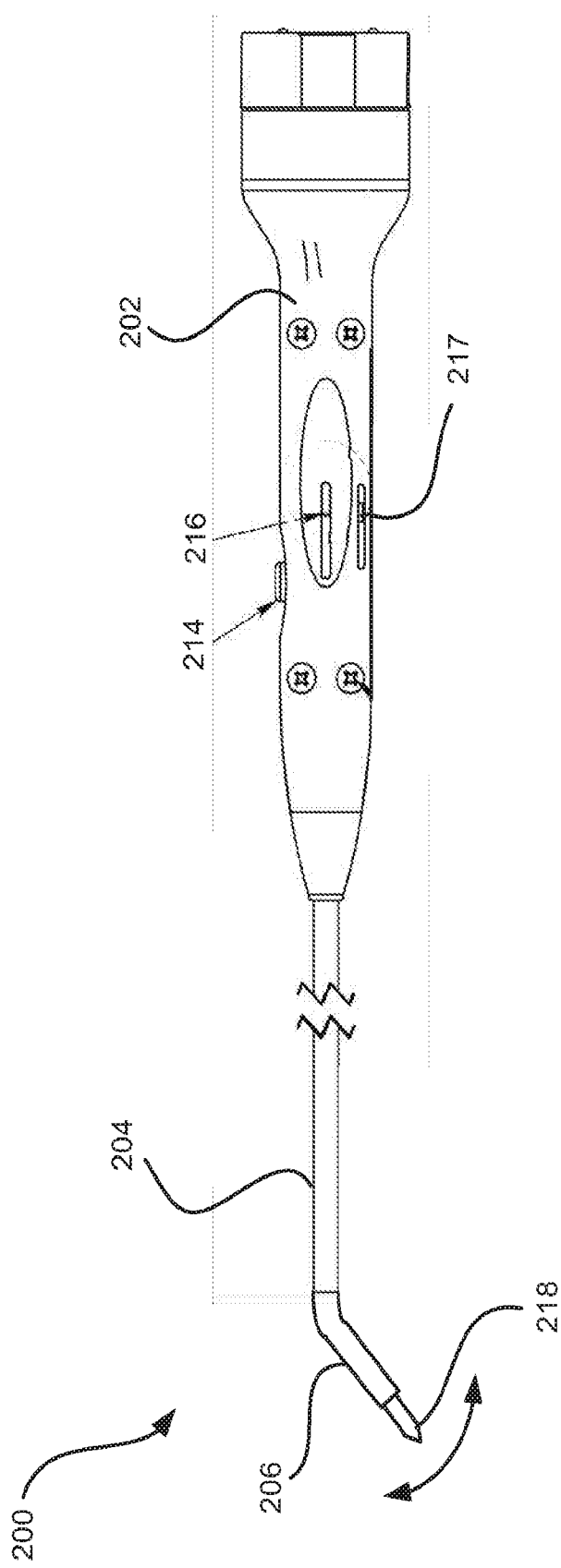
FIG. 5 illustrates an exemplary electrosurgical apparatus including an articulating distal end in accordance with an embodiment of the present disclosure.

In a further embodiment, the electrosurgical apparatus of the present disclosure will have an articulating distal end. Referring to FIG. 5, the electrosurgical apparatus 200 will have similar aspects to the embodiments described above. In this embodiment, however, the distal end 206, e.g., approximately 2 inches, is flexible to allow it to maneuver at the surgical site. An additional control 217, e.g., a slider, trigger, or the like, is provided in the proximal housing 202 to control the bending of the distal end 206. As in the above described embodiments, a button 214 is provided to apply electrosurgical energy to the blade 218 and, in certain embodiments, enable gas flow through the flow tube. Furthermore, slider 216 will expose the blade 218 at the open distal end 206 upon activation.

In one embodiment, the articulating control 217 will include two wires, one pulling to articulate and one pulling to straighten the distal end 206. The outer tube 204 will be the similar to the design shown in FIG. 2 and will be rigid, preferably made of Ultem™, Lestran™, or similar material, up to the last 2 inches which would be made of a material similar to that of a gastrointestinal (GI) flexible scope. In certain embodiments, a mesh infused Teflon™ or similar material and a flexible insulating material may be positioned inside the outer tube 204 and would allow the distal end 206 to bend at least 45° and not collapse the inner tube carrying the gas. The blade 218 will be made of a flexible metallic material such as Nitinol™ that would be able to bend but would retain its shape in the straightened position. Alternatively, a straight metal blade 218 would be provided with the distal 2 inches made of a linked metal, e.g., stainless steel, tungsten, etc., such that it would still carry a current but would be bendable and the cutting portion of the blade 218 would be attached to the distal end of the linked portion.

Figure 6A:
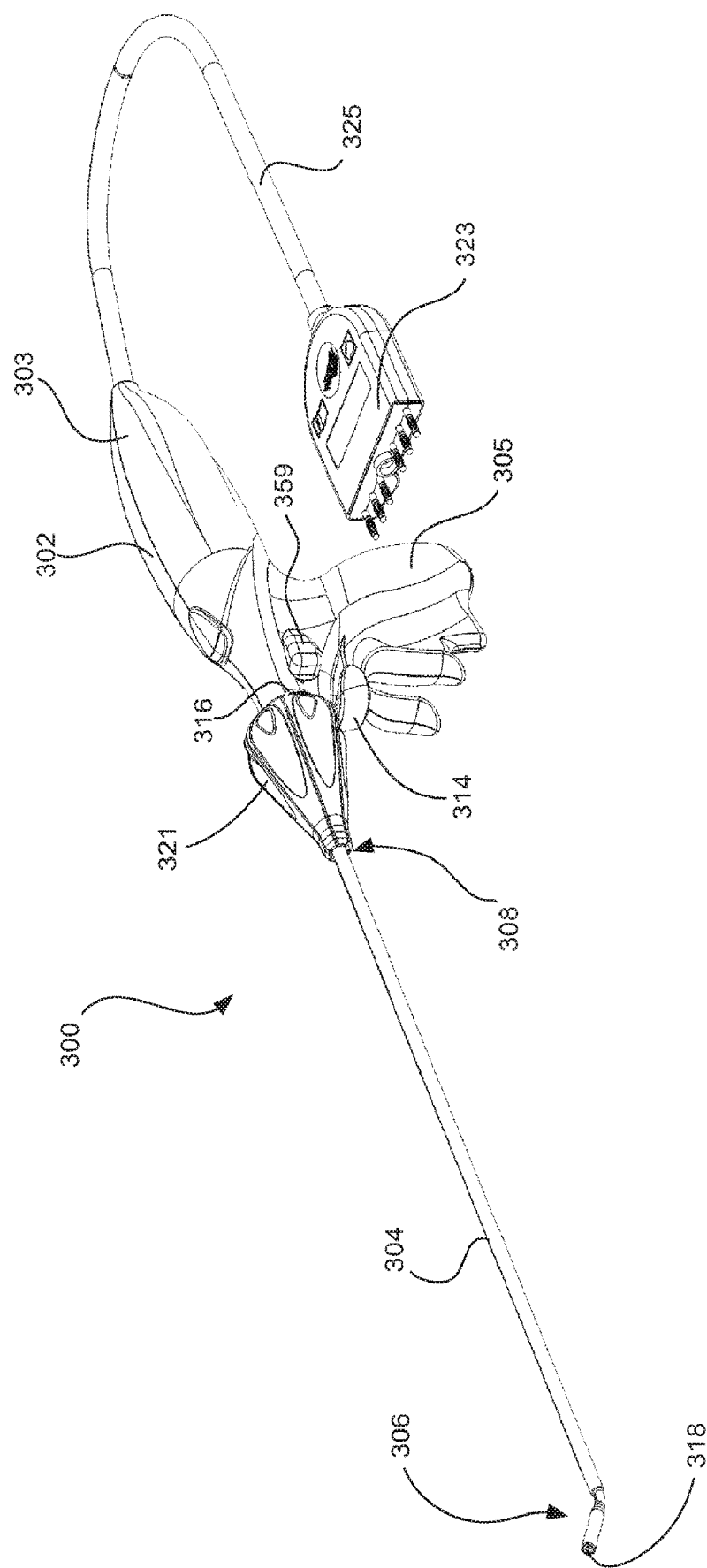
FIG. 6A is a perspective view of an electrosurgical apparatus in accordance with another embodiment of the present disclosure.

In another embodiment, an electrosurgical apparatus of the present disclosure includes a bent tip applicator. Referring to FIGS. 6A-6C, the electrosurgical apparatus 300 may be configured as a trigger-type handpiece or cold plasma bent tip applicator and will have similar aspects to the embodiments described above. In this embodiment, however, the distal end 306 is pre-bent, e.g., in certain embodiments approximately 28.72 mm, and rotatable to maneuver the distal end 306 at the surgical site 18. The electrosurgical apparatus 300 includes a housing 302 with a handle 305 to facilitate maneuvering of the apparatus by an operator. The electrosurgical apparatus 300 further includes a transformer 320 disposed in a proximal end 303 of the housing 302, an activation button 314 for activating the applicator or handpiece to generate plasma configured as a trigger-type button, an insulating tube 304 with a discharge electrode or blade 318 disposed therein. The discharge electrode or blade 318 is coupled to a conductive metal tube 322 which is further coupled to a slider button 316, collectively referred to as a slider assembly 319, which will be described in more detail below with reference to FIGS. 7A-7D. The slider button 316 moves the metal tube 322 which extends or retracts the discharge electrode or blade 318 beyond the distal end 306 of the insulating tube 304. A knob 321 is provided at the proximal end 308 of the insulating tube 304 to enable 360 degree rotation of the insulating tube 304 and thus the distal end 306 of the applicator. Additionally, a connector 323 is provided for coupling the applicator to an electrosurgical generator. In certain embodiments, the connector 323 receives electrosurgical energy and gas which it provides to the applicator or apparatus 300 via cable 325.

Figure 7A:
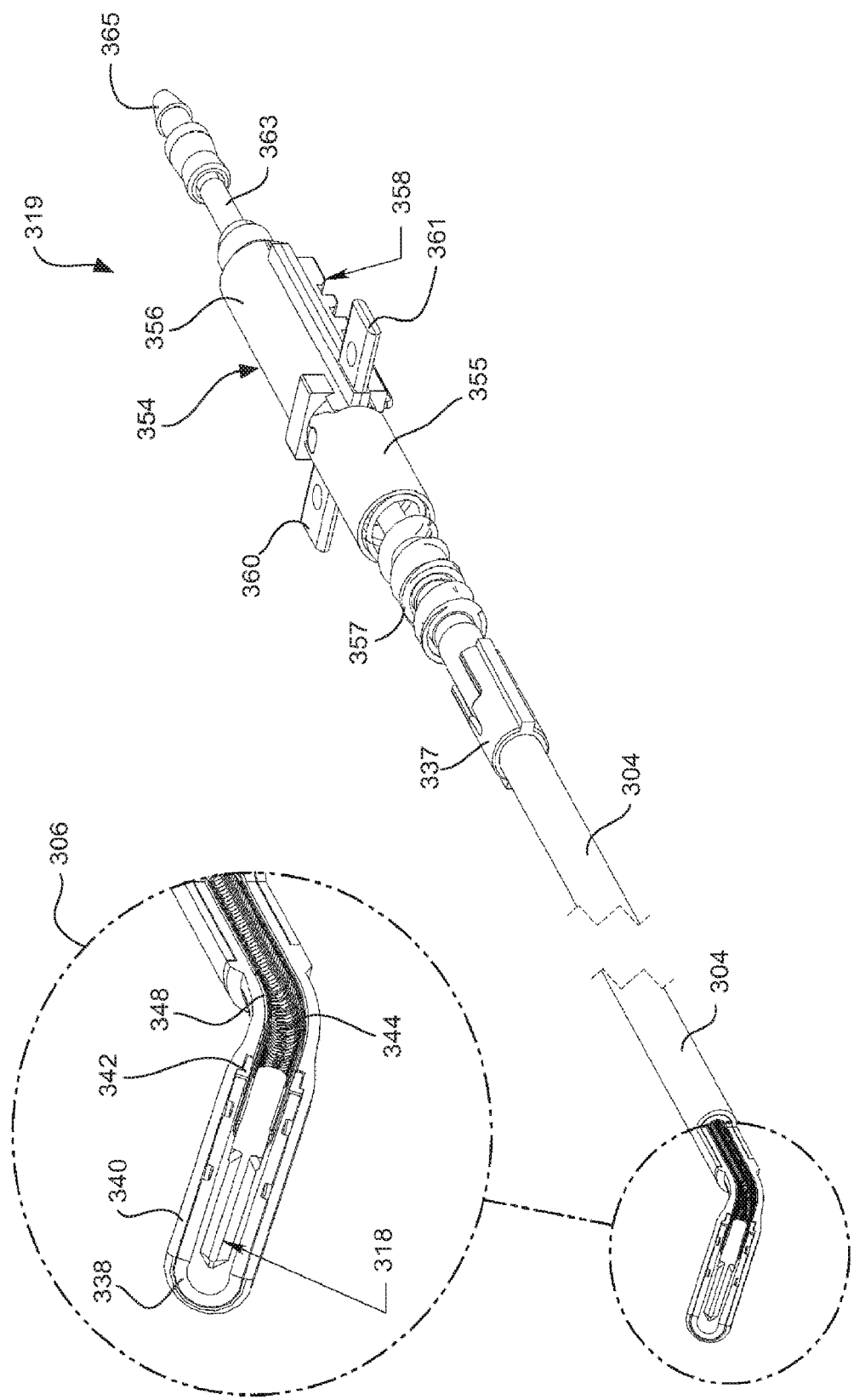
FIG. 7A is a perspective view of a slider assembly in accordance with an embodiment of the present disclosure.
Figure 7B:
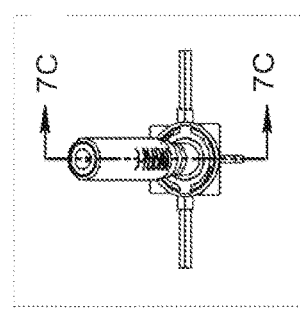
FIG. 7B is a front view of the electrosurgical apparatus shown in FIG. 7A.
Figure 7C:
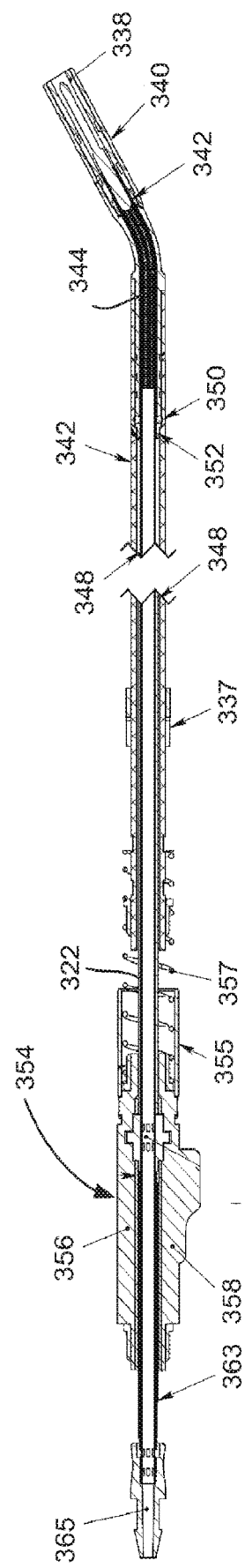
FIG. 7C is a cross sectional view of the slider assembly shown in FIG. 7B taken along line 7C-7C.
Figure 7D:
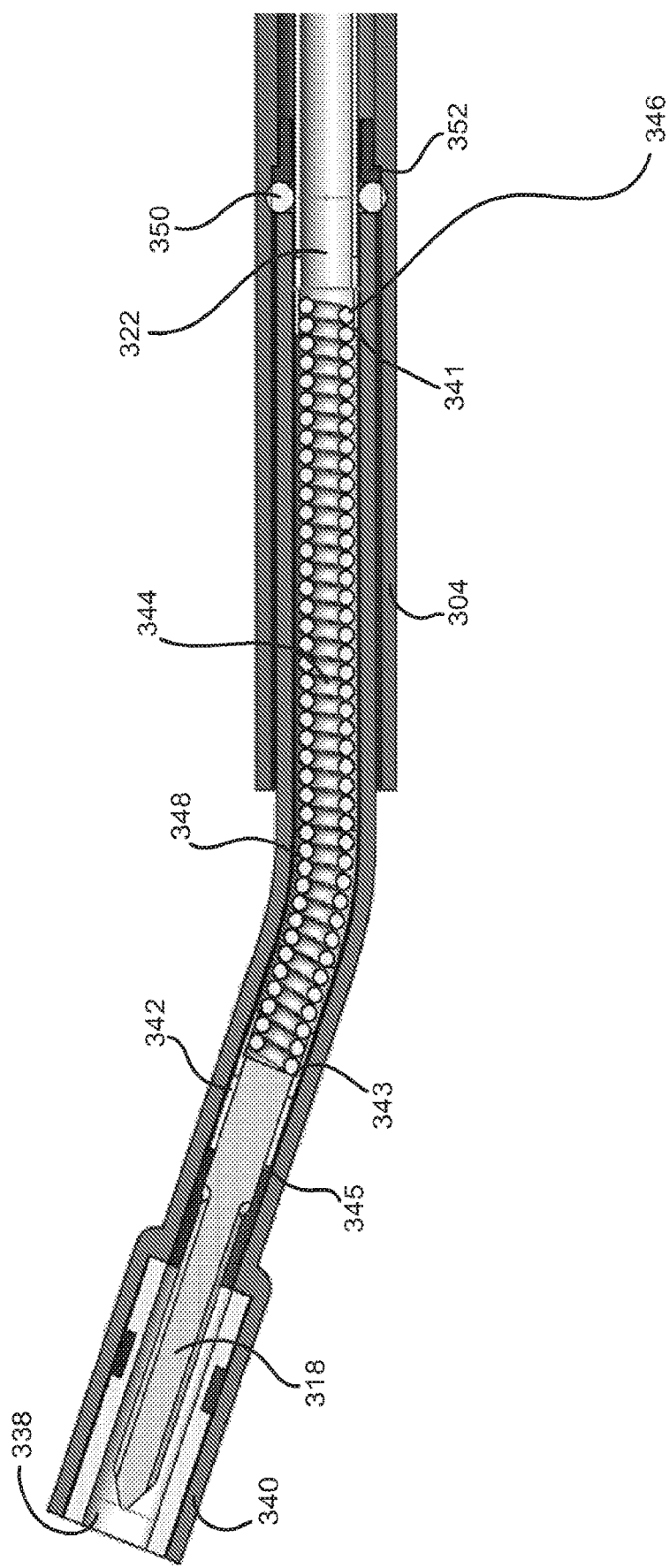
FIG. 7D is an enlarged cross sectional view of a distal end of the slider assembly shown in FIG. 7A.

Referring to FIGS. 7A-7D, the slider assembly 319 will be described in more detail, where FIG. 7A is a perspective view of the slider assembly 319, FIG. 7B is a front view of the slider assembly 319, FIG. 7C is a cross sectional view of the slider assembly 319, and FIG. 7D illustrates the internal construction of the distal end 306 of the slider assembly 319. Starting from the distal end 306 of the apparatus 300, a ceramic insert 338 is used to protect an outer tube distal housing 340 from potentially high temperatures when the device is used in the plasma beam generation mode. The outer tube distal housing 340 is formed from a shape memory polymer or material which retains its mechanical properties at high temperatures. An exemplary shape memory polymer includes a poly ether-ether ketone (PEEK) thermoplastic polymer, although other shape memory material is contemplated to be within the scope of the present disclosure. The outer tube distal housing 340, which has a slightly larger diameter adjacent to the ceramic insert 338, is sufficiently rigid to provide mechanical support for the tip assembly, yet flexible enough to accommodate the various bend angles that the tip may be preset to. An electrode or surgical blade 318 is housed within the outer tube housing 340 and attached to an adaptor tube 342 which connects to a spring 344. The proximal end 346 of the spring 344 is attached to the flow tube 322. It is to be appreciated that the coupling of components, e.g., between the spring 344 and flow tube 322 (generally denoted by reference numeral 341), between the spring 344 and adaptor tube 342 (generally denoted by reference numeral 343) and between the adaptor tube 342 and blade 318 (generally denoted by reference numeral 345), may be achieved by various methods including but not limited to laser welding.

A heat shrink tube 348, which may alternatively be configured as a flexible tube or wrap, is disposed around and firmly covers the spring 344. The heat shrink tube 348, flexible tube, or wrap provides a gas seal and also seals the spring 344 to the flow tube 322, i.e., the heat shrink tube 348 is provided at the junction of the spring 344 and flow tube 322 and extends over at least a portion of the flow tube 322. The spring/heat shrink tube combination is sufficiently flexible to allow an approximately 15 to 30 degree bend once the applicator tip emerges from the distal end of a trocar. It is to be appreciated that the result of the heat shrink tube 348 covering the spring 344 mimics the characteristics of the flow tube 322. This allows the passing of gas, e.g., through the flow tube 322 and heat shrink tube 348 and over the blade 318, without leaking out and enables flexibility through the 15 to 30 degree bent tip. It is to be appreciated that the heat shrink tube 348, covering tube, or wrap may be made from various materials which are insulating and gas impermeable, however are flexible enough to conform to the spring 344 to seal the spacings between coil turns and allow bending through various angles. It is further to be appreciated that other acute angles of the bent tip are contemplated to be within the scope of the present disclosure.

The flow tube 322, spring 344, and adaptor tube 342 all permit the flow of both inert gas and electrical energy to the surgical blade 318. An O-ring 350, optionally held in place by O-ring spacer 352, affects a gas seal and prevents inert gas leakage back into the housing 302 or handpiece. The outer tube housing 304, e.g., formed from Lestran™ or other suitable non-conductive material, provides both mechanical support for the entire assembly, and electrical safety insulation.

A retaining sleeve or anti-slip ring 337 is disposed on the tube 304. The anti-slip ring 337 engages the knob 321 via groove 339 to impact rotation to tube 304 and distal end 306, the details of which will be described below in relation to FIGS. 8C, 8D and 8E. A slider housing 354, including upper slider housing 356 and lower slider housing 358, is coupled to the flow tube 322. The slider housing 354 further includes wing members 360, 361 coupled to slider button 316 which is accessible on an outer surface of the housing 302. A barrier sleeve 355 is coupled to the slider housing 354 to retain a spring 357 disposed about the flow tube 322. In use, sliding the slider button 316 distally causes the flow tube 322 to move toward the distal end 306 of the applicator to extend the electrode 318 beyond the tip of the outer tube distal housing 340. To retract the electrode 318, a release button 359 is actuated where spring 357 drives the slider housing 354 toward the proximal end 308 of the applicator or tube 304.

An electrical contact 363, e.g., a copper contact, is disposed around the proximal end of the flow tube 322 and is coupled to an electrosurgical energy source for providing the electrosurgcial energy to the electrode 318. A gas flow coupler 365 is disposed on the proximal end of the flow tube for coupling to the cable 325 for providing gas to flow tube 322.

Figure 8A:
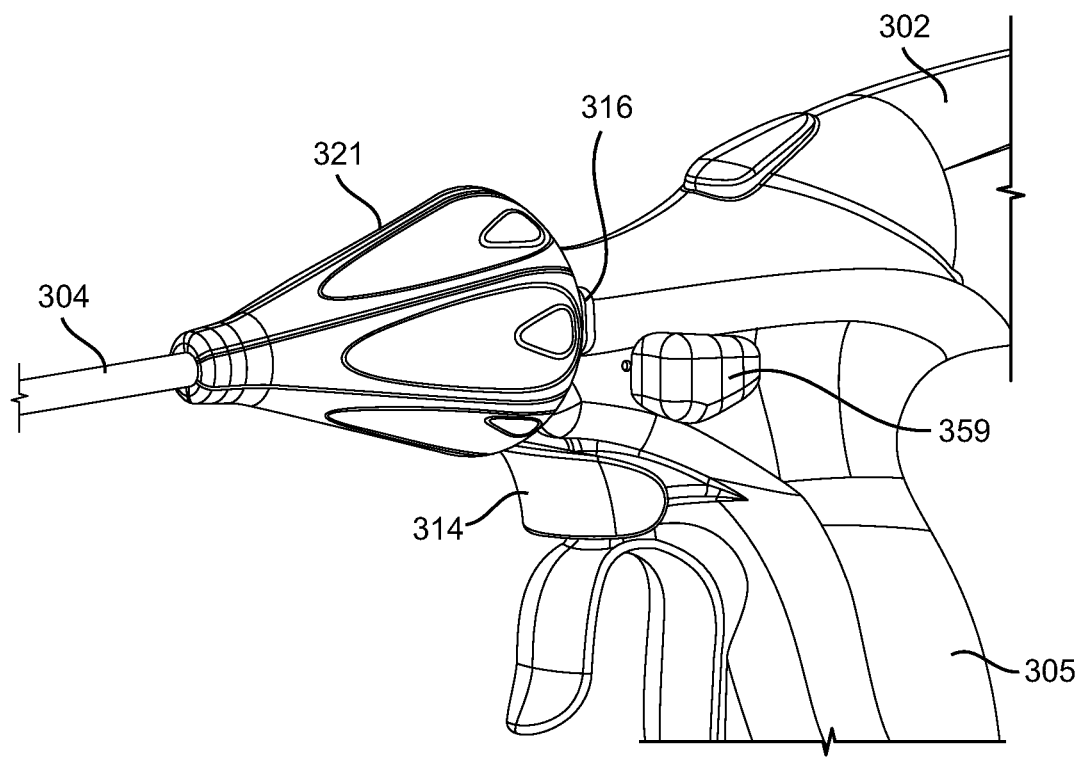
FIG. 8A is a partial view of the electrosurgical apparatus shown in FIG. 6.
Figure 8B:
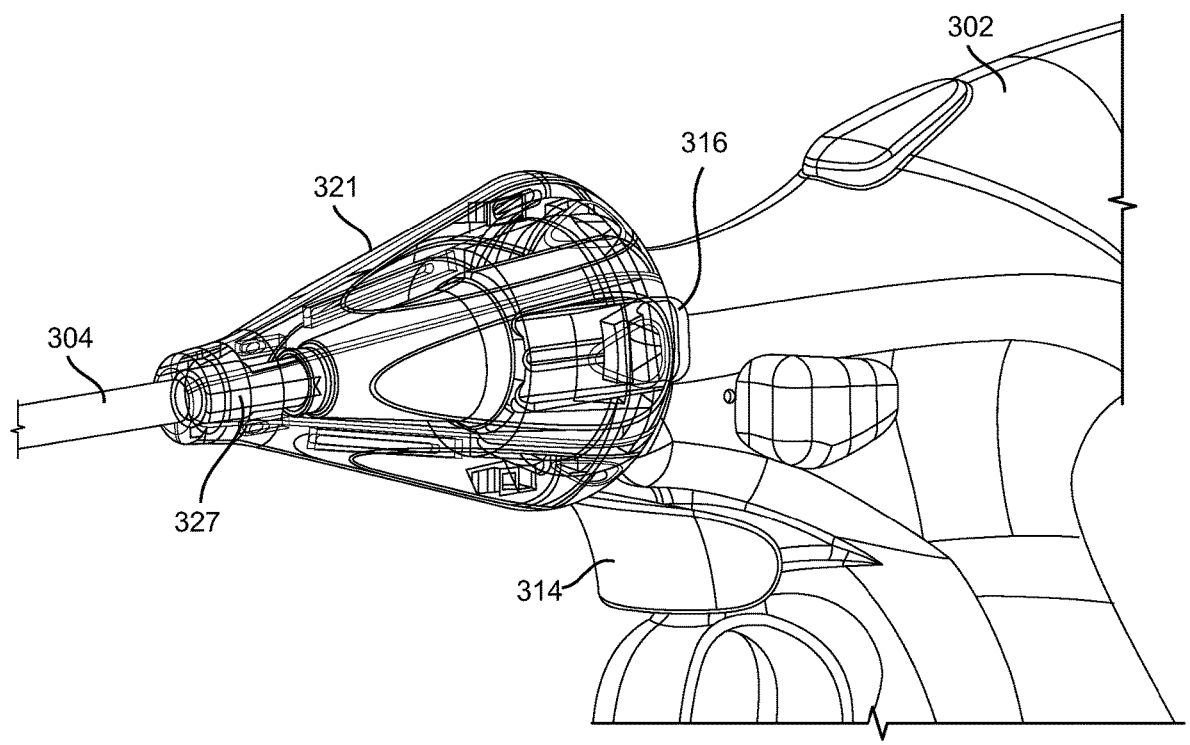
FIG. 8B is the partial view shown in FIG. 8A with a knob shown in phantom.
Figure 8C:
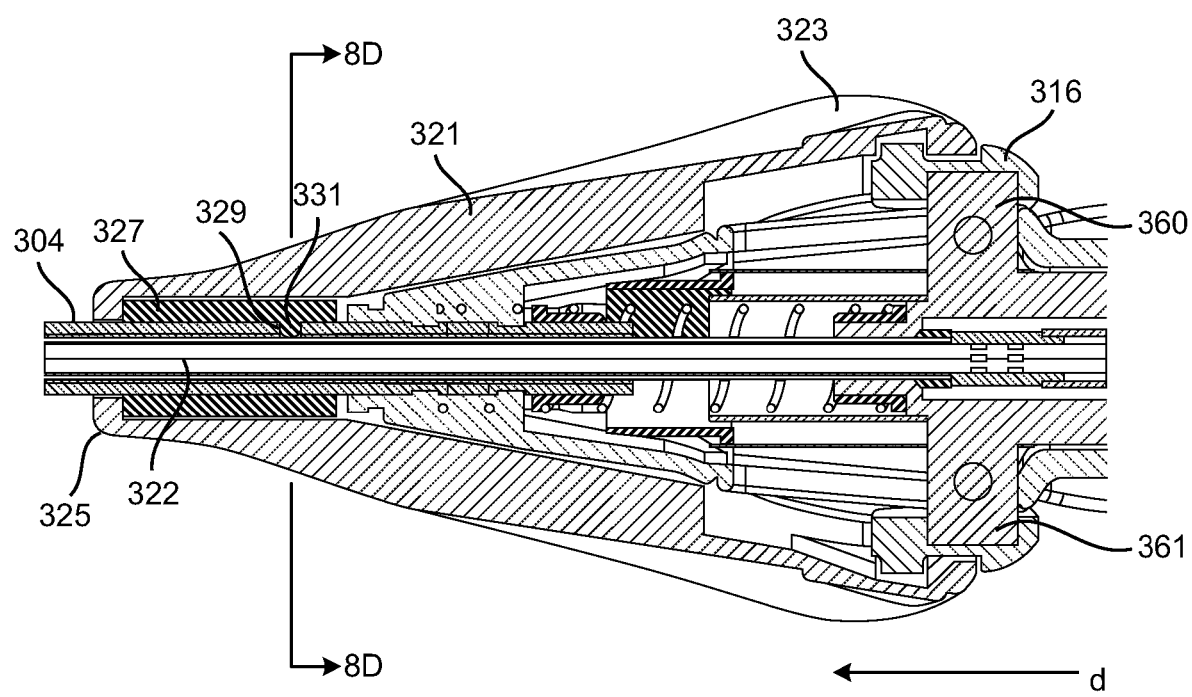
FIG. 8C a cross sectional view of a knob and slider of the electrosurgical apparatus in accordance with the present disclosure.
Figure 8D:
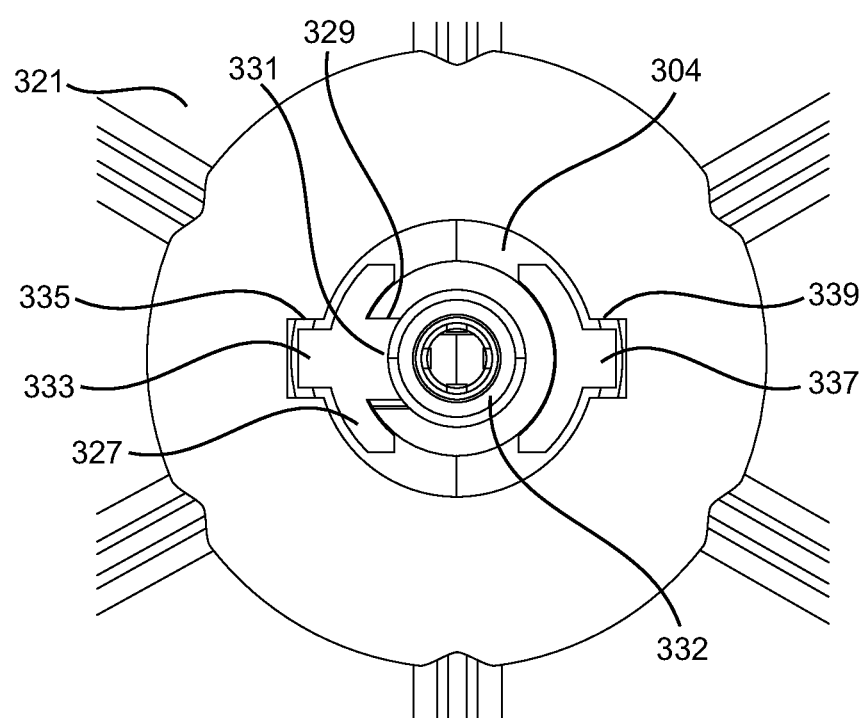
FIG. 8D is a cross sectional view of the electrosurgical apparatus shown in FIG. 8C taken along line 8D-8D.
Figure 8E:
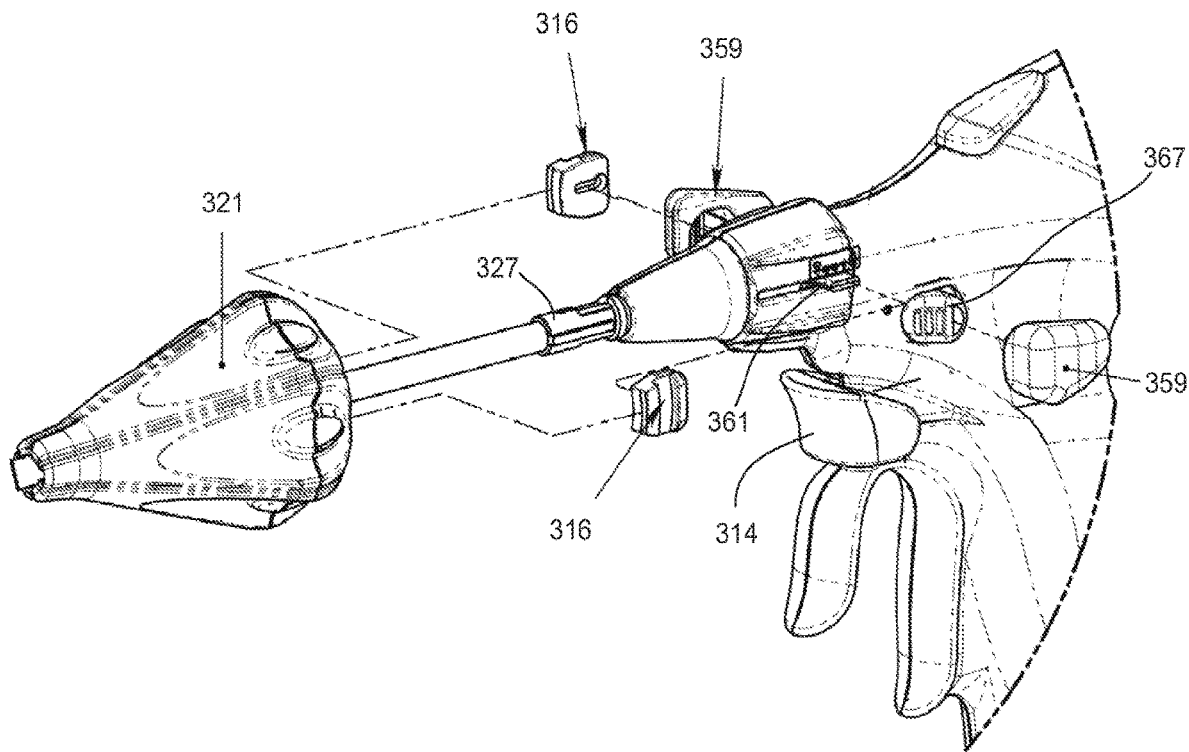
FIG. 8E is a partial exploded view of the electrosurgical apparatus shown in FIG. 8A showing the knob/slider details in accordance with an embodiment of the present disclosure.

FIG. 8A shows an example of the applicator attached to a housing or hand piece 302 which also allows full rotation of the distal end 306 of the applicator around 360 degrees. A rotation knob 321 on the hand piece 302 permits rotation of the entire bent tip of the distal end 306 and support tube assembly. The hand piece 302 also houses the various levers and pushbuttons to extend the surgical blade or electrode (e.g., via slider button 316), activate the application of electrical energy and gas flow (e.g., via trigger 314), retract the blade or electrode (e.g., via release button 359) and other user-defined functions, such as preset electrical power levels and gas flow rates.

Referring to FIGS. 8B through 8E, an operation of the knob 321 will be described. Knob 321 has a generally frustoconical shape including a proximal end 323 and a distal end 325. The proximal end 323 is coupled to the slider button 316 via, for example, a tongue and groove arrangement. The tongue and groove arrangement allows for the rotation of the knob 321 about the slider button 316. An anti-slip ring 327 (also known as a retaining sleeve) is fixedly coupled to the outer tube 304 via groove 329 and tab 331. The distal end 325 of the knob 321 makes contact with the anti-slip ring 327 to enable rotation of the outer tube 304. When the knob 321 is rotated, at least one rib or protrusion 333 on an outer surface of the ring 327 catches a groove 335 formed on the inner surface of the knob 321 to enable rotation.

When the knob 321 is rotated, the anti-slip ring 327 rotates and thus the outer tube 304 rotates, while the inner flow tube 322 is rotationally fixed. The outer tube 304 is fixedly coupled to the outer tube distal housing 340. As the outer tube distal housing 340 is rotated, the spring 344 and blade 318 float within the outer tube distal housing 340 to enable rotation of the distal end 306. That is, the spring 344 and blade 318 do not rotate and the blade 318 will remain in the same plane throughout the rotation of the outer tube distal housing 340, i.e., the plane of the blade will remain parallel to the plane of the handle 305 of the housing 302. For example, if the blade 318 is vertical, the blade 318 remains vertical at any rotated angle of the outer tube 304/outer tube distal housing 340.

The slider button 316 and knob 321 move together along the longitudinal axis of the apparatus to extend and retract the blade 318. When the slider button 316 is activated in the direction as indicated by arrow d, the knob 321 moves in the same direction sliding over the ring 327. The slider button 316 causes the inner flow tube 322 to move while the outer tube 304 remains in the same position. It is to be appreciated that the outer tube 304 moves rotationally but not in the direction of the longitudinal axis. Furthermore, it is to be appreciated that the inner flow tube 322 moves in the direction of the longitudinal axis but not rotationally. To retract the electrode 318, a release mechanism 367 is activated via the release button 359 to allow the spring 357 to drive the inner flow tube 322, via the slider housing 354, toward the proximal end 308 of the applicator.

Figure 9A:
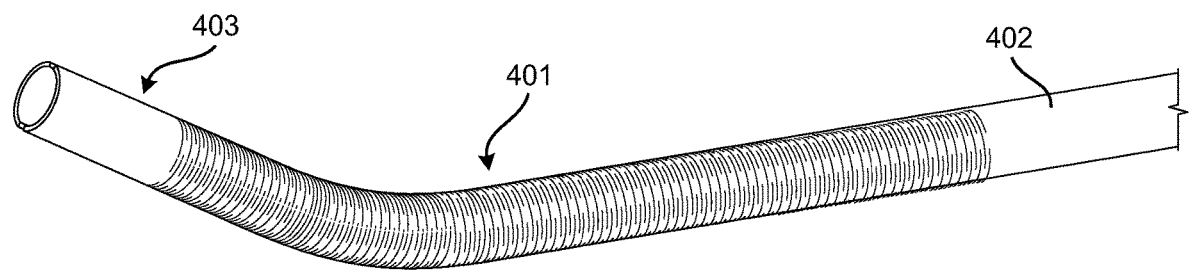
FIG. 9A illustrates an inner conductive tube in accordance with another embodiment of the present disclosure.
Figure 9B:
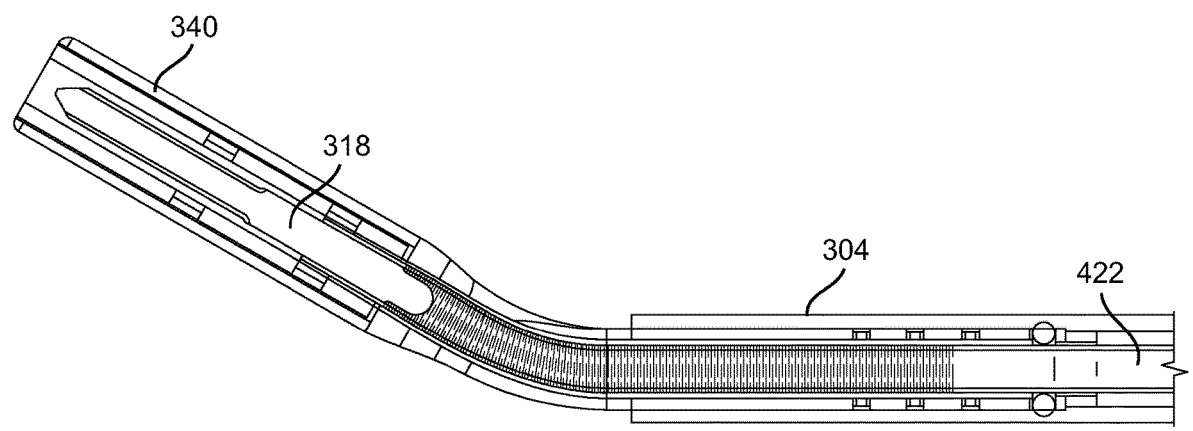
FIG. 9B is a cross sectional view of a distal end of the electrosurgical apparatus employing the inner conductive tube shown in FIG. 9A.

FIG. 9A illustrates another embodiment of an inner conductive tube 422 in accordance with the present disclosure. The inner conductive tube 422 includes a plurality of cuts 401, e.g., laser cuts, that enable a distal end 403 of the tube 422 to be flexible enough to allow rotation of the distal end 306 of the electrosurgical apparatus as described above. Referring to FIG. 9B, a cross sectional view of a distal end of the electrosurgical apparatus employing the inner conductive tube 422 shown in FIG. 9A is illustrated. The distal end 403 of the tube 422 is fixedly coupled to blade 318. The operation of the electrosurgical apparatus employing the tube 422 is similar to that described in relation to the embodiment shown in FIGS. 7 through 8C.

Figure 10A:
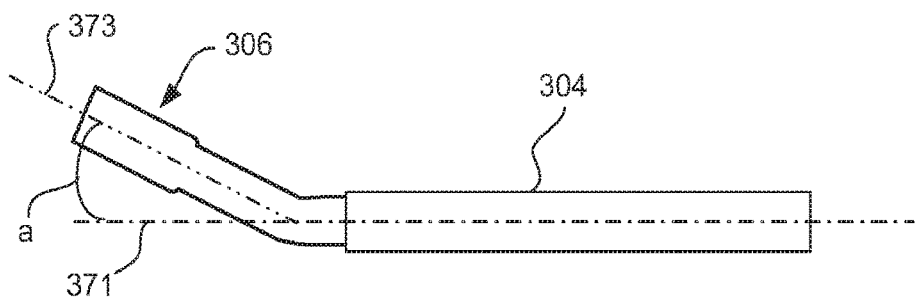
FIGS. 10A-10C illustrate an operation of the electrosurgical apparatus in accordance with the present disclosure, where
Figure 10B:
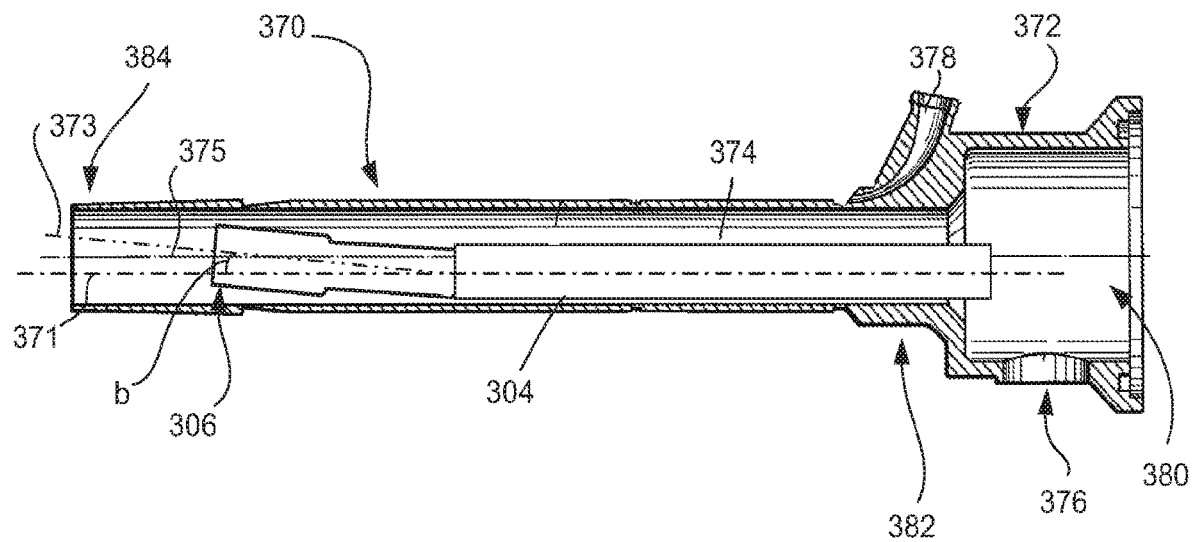
Figure 10C:
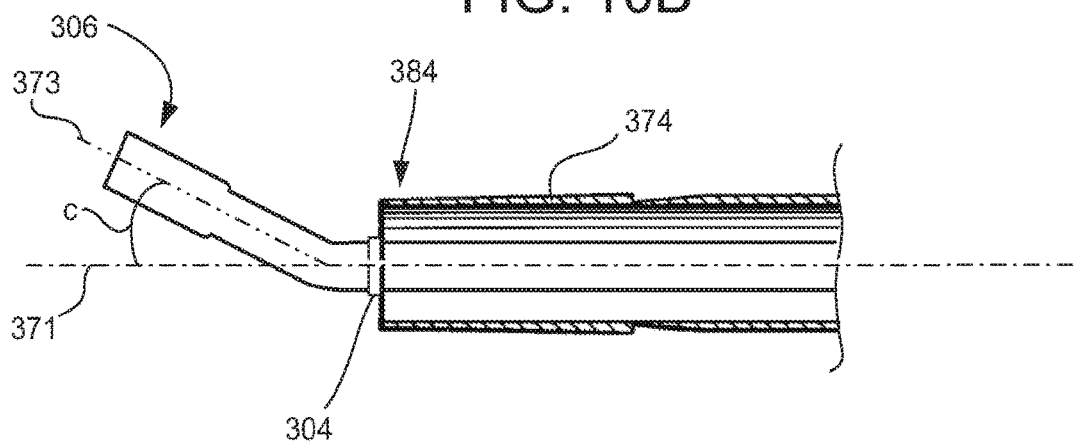

FIGS. 10A-10C illustrate an operation of an electrosurgical apparatus, such as apparatus 300, in accordance with the present disclosure, where FIG. 10A illustrates a distal end of the electrosurgical apparatus before insertion into a trocar, FIG. 10B illustrates the distal end of the electrosurgical apparatus passing through the trocar and FIG. 10C illustrates the distal end of the applicator emerging from the distal end of the trocar when fully inserted.

FIG. 10A illustrates the normal or unbiased state of the cold plasma applicator. As shown in FIG. 10A, the distal end 306 of the cold plasma applicator is pre-bent relative to the tube 304 at predetermined angle a, e.g., from about 0 degrees to about 20 degrees, although other angles are contemplated to be within the scope of the present disclosure. As can be seen in FIG. 10A, a longitudinal axis 373 of the distal end 306 is pre-bent at an acute angle, e.g., angle a, relative to the longitudinal axis 371 of the tube 304. It is to be appreciated that the pre-bent angle is the normal or unstressed position of the distal end 306. The distal end 306 can be manipulated, or stressed, so the distal end 306 relative to the outer tube 304 can be at an angle less than the predetermined angle a so the applicator may pass through a trocar.

FIG. 10B illustrates an exemplary cannula or trocar 370, which includes a hub 372 connected to tubular member 374 aligned along a central axis 375. In certain embodiments, the hub 372 may include a port 376 for receiving valving and gas input components and a fluid input 378 for introduction of necessary or desired fluids to irrigate a surgical site. The hub 372 includes an opening 380 for receiving the cold plasma applicator 300 which is to be inserted into the tubular member 374. The tubular member 374 includes a proximal end 382 and a distal end 384. As shown in FIG. 10B, the distal end 306 of the cold plasma applicator 300 is straightened relative to the tube 304 at angle b, where angle b is less than angle a. It is to be appreciated that angle b is measured as the angle between the longitudinal axis 373 of the distal end 306 and the longitudinal axis 371 of the tube 304. With the distal end 306 at angle b, i.e., the biased or stressed state, the cold plasma applicator 300 is inserted into the opening 380 of trocar 370 and the distal end 306 and tube 304 will fit in the tubular member 374 of trocar 370. It is to be appreciated that with the longitudinal axis 373 of the distal end 306 at angle b, the outer tube distal housing 340 is substantially coaxial (or linear) with the outer tube 304.

Referring to FIG. 10C, after the distal end 306 of the cold plasma applicator 300 passes the opening at the distal end 384 of the trocar, the distal end 306 attempts to return to its pre-insertion state, i.e., the unstressed state. The distal end 306 moves to an angle c which is slightly less than the pre-insertion angle a. Angle c is measured as the angle between the longitudinal axis 373 of the distal end 306 and the longitudinal axis 371 of the tube 304. It is to be appreciated that angle c is less than angle a, but greater than angle b, i.e., a>c>b. Once the distal end 306 passes the opening at the distal end 384 of the trocar, the bent tip can then be externally rotated by a user or surgeon via knob 321 to more accurately be directed to the target tissue.

It is to be appreciated that the shape memory property of the outer tube distal housing 340 enables the distal end 306 of the applicator to be pre-bent to a predetermined angle most suitable for a particular procedure, straightened to an angle less than the predetermined angle to allow the applicator to be inserted into a trocar or the like, and returned to substantially the predetermined angle when at the surgical site. The various embodiments of the present disclosure enable an electrosurgical apparatus to redirect a plasma beam relative to the longitudinal axis of the insulating outer tube without the need of complicated and difficult to operate mechanisms.

It is further to be appreciated that by retracting the electrosurgical apparatus, e.g., apparatus 300, into the trocar 370 so that a small portion of the distal end 306 just extends beyond the distal end of the trocar 370 (e.g., approximately 1-5 mm), the outer distal housing 340 becomes substantially coaxial with the outer tube housing 304 and the apparatus may be employed to, for example, generate plasma, in a straight on configuration, i.e., in substantially the direction of the central axis of the trocar.

Figure 11A:
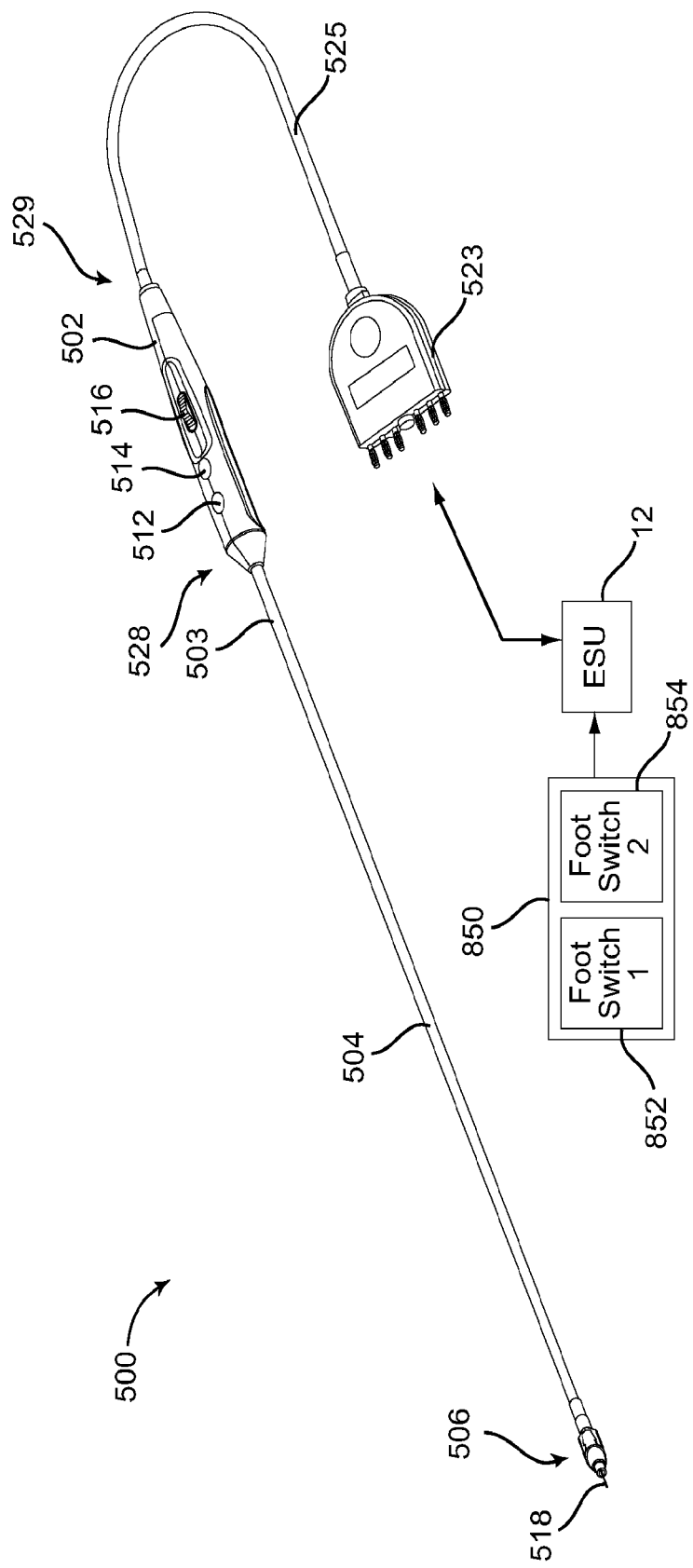
FIG. 11A is a perspective view of an electrosurgical apparatus in accordance with another embodiment of the present disclosure.

Referring to FIG. 11A, an electrosurgical apparatus 500 is shown in accordance with an embodiment of the present disclosure.

Figure 11B:
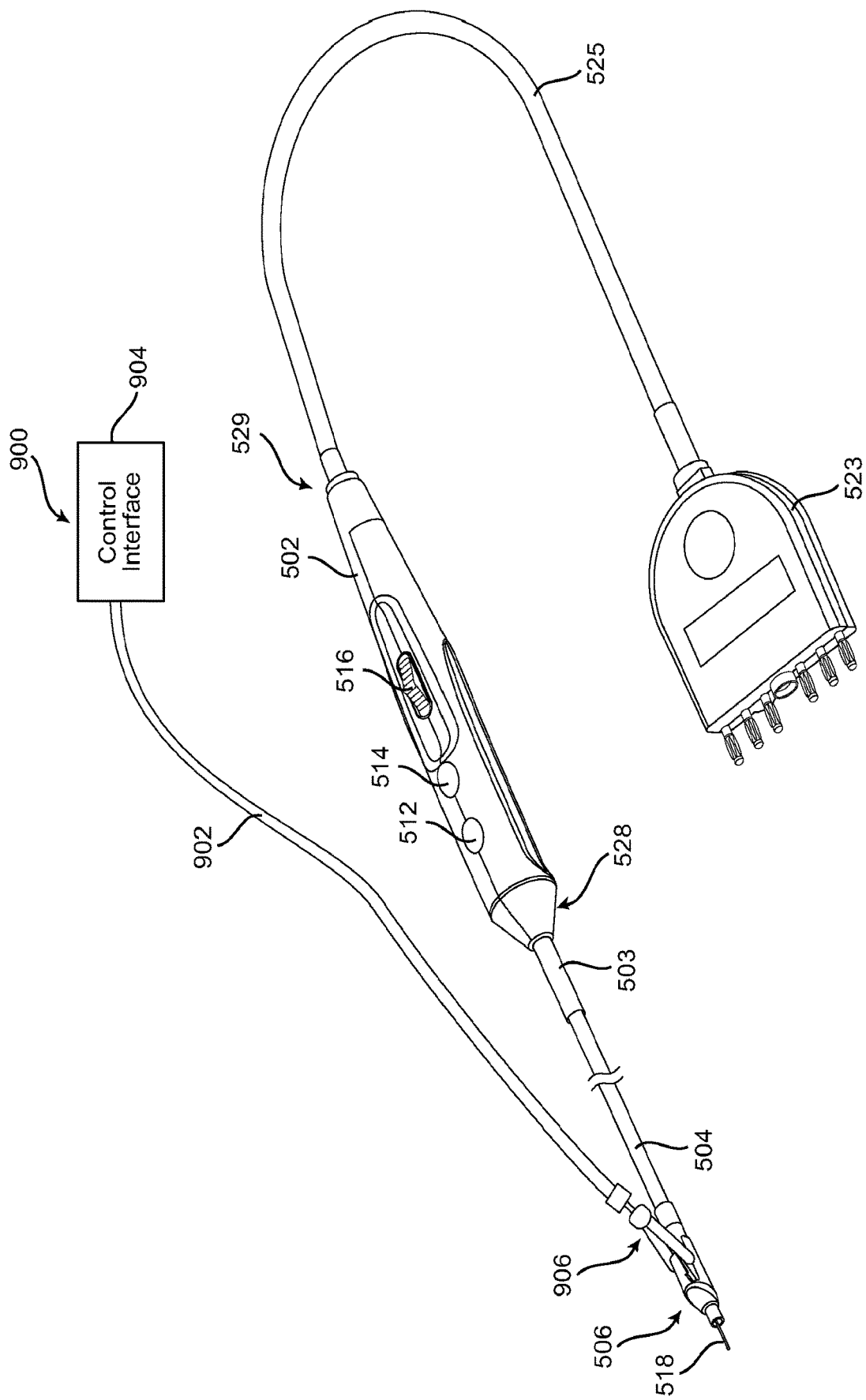
FIG. 11B is a perspective view of the electrosurgical apparatus of FIG. 11A coupled to forceps in accordance with the present disclosure.

As shown in FIG. 11A, electrosurgical apparatus 500 includes a distal tip assembly 506, rigid shaft 503, flexible outer insulating tube 504, housing 502, cable 525, and connector 523. Housing 502 is coupled to connector 523 via cable 525. Furthermore, housing 502 is coupled to distal tip assembly 506 via rigid shaft 503 and outer tube 504. It is to be appreciated that, in one embodiment, outer tube 504 is configured to be flexible, such that tip 506 may be rotated or moved to achieve a wide range of positions. Tip 506 is configured such that tip 506 may be grasped using a grasping tool (e.g., forceps) to control the orientation of tip 506. For example, referring to FIG. 11B, apparatus 500 is shown coupled to forceps 900. As shown in FIG. 11B, forceps 900 includes a control interface 904, a shaft 902, and jaws or grasping members 906. As will be described in greater detail below, tip 506 is configured to be grasped by jaws 906 of forceps 900 to control the orientation of tip 506 as desired.

Referring again to FIG. 11A, apparatus 500 may be coupled to an ESU, such as, ESU 12 to receive electrosurgical energy and/or gas therefrom. In one embodiment, housing 502 may include a plurality of buttons, such as, but not limited to, buttons 512 and 514, and one or more sliders, such as, but not limited to, slider 516. In this embodiment, slider 516 is configured to control the advancement and retraction of an electrode 518 relative to tip 506 (as will be described in greater detail below), where electrode 518 is disposed in a channel of tip 506. In some embodiments, electrode 518 is configured as a blade, while in other embodiments, electrode 518 is configured as a needle. In one embodiment, buttons 512 and 514 may be configured to control the modes of operation of apparatus 500, including the characteristics of a plasma beam emitted from an aperture of tip 506. For example, button 512 may be configured to control a J-Plasma or cold plasma mode and button 514 may be configured to control a monopolar coagulation mode with or without gas.

In another embodiment, apparatus 500 may include a foot switch interface 850 for controlling the different modes of operation of apparatus 500. The foot switch interface 850 includes one or more foot switches 852, 854, and is coupled to ESU 12. In response to pressing the one or more foot switches 852, 854, communication signals are sent via foot switch interface 850 to ESU 12 to control the electrosurgical energy provided via ESU 12 to apparatus 500. In this way, foot switch interface 850 is configured to control the mode of operation (e.g., cold plasma, coagulation, ablation, etc.) that apparatus 500 is in during a procedure. It is to be appreciated that although two foot switches 852, 854 are shown, in some embodiments, foot switch interface 850 includes a separate foot switch for each mode of operation of apparatus 500. In other embodiments, additional foot switches may be included in foot switch interface 850 for controlling the power provided by ESU 12 to apparatus 500 and/or the gas provided by a gas supply (e.g., including in ESU 12) to apparatus 500.

Figure 12A:
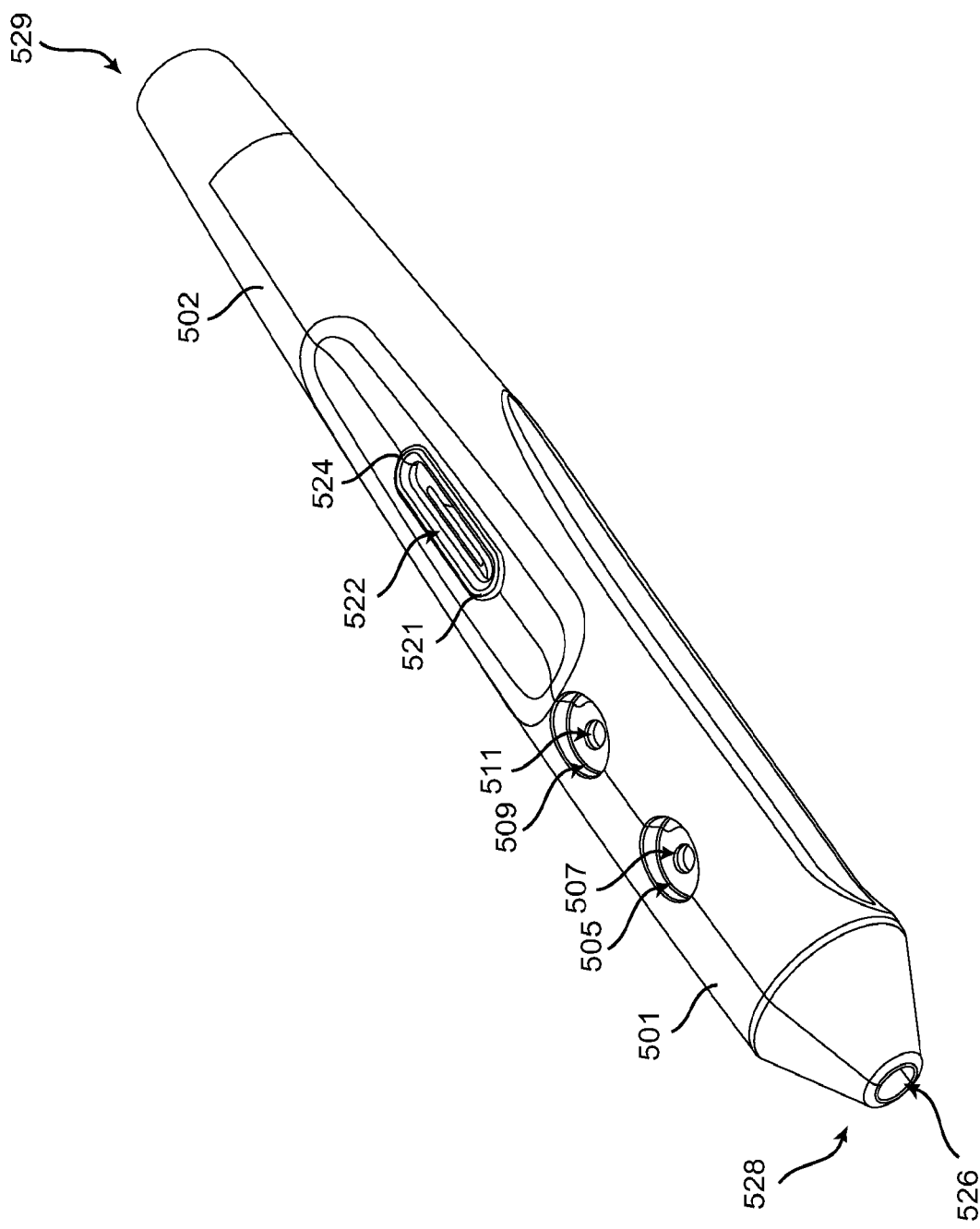
FIG. 12A is a perspective view of a housing of the electrosurgical apparatus of FIG. 11A in accordance with the present disclosure.
Figure 12B:
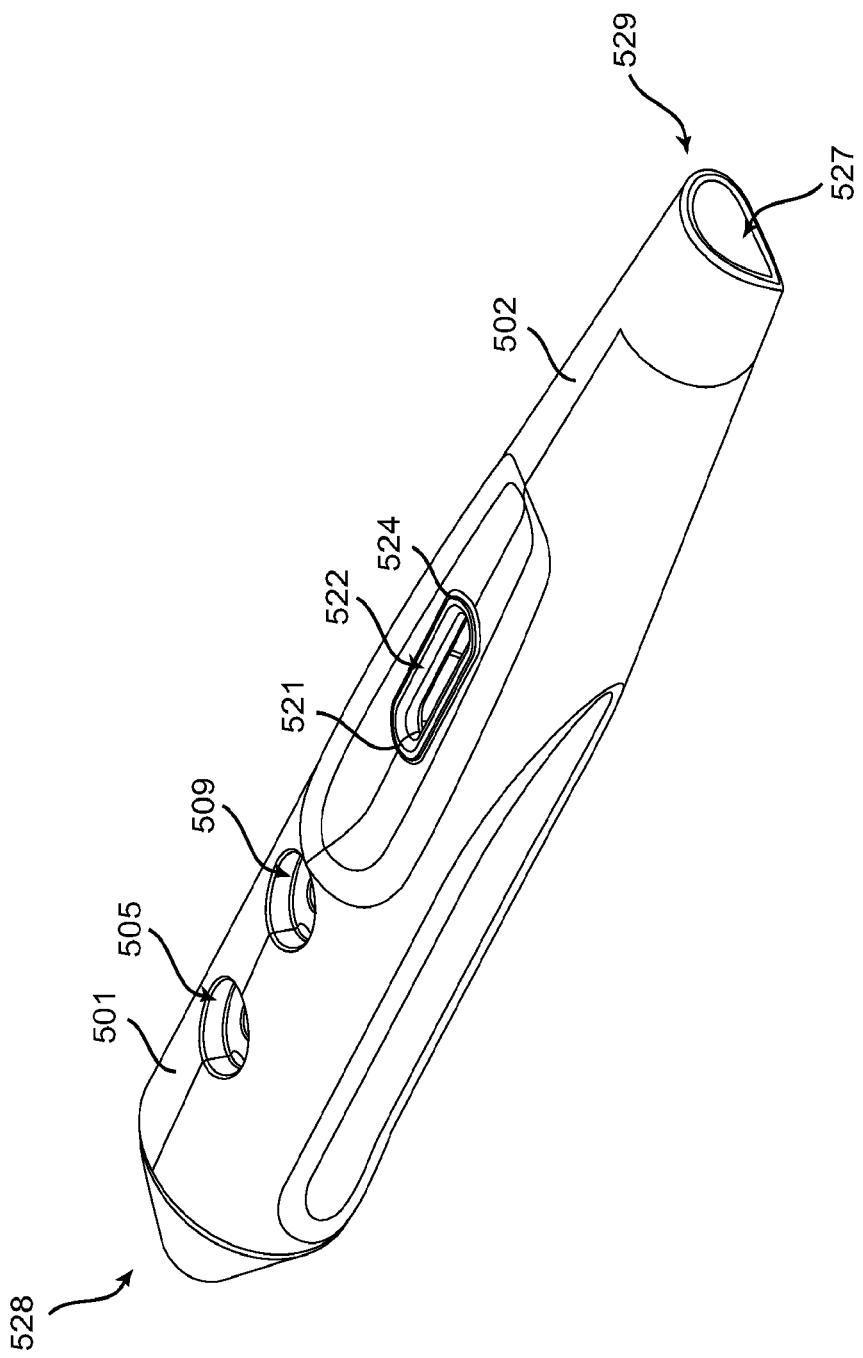
FIG. 12B is another perspective view of the housing of FIG. 12A in accordance with the present disclosure.

Referring to FIGS. 12A and 12B, perspective views of housing 502 are shown in accordance with the present disclosure. As shown in FIGS. 12A and 12B, housing 502 includes a distal end 528 and a proximal end 529. Distal end 528 includes a channel 526, where channel 526 is configured to receive a portion of rigid shaft 503. Proximal end 529 includes channel 527, where channel 527 is configured to receive a portion of a tube or rotation sleeve 530 (shown in FIG. 12E). Housing 502 also includes button cavities 505 and 509 and slider slot 522, where cavities 505, 509 and slot 522 are disposed through an outer surface 501 of housing 502. Button cavity 505 is configured to receive button 512 and button cavity 509 is configured to receive button 514. Furthermore, slider slot 522 is configured to receive slider 516.

Referring to FIGS. 12C and 12D, perspective views of buttons 512, 514 and slider 516 are shown in accordance with the present disclosure. As shown in FIGS. 12C and 12D, button 512 includes a projection 513 and button 514 includes a projection 515. When button 512 is disposed in button cavity 505, projection 513 is configured to be disposed through an aperture 507 of cavity 505. Also, when button 514 is disposed in button cavity 509, projection 515 is configured to be disposed through an aperture 511 of cavity 509. As will be described in greater detail below, when button 512 or 514 is pressed, the projection 513, 515 of button 512, 514 makes contact with a printed circuit board 558 (shown in FIG. 13A) disposed in the interior of housing 502.

As shown in FIGS. 12C and 12D, slider 516 includes a first portion 536, a second portion 517, and a third portion 520. Slider 516 is coupled to housing 502, such that, the first portion 536 of slider 516 is disposed on or directly above the exterior surface 501 of housing 502, the second portion 517 of slider 516 is disposed through slot 522 of housing 502, and the third portion of slider 520 is disposed in the interior of housing 502. Portion 520 of slider 516 includes female member 537 and male member 538, where a channel 519 extends from female member 537 to male member 538. As will be described in greater detail below, slider 516 is configured such that a user can slide slider 516 distally or proximally along slot 522 via portion 536 to extend or retract blade 518, or other suitably shaped electrodes (e.g., a needle electrode). For example, when slider 516 is advanced toward distal end 521 of slot 522, blade 518 is extended past a distal portion of tip 506 and when slider 516 is pulled toward proximal end 524 of slot 522, blade 518 is retracted into a channel of tip 506 (as will be described in greater detail below).

Portion 520 of slider 516 also includes a male member 801 and a channel 662. Male member 801 includes a channel 803. As will be described in greater detail below, channel 803 is configured to receive a portion of a wire or cable and channel 662 is configured to receive a dowel. In one embodiment, channel 803 merges with channel 519 within portion 520 of slider 516 to enable the portion of the wire or cable to be coupled to a conductive gas flow tube.

Figure 12E:
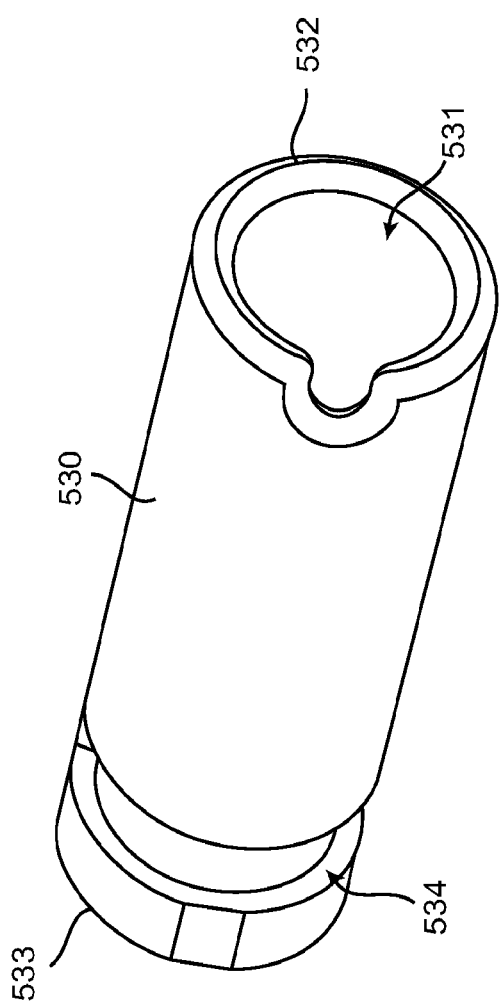
FIGS. 12E and 12F are perspective views of a rotational sleeve of the electrosurgical apparatus of FIG. 11A in accordance with the present disclosure.
Figure 12F:
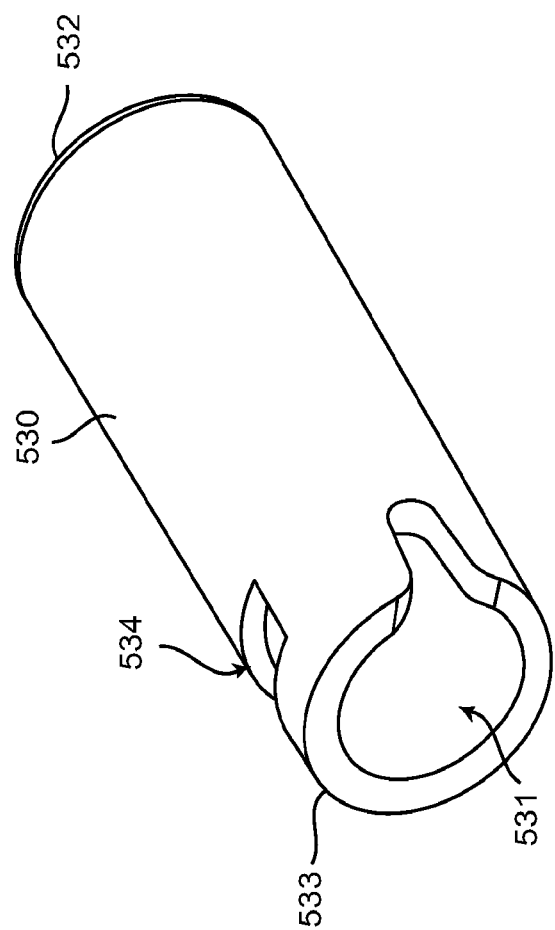

As stated above, channel 527 of housing 502 is configured to receive and retain a rotation sleeve 530. Referring to FIGS. 12E and 12F, perspective views of sleeve 530 are shown in accordance with the present disclosure. As shown in FIGS. 12E and 12F, in one embodiment, sleeve 530 is configured in a generally cylindrical shape. Sleeve 530 includes an interior channel 531 that extends from distal end 532 of sleeve 530 to proximal end 533 of sleeve 530. Furthermore, sleeve 530 includes a slot 534 disposed on the exterior surface of sleeve 530. In one embodiment, slot 534 is configured as a semi-circle (i.e., slot 534 wraps around the exterior cylindrical surface of sleeve 530, but does not form a complete circle).

Slot 534 is configured to receive a tab disposed in channel 527. For example, referring to FIG. 12G, a partial perspective view of the proximal portion 529 of housing 502 is shown in accordance with the present disclosure. As seen in FIG. 12G, channel 527 includes a semi-circular tab 551 disposed on an inner surface 552 of housing 502. When sleeve 530 is disposed in channel 527, tab 551 is disposed in slot 534. Thus, sleeve 530 is rotatably disposed in channel 527 and coupled to housing 502.

Figure 13A:
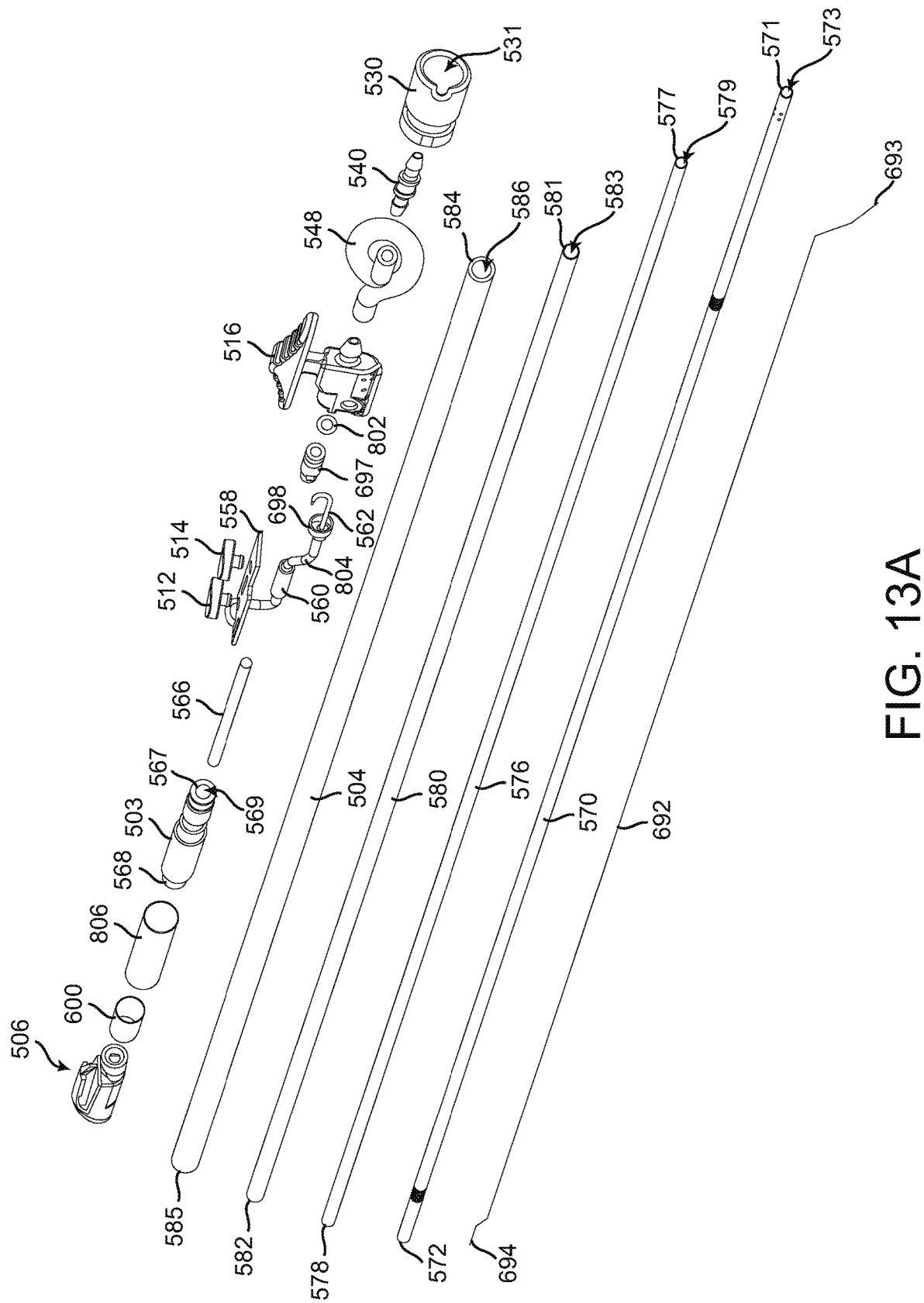
FIGS. 13A and 13B are exploded perspective views of the electrosurgical apparatus of FIG. 11A in accordance with the present disclosure
Figure 13B:
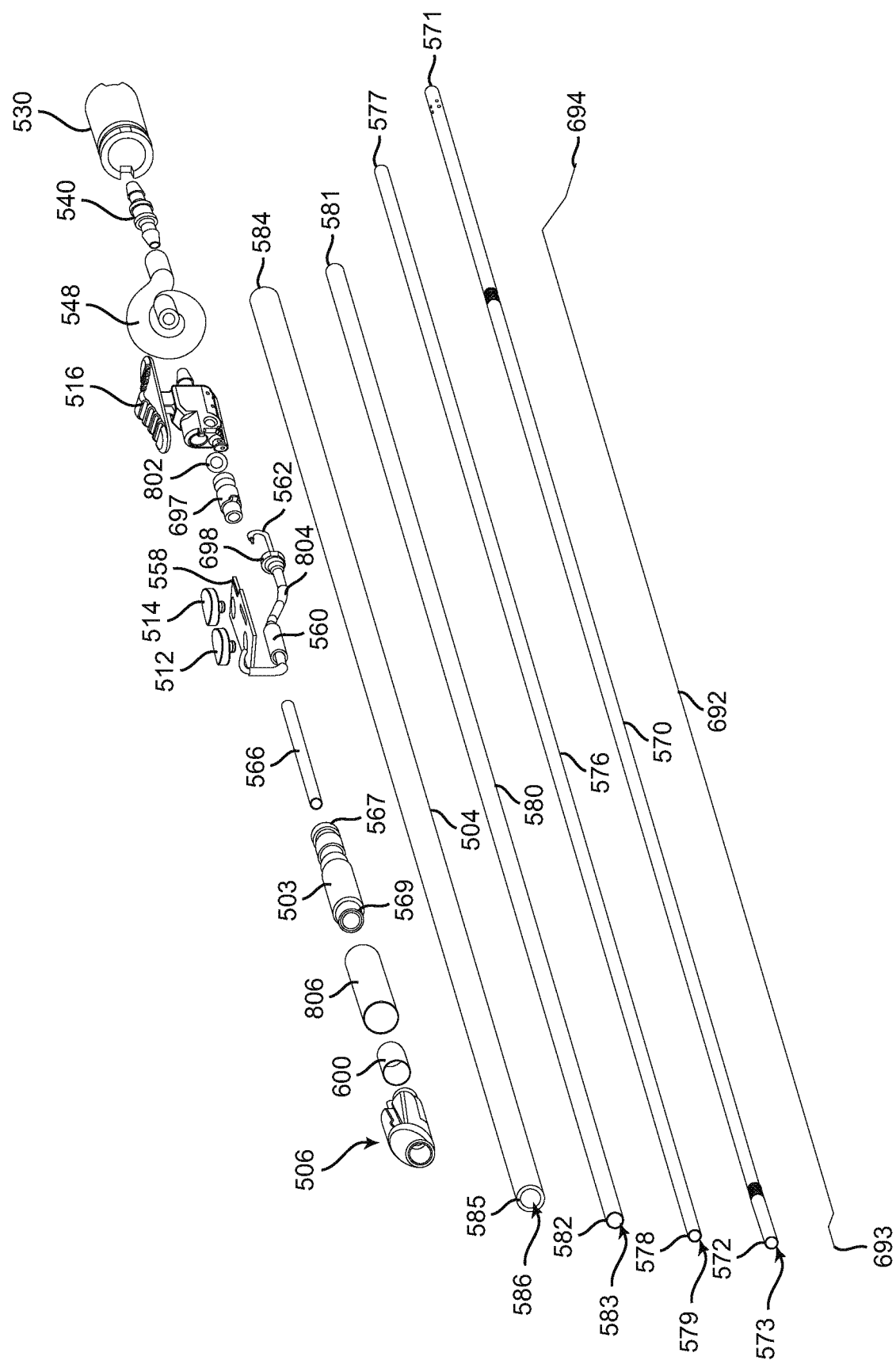

Referring to FIGS. 13A and 13B exploded perspective views of several components of apparatus 500 are shown in accordance with the present disclosure. As shown in FIGS. 13A and 13B, in addition to the components described above, apparatus 500 also includes fitting 540, flexible tube 548, O-ring 802, coupling component 697, printed circuit board (PCB) 558, cable 562, heat shrink component 698, heat shrinks 804, 560, 566, 576, 806, 600, wire 692, flexible conductive gas flow tube 570, and flexible flow tube conduit 580. It is to be appreciated that the components of apparatus 500 shown in FIGS. 13A and 13B will be described in greater detail below.

Figure 13C:
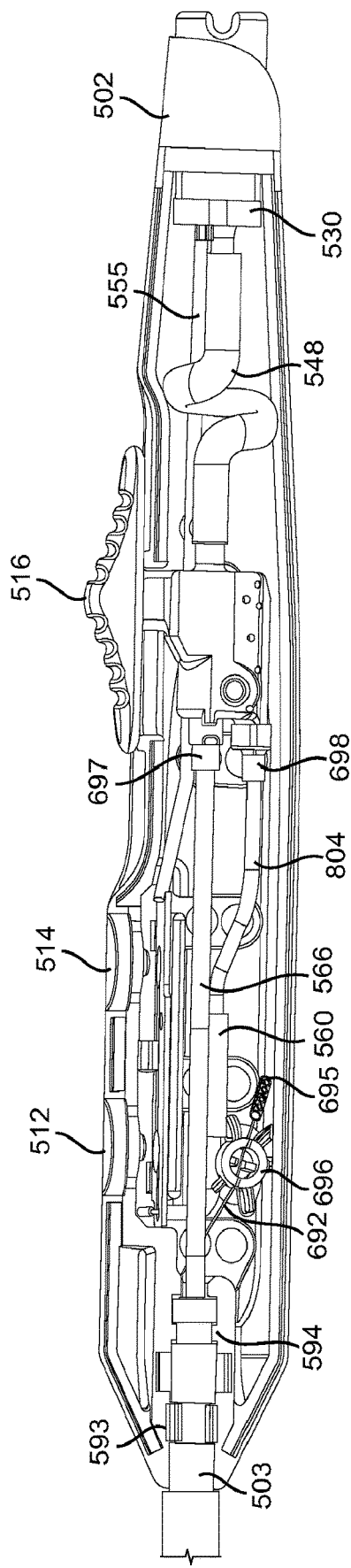
FIG. 13C is a partial side view of the electrosurgical apparatus of FIG. 11A with a portion of the housing removed in accordance with the present disclosure.
Figure 13D:
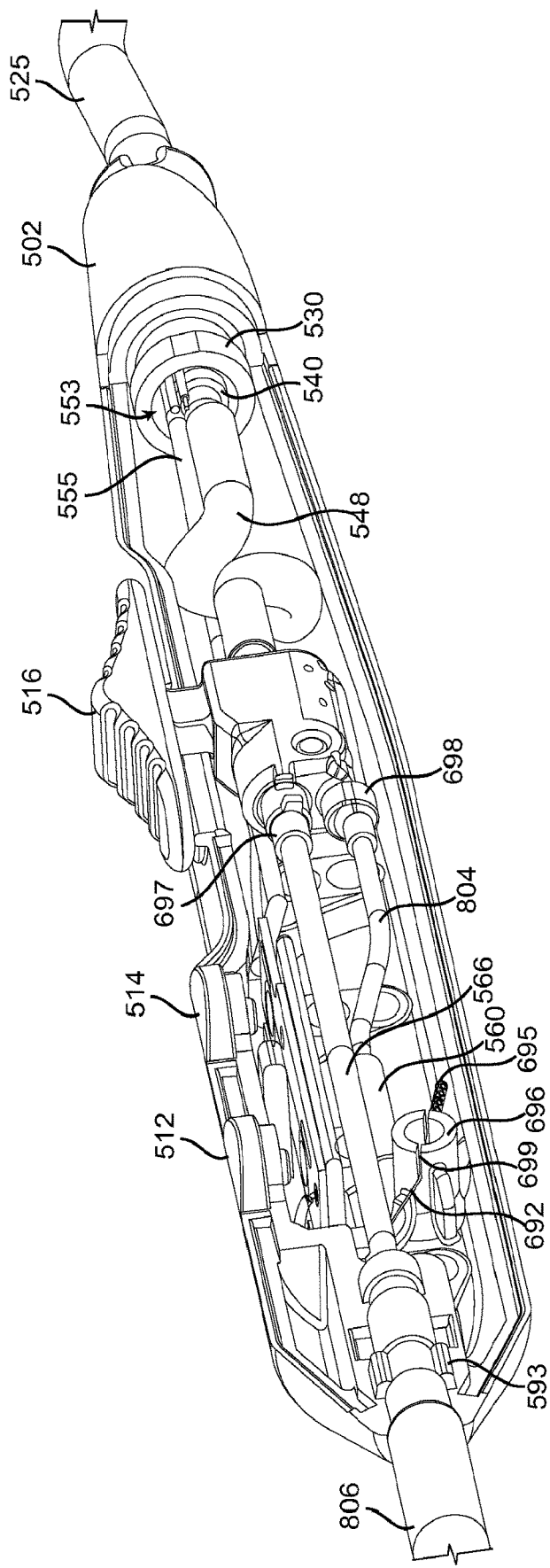
FIG. 13D is a partial perspective view of the electrosurgical apparatus of FIG. 11A with a portion of the housing removed in accordance with the present disclosure.

Referring to FIGS. 13C and 13D, a partial side view of apparatus 500 with a portion of housing 502 removed is shown in FIG. 13C and a partial perspective view of apparatus 500 with a portion of housing 502 removed is shown in FIG. 13D in accordance with the present disclosure. As shown in FIG. 13D, a distal end 553 of cable 525 is disposed through channel 531 of sleeve 530. A flexible gas tube 556 (shown in FIG. 13E) of cable 525 is coupled to fitting 540.

Figure 13E:
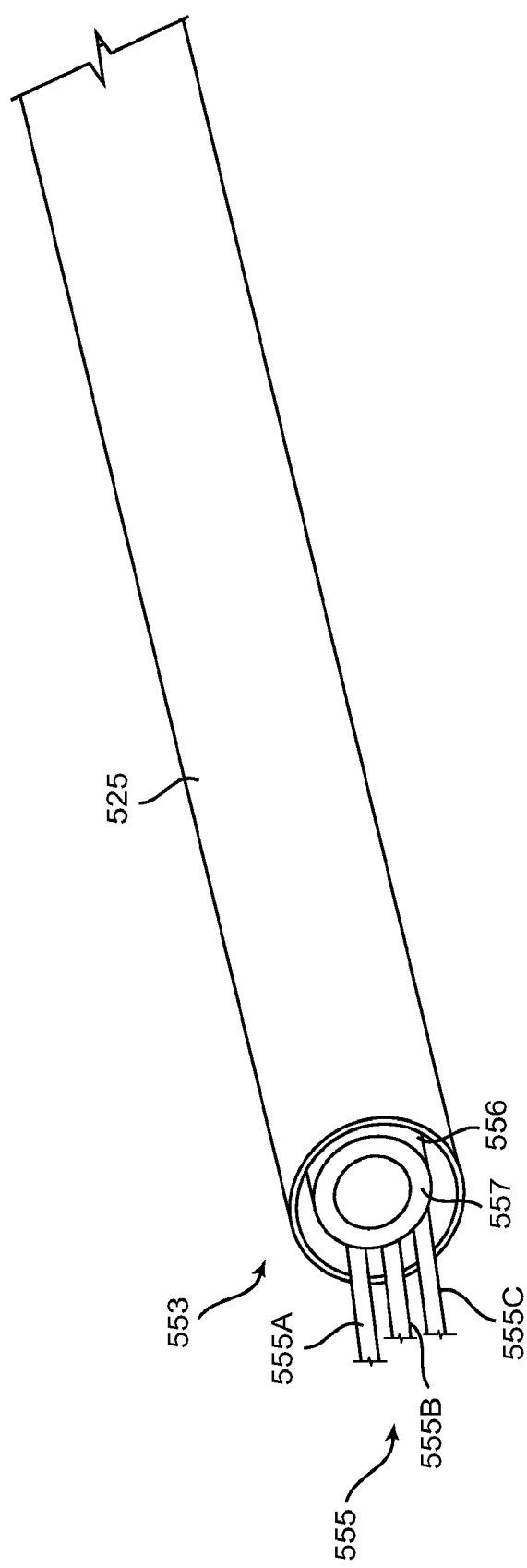
FIG. 13E is a partial perspective view of a cable of the electrosurgical apparatus of FIG. 11A in accordance with the present disclosure.

Referring to FIG. 13E, a perspective view of distal portion 553 of cable 525 is shown in accordance with the present disclosure. As shown in FIG. 13E, in one embodiment, cable 525 includes a flexible gas tube 556, where gas tube 556 includes a channel 554. Although not shown, in one embodiment, connector 523 is configured to be coupled to a gas supply, where connector 523 provides gas from the gas supply to apparatus 500 via gas tube 556 in cable 525. Cable 525 also includes a plurality of electrical wires 555, where electrical wires 555 are coupled to connector 523 and several other components of apparatus 500, as will be described in greater detail below. Although three electrical wires 555A, 555B, 555C are shown, it is to be appreciated that cable 525 may include any number of electrical wires as needed. It is to be appreciated that connector 523 may further be coupled to an electrosurgical generator, such as ESU 12 to provide power to apparatus 500 via wires 555. In one embodiment, the gas supply may be included in the electrosurgical generator.

Figure 13F:
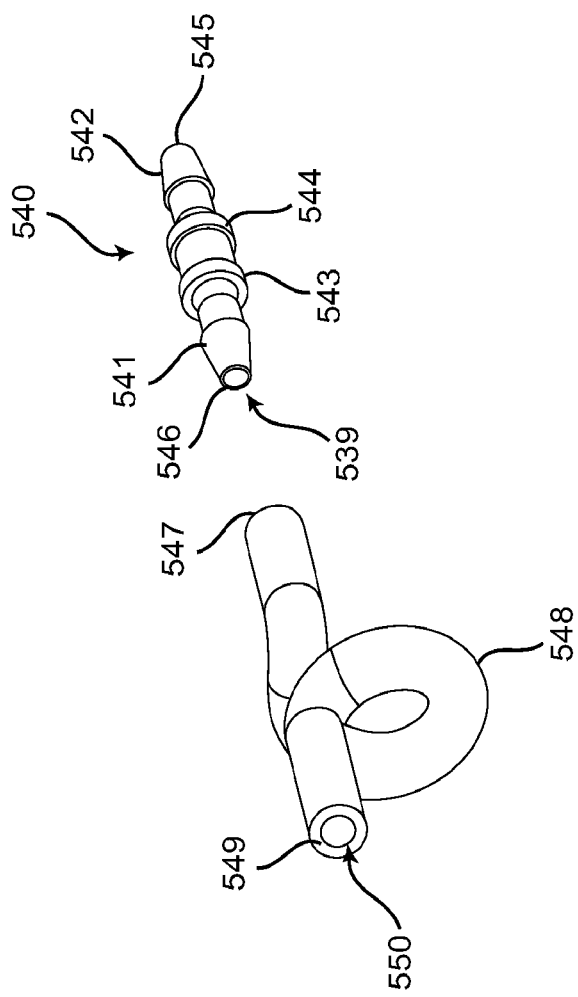
FIGS. 13F and 13G are perspective views of a fitting and a coil tube of the electrosurgical apparatus of FIG. 11A in accordance with the present disclosure.
Figure 13G:
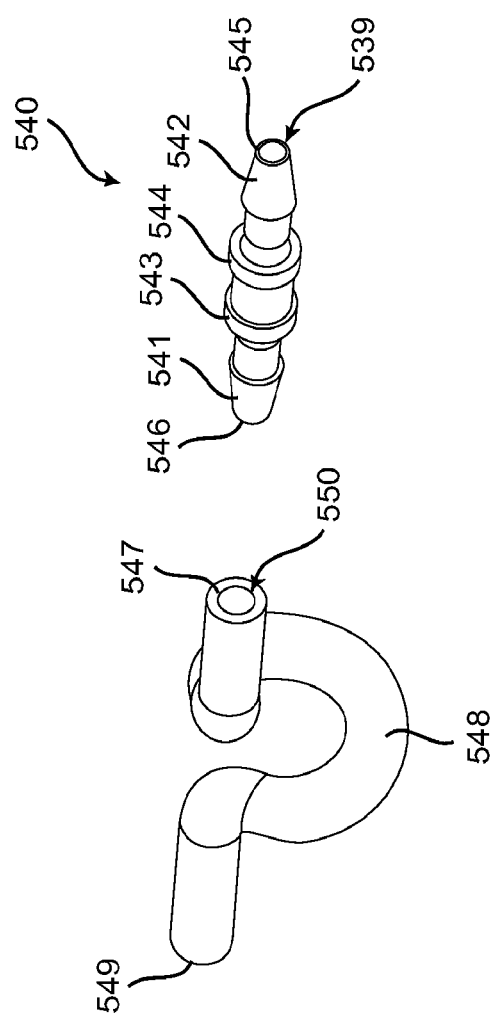

A distal end 557 of gas tube 556 is coupled to a fitting 540, where fitting 540 is also coupled to a flexible coil gas flow tube 548. Referring to FIGS. 13F and 13G, perspective views of fitting 540 and tube 548 are shown in accordance with the present disclosure. As shown in FIGS. 13F and 13G, fitting 540 includes a distal male member 541 disposed on distal end 546 of fitting 540 and a proximal male member 542 disposed on proximal end 545 of fitting 540. Fitting 540 includes a channel 539 extending from proximal end 545 of fitting 540 to distal end 546 of fitting 540. Furthermore, fitting 540 includes tabs 543 and 544. Tube 548 includes a proximal end 547 and a distal end 549 and a channel 550 extending from proximal end 547 to distal end 549.

Proximal male member 542 of fitting 540 is coupled to the distal end 557 of tube 556, such that proximal male member 542 is disposed in distal end 557 of channel 554 of tube 556. When proximal male member 542 is coupled to tube 556, distal end 557 of tube 556 meets tab stopper 544 of fitting 540, preventing tube 556 from advancing past tab stopper 544. It is to be appreciated that proximal male member 542 is generally cone-shaped to prevent proximal male member 542 from being easily removed from channel 554 of tube 556 after being inserted into tube 556.

Distal male member 541 of fitting 540 is coupled to proximal end 547 of tube 548, such that distal male member 541 is disposed in proximal end 547 of channel 550 of tube 548. When distal male member 541 is coupled to tube 548, proximal end 547 of tube 548 meets tab stopper 543 of fitting 540, preventing tube 556 from advancing past tab stopper 543. It is to be appreciated that distal male member 541 is generally cone-shaped to prevent distal male member 541 from being easily removed from channel 550 of tube 548 after being inserted into tube 548. Distal end 549 of tube 548 is coupled to male member 538 (best seen in FIG. 12D) of slider 516, such that male member 538 is disposed in distal end 549 of channel 550 of tube 548. It is to be appreciated that male member 538 is generally cone-shaped to prevent male member 538 from being easily removed from channel 550 of tube 548 after being inserted into tube 548.

Figure 13I:
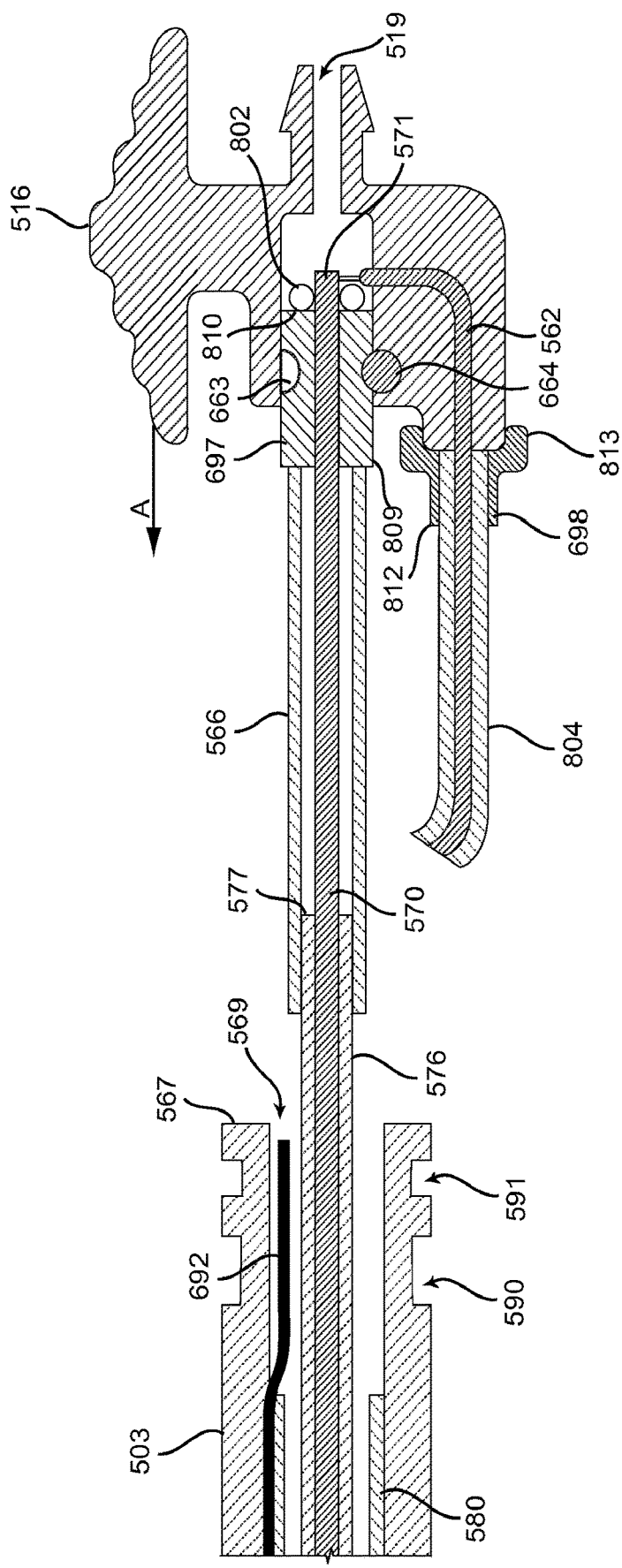
FIG. 13I is a side cross-sectional view of several internal components of the electrosurgical apparatus of FIG. 11A in accordance with the present disclosure.

Slider 516 is further coupled to each of components 697 and 698. Referring to FIG. 13H, perspective views of components 697 and 698 and a dowel 664 are shown in accordance with the present disclosure. Component 697 includes distal end 809 and proximal end 810, where a channel 811 extends from end 809 to end 810 of component 697. Proximal end 810 of component 697 is received by female member 537 of slider 516 such that proximal end 810 of component 697 is disposed through channel 519 (as best seen in FIGS. 13D and 13I). Component 697 also includes a concave circular groove 663 disposed around the cylindrical exterior surface 559 of component 697. Dowel 664 is configured to be disposed in channel 662 of slider 516, such that, a portion of the exterior surface 665 of dowel 664 is received by groove 663 of component 697 to rotatably retain component 697 within channel 519 of slider 516 (as best seen in FIG. 13I).

Component 698 includes distal end 812 and proximal end 813, where a channel 814 extends from end 812 to end 813 of component 698. Proximal end 813 is configured as a female member to receive male member 801 of slider 516 (shown in FIG. 12C). In this way, proximal end 813 of component 698 is configured to be coupled to slider 516 such that proximal end 813 of component 698 is disposed over male member 801 of slider 516 (as best seen in FIGS. 13D and 13I). It is to be appreciated that when end 813 of component 698 is disposed over male member 801, channels 814 and 803 align and are coaxial.

Referring again to FIGS. 13A and 13B, wire 692, flexible conductive gas flow tube 570, flexible heat shrink or wrap 576, flexible gas flow tube conduit 580, and flexible outer insulating tube 504 are shown in accordance with the present disclosure. Wire 692 includes a proximal end 693 and a distal end 694. Flexible conductive gas flow tube 570 includes a proximal end 571 and a distal end 572, where a hollow channel 573 of tube 570 extends from end 571 to end 572 of tube 570. Although not shown, in one embodiment, flexible conductive gas flow tube 570 includes a plurality of laser cuts (similar to laser cuts 401, described above) disposed throughout tube 570 that enable tube 570 to be flexible while being made of a conductive material, such as, but not limited to stainless steel. In one embodiment, tube 570 is made of 304 stainless steel. In another embodiment, at least some of tube 570 is configured as a conductive spring including a plurality of turns or coils (similar to spring 348 described above), such that tube 570 is flexible while also being conductive. In this embodiment, the coils or turns of the spring are wound tightly to minimize leakage.

Flexible heat shrink 576 includes a proximal end 577 and a distal end 578, where a hollow channel 579 of heat shrink 576 extends from end 577 to end 578 of heat shrink 576. Flexible gas flow tube conduit 580 includes a proximal end 581 and a distal end 582, where a hollow channel 583 of gas flow tube conduit 580 extends from end 581 to end 582. Outer flexible tube 504 includes a proximal end 584 and a distal end 585, where a hollow channel 586 of outer flexible tube 504 extends from end 584 to end 585 of outer flexible tube 504. As will be described in greater detail below wire 692, tube 570, heat shrink 576, and conduit 580 are each disposed through channel 586 of outer tube 504.

Referring to FIG. 13I, a partial side cross-sectional view of some of the components of apparatus 500 is shown in accordance with the present disclosure. As shown in FIG. 13I, a portion of proximal end 571 of gas flow tube 570 is disposed through channel 811 of component 697 and channel 519 of slider 516. It is to be appreciated that component 697 is rotatably disposed in channel 519 of female member 537 of slider 516 and gas flow tube 570 is fixedly coupled to component 697, such that, when slider 516 is advanced in a distal direction A toward end 521 of slot 522, gas flow tube 570 is also advanced in a distal direction A. Similarly, if slider 516 is retracted in a proximal direction opposite to direction A toward end 524 of slot 522, gas flow tube 570 is also retracted in a proximal direction opposite to A. Furthermore, because component 697 is rotatable within channel 519, gas flow tube 570 is also rotatable, thus preventing gas flow tube 570 from becoming twisted if rotated while apparatus 500 is in use. As will be described in greater detail below, distal end 572 of gas flow tube 570 is coupled to an electrosurgical electrode 518 that is also advanced and retracted by the movement of flow tube 570.

In one embodiment, heat shrink tubing 566 and 576 are disposed over gas flow tube 570. Gas flow tube 570 is fixedly coupled to heat shrink 576, such that, at least a portion of flexible tube 570 is disposed in channel 579 of heat shrink 576 and the exterior surface of flexible tube 570 is in contact with the interior surface of heat shrink 576. Also, in one embodiment, heat shrink 566 and 576 overlap. In this embodiment, heat shrink 566 is fixedly coupled to heat shrink 576, such that, at least a portion of heat shrink 576 is disposed in the hollow interior of heat shrink 566 and the exterior surface of heat shrink 576 is in contact with the interior surface of heat shrink 566. It is to be appreciated that when slider 516 is advanced in a direction A or retracted in a direction opposite to direction A, heat shrinks 566, 576 and gas flow tube 570 are each extended or retracted in unison.

It is to be appreciated that gas provided via connector 523 through channel 554 of cable 525, channel 539 of fitting 540, channel 550 of coil 548, and through channel 519 of slider 516 flows into channel 573 of flexible conductive gas flow tube 570. As stated above, in one embodiment, flexible conductive gas flow tube 570 includes a plurality of laser cuts that enable tube 570 to be flexible. In another embodiment, flexible conductive gas flow tube 570 is configured as a flexible conductive spring with a plurality of coils or turns. In either embodiment, the laser cuts, coils or turns may allow some of the gas provided to channel 573 of flexible conductive gas flow tube 570 to escape through the laser cuts or coils/turns. Heat shrinks 566, 576 are configured to trap or contain any gas escaping from the laser cuts or coils/turns of tube 570. In this way, any gas escaping from the laser cuts or coils/turns of tube 570 does not escape into other portions of apparatus 500. In one embodiment, heat shrinks 566, 576 may be configured as a single heat shrink. In one embodiment, O-ring 802 is disposed over distal end 571 of tube 570 to prevent the backflow of gas into channel 519.

As seen in FIG. 13I, a cable 562, including one or more electrical wires, is disposed through channel 814 of component 698 and channel 803 of slider 516 and coupled to the proximal end 571 of tube 570. In one embodiment, cable 562 is coupled to proximal end 571 of tube 570 via a lead that is soldered to a collet in channel 519 of slider 516, where the collet is coupled to tube 570.

In one embodiment, heat shrink 804 is disposed over cable 562. Furthermore, cable 562 and heat shrink 804 may be disposed through heath shrink tubing 560.

Figure 13J:
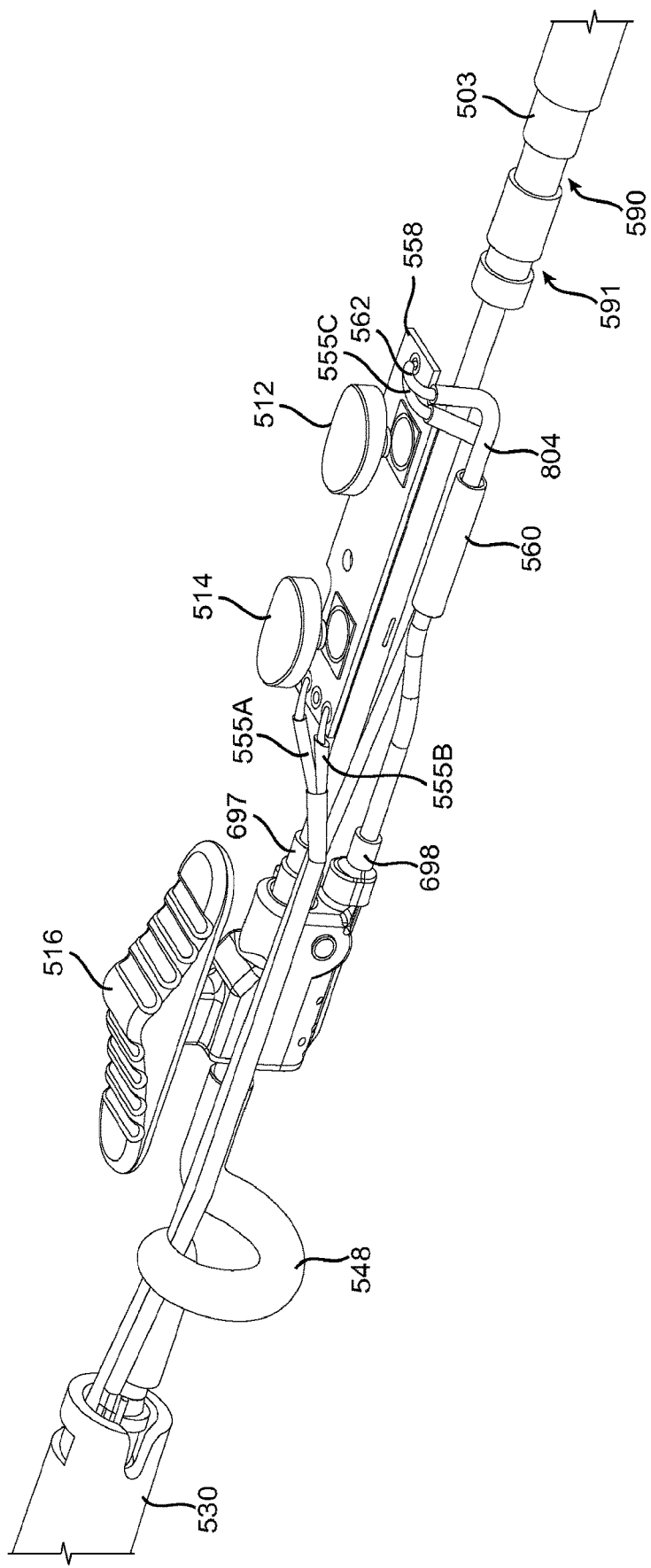
FIG. 13J is a perspective view of several components of the electrosurgical apparatus of FIG. 11A in accordance with the present disclosure.

Referring to FIG. 13J, cable 562 is coupled to PCB 558. PCB 558 is also coupled to wires 555A, 555B, 555C of cable 525. In one embodiment, wire 555A is coupled to a receptacle of PCB 558 associated with button 514, wire 555B is coupled to a receptacle of PCB 558 associated with button 512, and wire 555C is coupled to cable 562. Wire 555C is configured receive electrosurgical energy via a power source (e.g., ESU 12) and provide the received electrosurgical energy to cable 562, where the electrosurgical energy is further provided to tube 570. Wires 555A and 555B are configured to transmit signals associated with buttons 514, 512, respectively. When either button 512 or button 514 are pressed, projections 513 and/or 515 come into contact with PCB 558. When projections 513 and/or 515 come into contact with PCB 558, communication signals are provided via wires 555A and 555B to the power source coupled to electrosurgical apparatus 500 via cable 525 and connector 523. In response, to the communication signals provided via wires 555A and 555B, the power source is configured to provide electrosurgical energy to tube 570 via wire 555C and cable 652. Buttons 512, 514 are each configured with different surgical modes for apparatus 500. In one embodiment, button 512 is configured to control J-Plasma or cold plasma activation and button 514 is configured to control monopolar coagulation for apparatus 500.

In another embodiment, buttons 512 and 514 and wires 555A and 555B are removed from apparatus 500 and one or more foot pedals or switches 852, 854 are configured to control the electrosurgical energy provided to tube 570 and perform the functions of buttons 512 and 514. As described above, the foot switches 852, 854 may be coupled to a power source or ESU, such as ESU 12. When either of foot switches 852, 854 are pressed by a user, communication signals are sent from the foot switches 852, 854 to ESU 12 to modify the waveform and/or change the properties of the electrosurgical energy provide to electrode 518 as necessary based on the desired mode of operation for apparatus 500 (e.g., coagulation, fulguration, ablation, etc.)

Figure 13K:
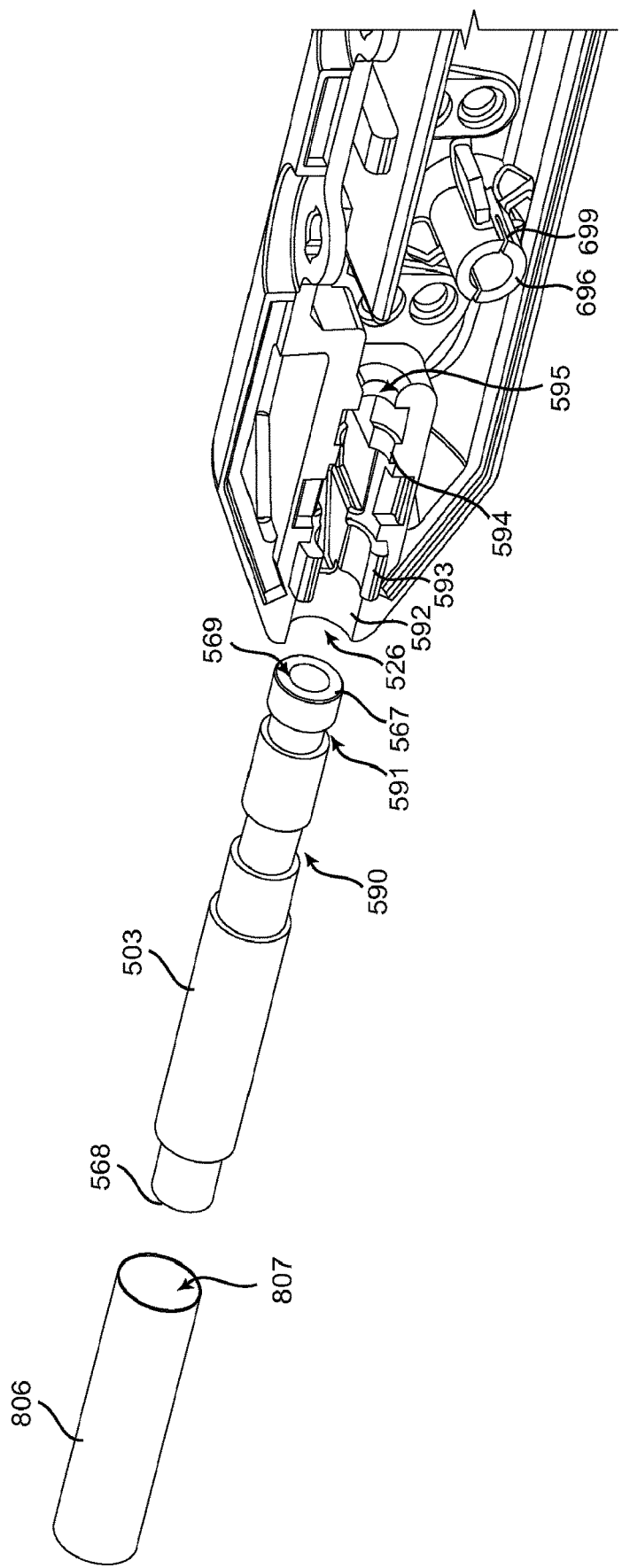
FIG. 13K is a side perspective view of a rigid shaft and a proximal portion of the housing of the electrosurgical apparatus of FIG. 11A in accordance with the present disclosure.
Figure 13L:
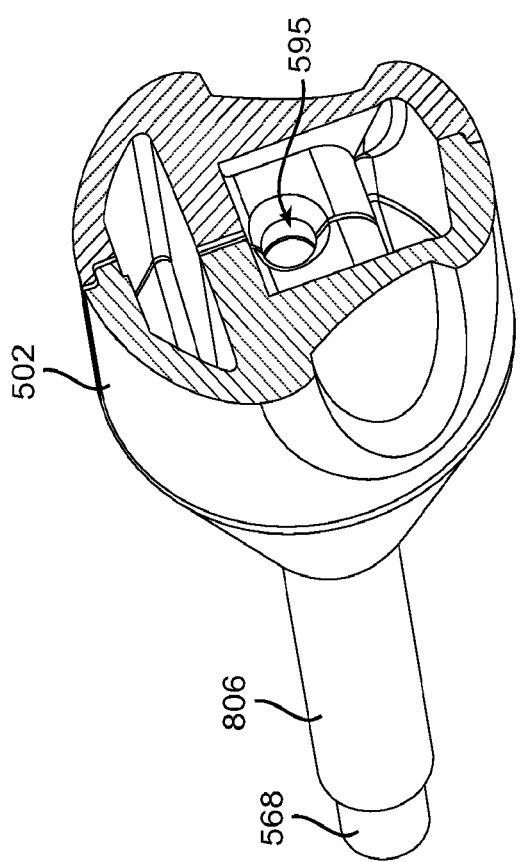
FIG. 13L is a cross-sectional perspective view of the rigid shaft of FIG. 13I and a proximal portion of the housing of the electrosurgical apparatus of FIG. 11A in accordance with the present disclosure.

Referring again to FIG. 13I, tube 570 and heat shrink 576 are disposed through channel 569 of rigid shaft 503 and through channel 583 of gas flow tube conduit 580. As shown in FIGS. 13C and 13D, rigid shaft 503 is coupled to a distal end 528 of housing 502 where, proximal end 567 of rigid shaft 503 is disposed in channel 526 of housing 502. Referring to FIG. 13K, a perspective view of rigid shaft 503 and a portion of housing 502 is shown in accordance with the present disclosure. As shown in FIG. 13K, channel 526 includes tabs 593 and 594 disposed on and protruding from an interior surface 592 of channel 526. Furthermore, shaft 503 includes circular slots 590 and 591 disposed around the cylindrical exterior of rigid shaft 503. Channel 526 includes an aperture 595. Tabs 593 and 594 are configured to be disposed in slots 590 and 591, respectively, when the proximal end 567 of shaft 503 is disposed in channel 526. Tabs 593 and 594 and slots 590 and 591 are configured to rotatably retain rigid shaft 503 in channel 526. When proximal end 567 of rigid shaft 503 is disposed in channel 526 of housing 502, the proximal end 567 of channel 569 is aligned with aperture 595 of channel 526 of housing 502. Referring to FIG. 13L, a cross-sectional perspective view of housing 502 is shown in accordance with the present disclosure, where aperture 595 can be seen. It is to be appreciated that heat shrink 576 and tube 570 are disposed through aperture 595.

As shown in FIG. 13k, in one embodiment, apparatus 500 includes a heat shrink 806. Heat shrink 806 includes a channel 807, where a portion of rigid shaft 503 protruding from housing 502 is configured to be disposed through channel 807 of heat shrink 806. Heat shrink 806 is best seen disposed over rigid shaft 503 in FIGS. 13D and 13L.

Figure 13M:
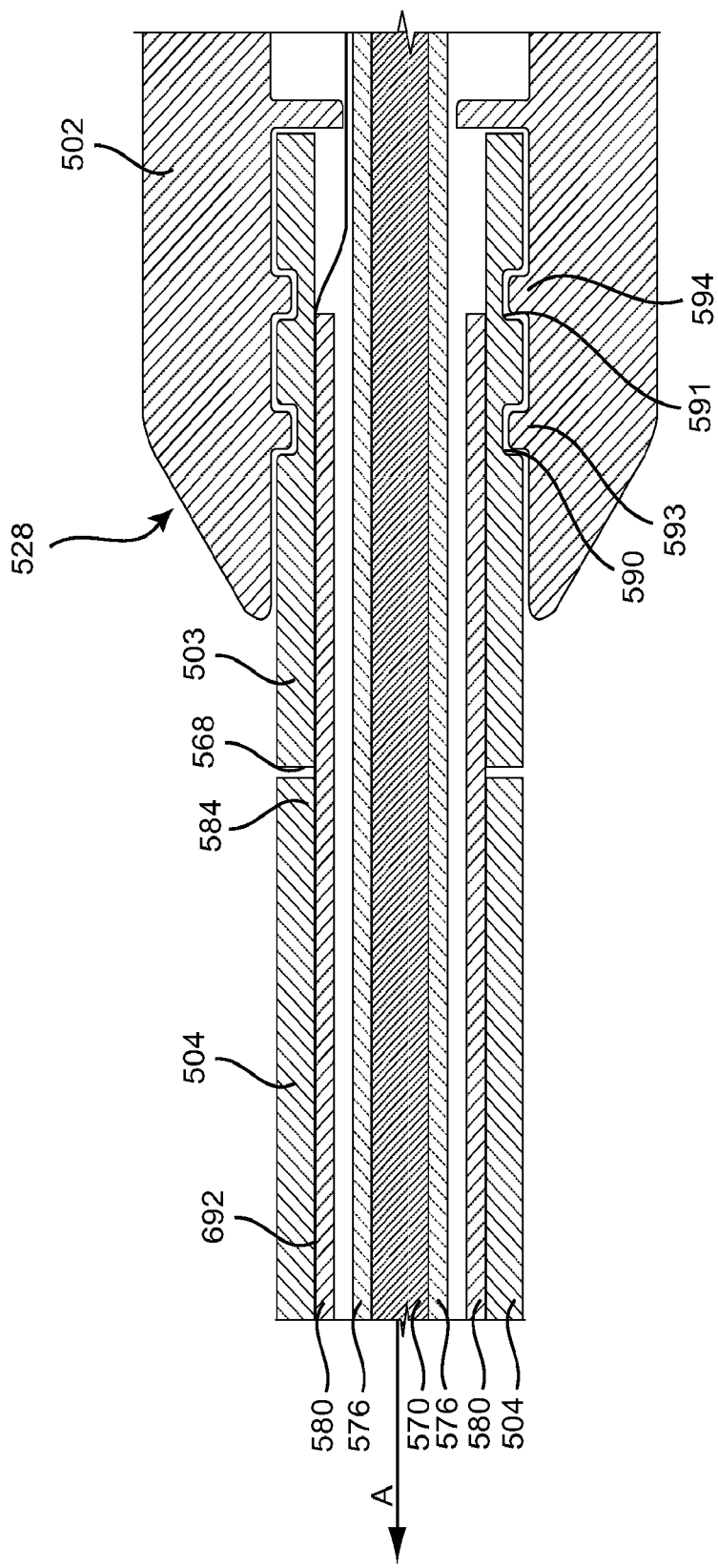
FIG. 13M is a partial cross-sectional view of the electrosurgical apparatus of FIG. 11A in accordance with the present disclosure.

It is to be appreciated that gas flow tube conduit 580, heat shrink 576, and gas flow tube 570 are disposed through channel 586 of outer tube 504. For example, referring now to FIG. 13M, another partial side cross-sectional view of apparatus 500 is shown in accordance with the present disclosure. As seen in FIG. 13M, distal end 568 of rigid shaft 503 is coupled to proximal end 584 of outer tube 504. Gas flow tube conduit 580 is fixedly coupled to the interior surfaces of channels 569 and 586 (shown in FIG. 13A) of rigid shaft 503 and conduit 580, respectively. Gas flow tube conduit 580 is made of an insulative material, such as but not limited to Teflon. In one embodiment, the inner walls of conduit 580 are configured with a lubricious material or coating to aid in the sliding of tube 570 and heat shrink 576 within conduit 580 and outer tube 504. As stated above, distal portion 585 of outer tube 504 is coupled to tip 506. Gas flow tube conduit 580, heat shrink 576, and tube 570 each extend through channel 586 of outer tube 504 to the interior of tip 506, as will be described in greater detail below.

Additionally, flexible wire 692 (shown in FIG. 13A) extends through channel 586 of outer tube 504, such that distal end 694 of wire 692 is coupled to tip 506 and proximal end 693 of wire 692 is coupled to the interior of housing 502. As shown in FIGS. 13I and 13M, in one embodiment, wire 692 is fixedly disposed between conduit 580 and shaft 503 and conduit 580 and outer tube 504. Referring to FIGS. 13C, 13D, and 13K, the interior of housing 502 includes an extension member 696 that extends from an inner wall of housing 502. Extension member 696 includes a slot 699 configured to receive proximal end 693 of wire 692. In one embodiment, a securing member (e.g., a ferrule) 695 is disposed on the proximal end 693 of wire 692 to retain wire 692 in slot 699 of extension member 696. As will be described in greater detail below, wire 692 is configured to provide structural integrity to tip 506 when blade 518 is used for cutting during surgery. Furthermore, wire 692 is configured to prevent outer tube 504 from stretching when tip 506 is pulled away from housing 502.

Referring again to FIG. 13M, tube 570 and heat shrink 576 are configured to be slidable within channel 583 of conduit 580. As seen in FIG. 13M, although heat shrink 576 is fixedly coupled to and disposed around tube 570, and tube 504 is fixedly coupled to and disposed around gas flow tube conduit 580, gas flow tube conduit 580 is not fixedly coupled to heat shrink 576. In this way, when heat shrink 576 and gas tube 570 are extended in a direction A (indicated in FIG. 13M) or retracted in a direction opposite to A within outer tube 504 and gas flow tube conduit 580, outer tube 504 and gas flow tube conduit 580 remain stationary in relation to tube 570 and heat shrink 576.

As stated above, outer tube 504, gas flow tube conduit 580, heat shrink 576, and tube 570 are each configured to be flexible. In this way, tip 506 of apparatus 500 can be manipulated (e.g., using a device such as forceps 900) to achieve a wide variety of positions in relation to housing 502. Below, tip 506 will be described in greater detail.

Figure 14A:
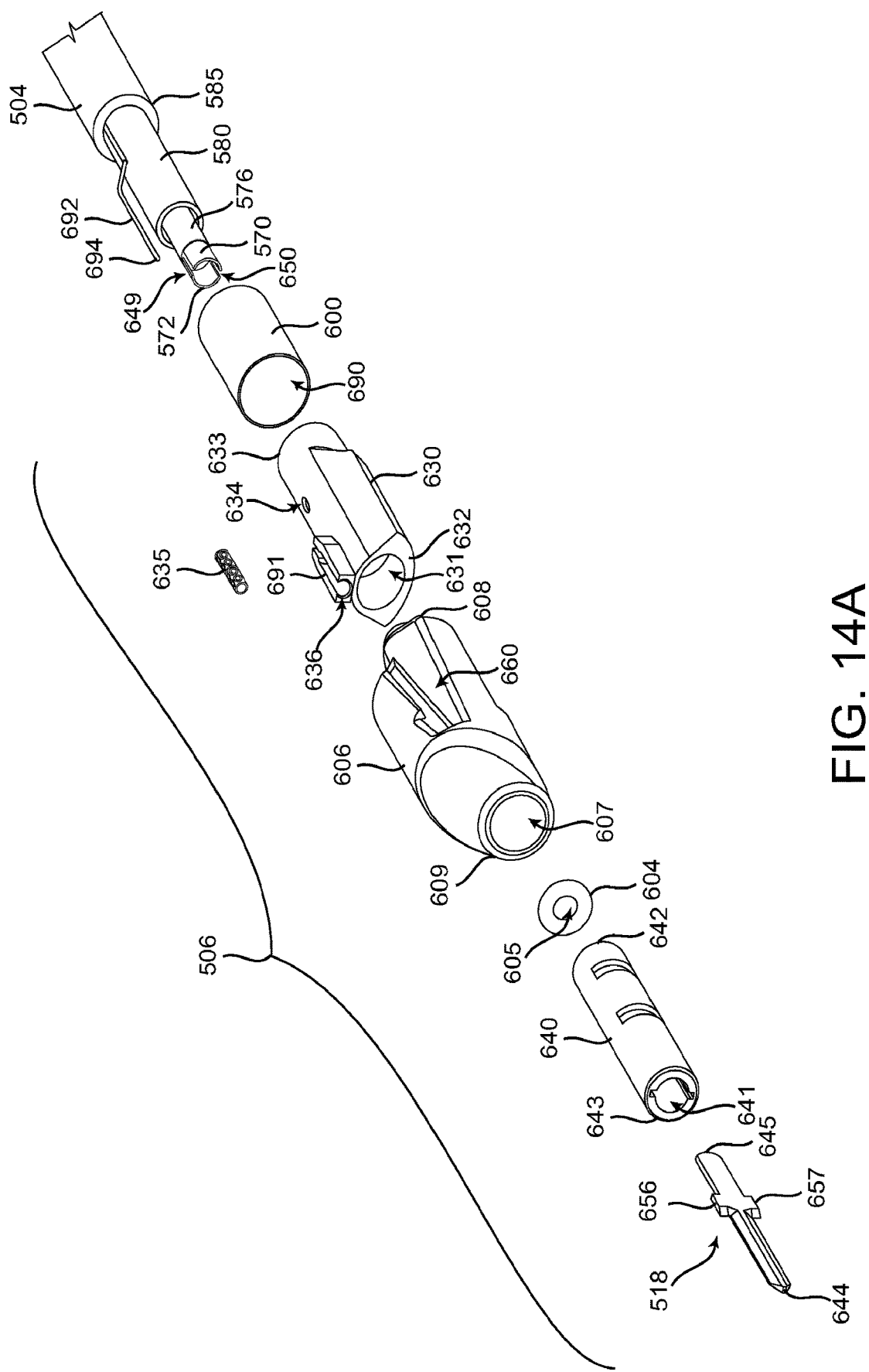
FIGS. 14A and 14B are partial exploded perspective views of the electrosurgical apparatus of FIG. 11A in accordance with the present disclosure.
Figure 14B:
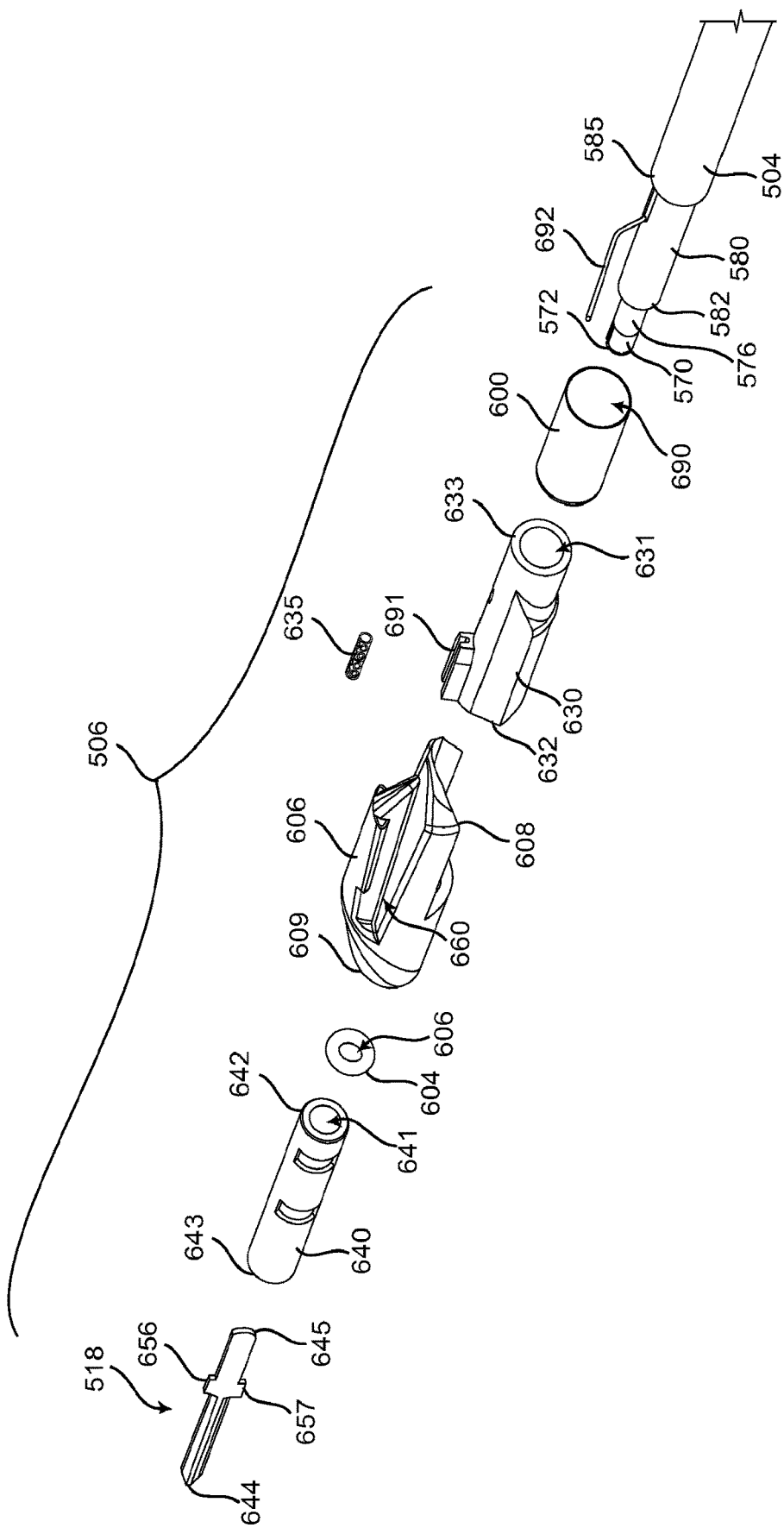

Referring now to FIGS. 14A and 14B, exploded perspective views of distal tip assembly 506 and the distal ends of outer tube 504, wire 692, gas flow tube conduit 580, heat shrink 576, tube 570 are shown in accordance with the present disclosure. As shown in FIGS. 14A and 14B, tip 506 includes electrode or blade 518, cylindrical ceramic tip 640, outer tip housing 606, annular O-ring shaped seal 604, inner tip housing 630, ferrule or securing member 635, and heat shrink 600. Ceramic tip 640 includes a channel 641 extending from a distal end 643 to a proximal end 642 of ceramic tip 640. O-ring 604 includes an aperture 605. Outer tip housing 606 includes a channel 607 extending from a distal end 609 toward a proximal end 608 of outer tip housing 606. Inner tip housing 630 includes a channel 631 extending from a distal end 632 of inner tip housing 630 to a proximal end 633 of inner tip housing 630. Inner tip housing 630 further includes an aperture 634 and an extension member 691 disposed on an outer surface of inner tip housing 630, where extension member 691 includes a slot 636. Slot 636 is configured to receive securing member 635. Heat shrink 600 includes a channel 690.

It is to be appreciated that, in one embodiment, outer tip housing 606 and inner tip housing 630 are configured as a single component.

Figure 14C:
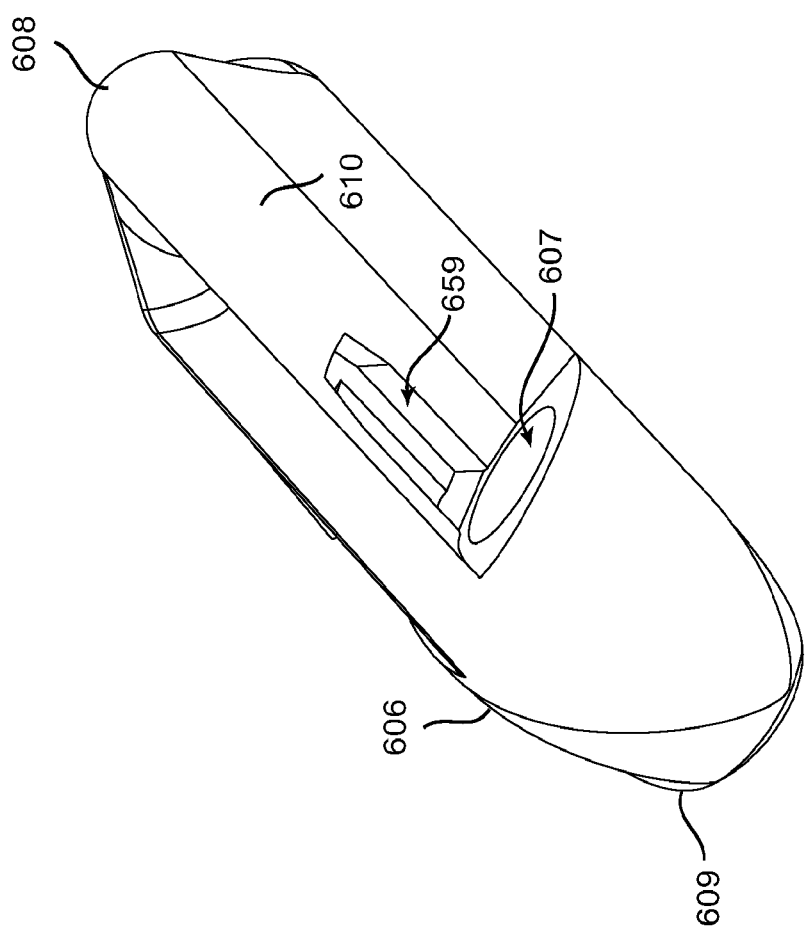
FIG. 14C is a perspective view of an inner housing of the electrosurgical apparatus of FIG. 11A in accordance with the present disclosure.

Proximal end 642 of ceramic tip 640 is disposed in channel 607 of outer tip housing 606. Outer tip housing 606 and inner tip housing 630 are configured to be coupled such that extension member 691 is received by a slot of outer tip housing 606 and channels 607 and 631 align. For example, referring to FIG. 14C a perspective view of outer tip housing 606 is shown in accordance with the present disclosure. As seen in FIG. 14C, outer tip housing includes a slot 659 disposed on an inner surface 610. Slot 659 is configured to receive extension member 691.

Figure 14D:
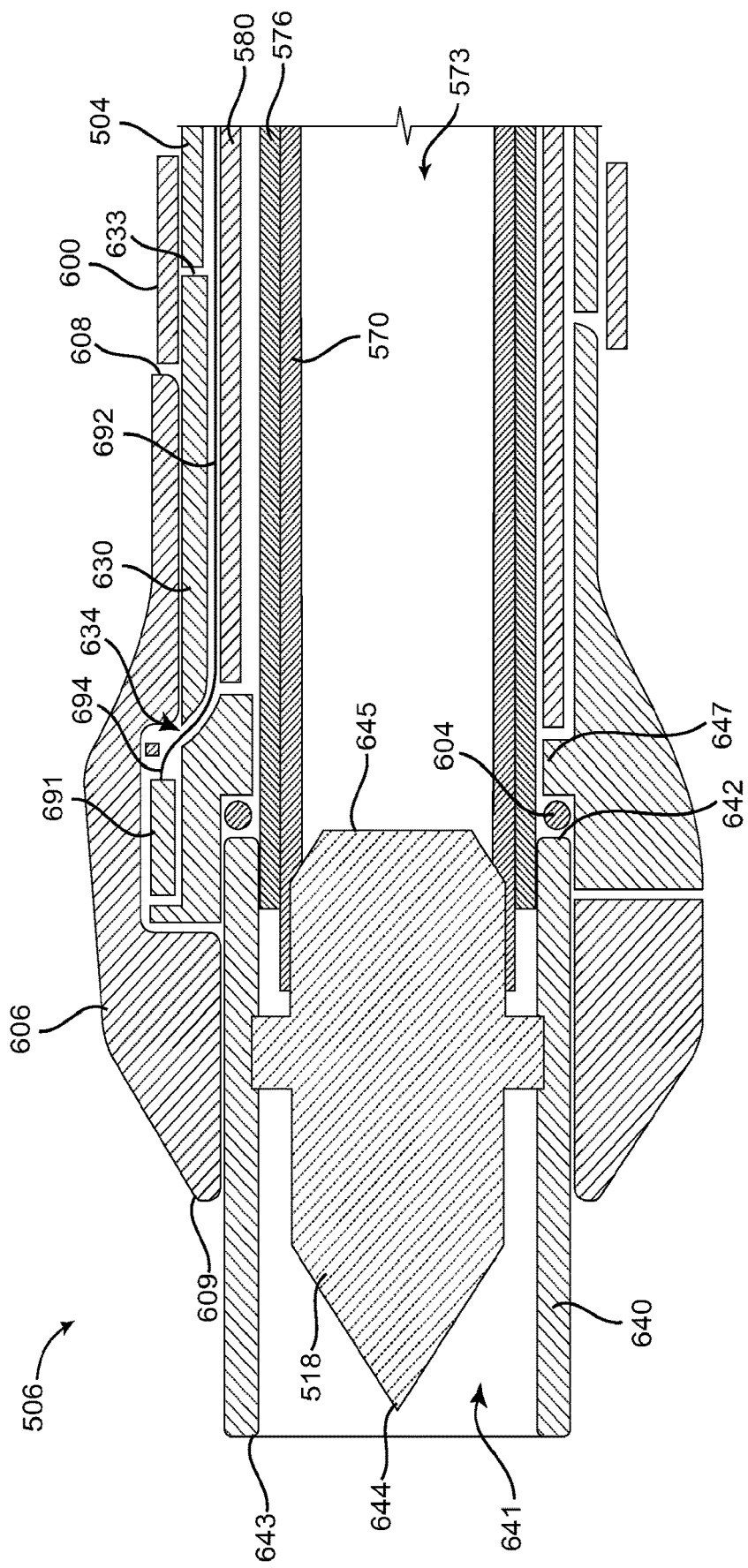
FIG. 14D is a partial cross-sectional view of the electrosurgical apparatus of FIG. 11A in accordance with the present disclosure.

Referring to FIG. 14D, a cross-sectional view of tip 506 of apparatus 500 is shown in accordance with the present disclosure. As shown in FIG. 14D, outer tube 504 is fixedly coupled to the proximal end 633 of inner tip housing 630, such that the distal end 582 of gas flow tube conduit 580, the distal end 694 of wire 692, the distal end 578 of heat shrink 576, and the distal end 572 of gas flow tube 570 are each disposed through channel 631 of inner tip housing 630 and channel 607 of outer tip housing 606. In one embodiment, a heat shrink 600 is disposed over the proximal end 633 of inner tip housing 630 and the distal end 585 of outer tube 504.

It is to be appreciated that distal end 694 of wire 692 disposed through aperture 634 and into slot 659 of inner tip housing 630 and is coupled to securing member 635. As stated above, wire 692 is configured to be secured to each of tip 506 and housing 502 to provide structural integrity to tip 506 when blade 518 is used for cutting during surgery. Furthermore, since wire 692 is inelastic, wire 692 is configured to guarantee the maximum distance of housing 502 from tip 506. In this way, excessive stretching of outer tube 504 is prevented.

As shown in FIG. 14D, the distal ends 572 and 578 of tube 570 and heat shrink 576, respectively, are disposed through the proximal end 642 of channel 641 of ceramic tip 640. A proximal end 645 of blade 518 is disposed through distal end 643 of channel 641 of ceramic tip 640 and fixedly coupled to the distal end 572 of flexible conductive gas flow tube 570. It is to be appreciated that, in one embodiment, the distal end 572 of flexible conductive gas flow tube 570 includes a pair of slits 649, 650 (best seen in FIG. 14A), configured to receive the proximal end 645 of blade 518.

Figure 14E:
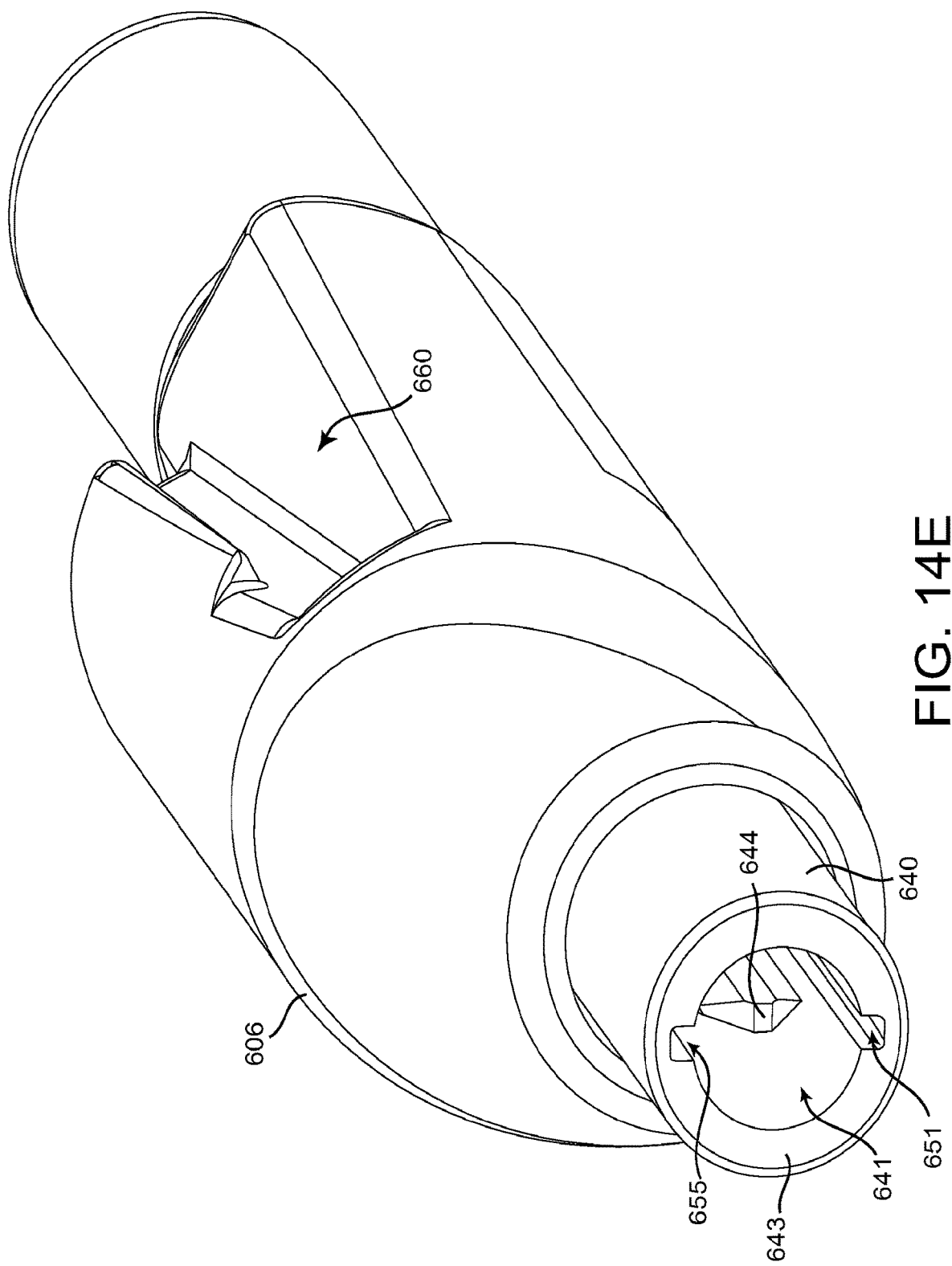
FIGS. 14E, 14F, and 14G are partial perspective views of a distal portion of the electrosurgical apparatus of FIG. 11A in accordance with the present disclosure.
Figure 14F:
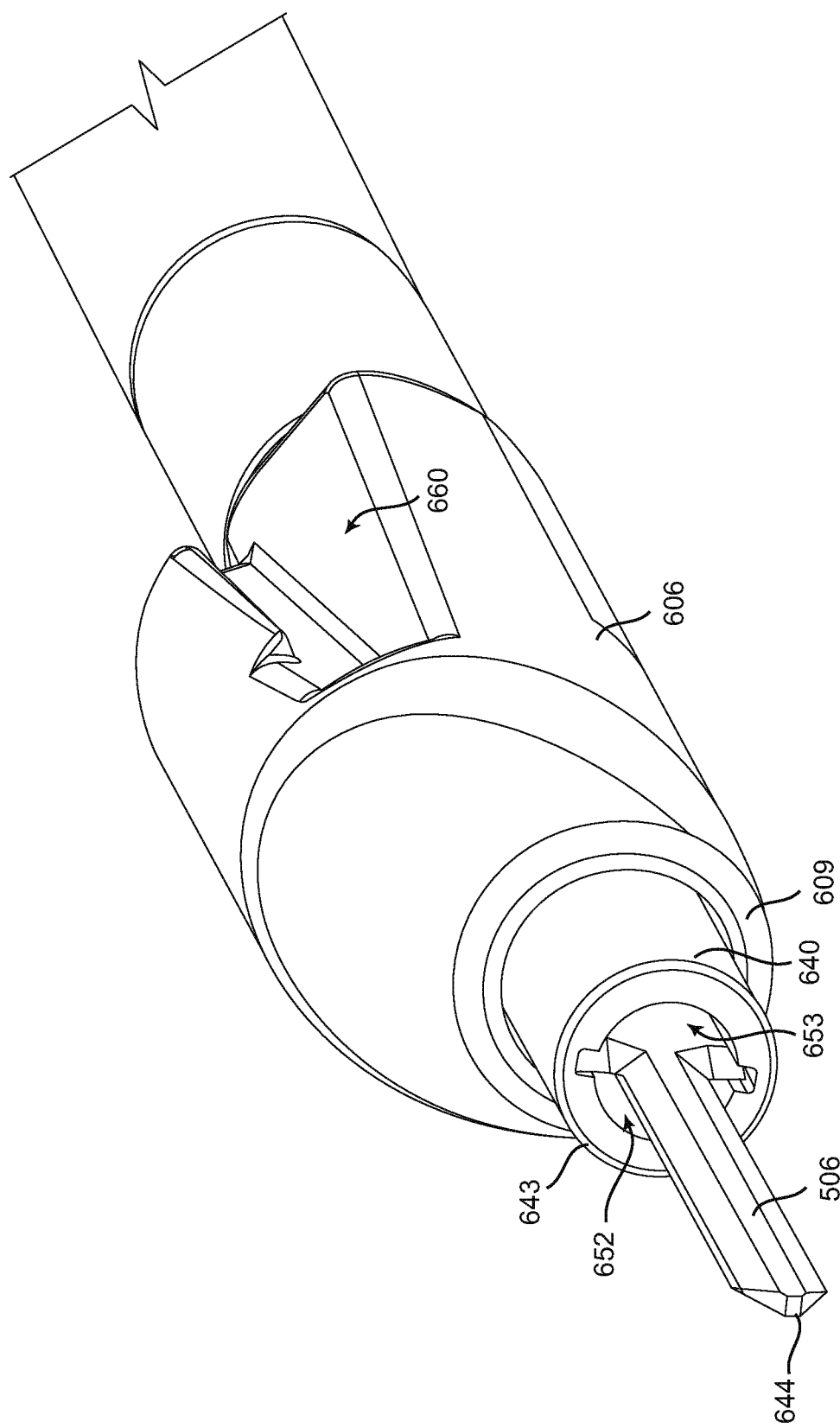
Figure 14G:
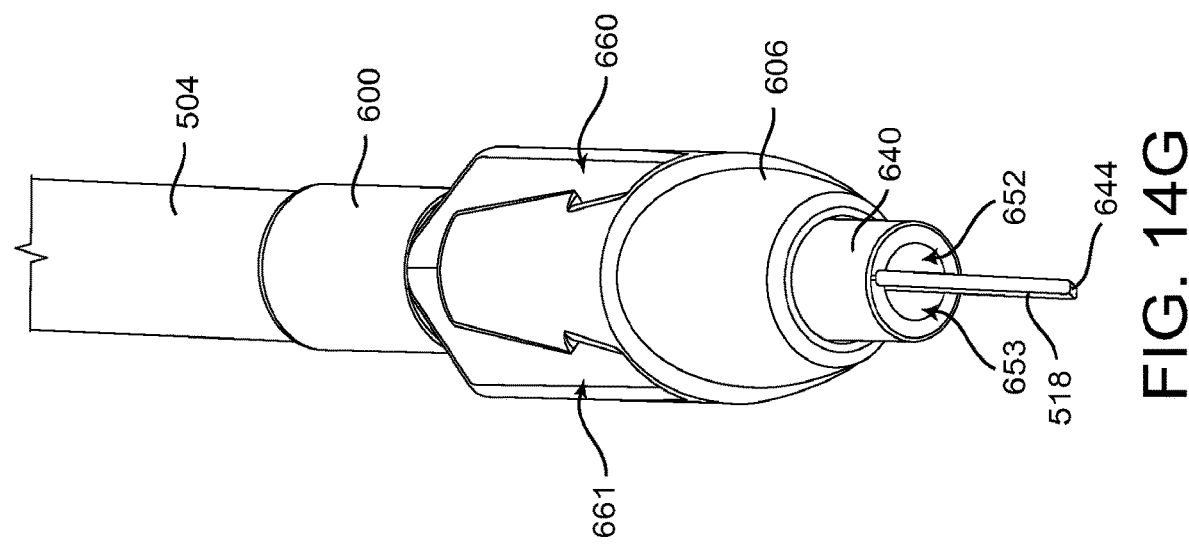

In one embodiment, distal end 643 of channel 641 of ceramic tip 640 is configured to slidably receive blade 518. For example, referring to FIG. 14E, a perspective view of ceramic tip 640 disposed in channel 607 of tip housing 606 is shown in accordance with the present disclosure. As shown in FIG. 14E, the distal end 643 of channel 641 includes diametrically opposed slots 651, 655, which are disposed on an inner circumference of ceramic tip 640 and extend from distal end 643 of ceramic tip 640 toward the proximal end 642 of ceramic insert 640. Slot 651 is configured to receive an extension member 657 (shown in FIGS. 14A, 14B, and 14D) of blade 518 and slot 655 is configured to receive an extension member 656 (shown in FIGS. 14A, 14B, and 14D) of blade 518 to slidably retain blade 518. Referring to FIGS. 14F and 14G, blade 518 is shown in an extended position while being disposed through slots 651, 655 of channel 641. When blade 518 is disposed through slot 651 of channel 641, gas passageways 652 and 653 are formed on each side of blade 518.

It is to be appreciated that ceramic tip 640 is fixedly coupled to outer tip housing 606. In this way, ceramic tip 640 is not rotatable relative to tip housing 606 (and thus distal tip 506). Furthermore, since extensions members 656, 657 are disposed in slots 655, 651 of ceramic tip 640, although blade 518 is slidable distally and proximally relative to ceramic tip 640 and distal tip 506, blade 518 is not rotatable relative to ceramic tip 640 and distal tip 506. In this way, blade 518 rotates with ceramic tip 640 and housing 506.

It is to be appreciated that channels 641, 607, 631 are configured such that heat shrink 572 and flexible conductive gas flow tube 570 may move freely within channels 641, 607, 631 of tip 506. In this way, slider 516 may be advanced distally or retracted proximally to advance or retract flexible conductive gas flow tube 570 and heat shrink 576 to advance or retract blade 518 relative to the distal end of tip 506. For example, when slider 516 is advanced toward end 521 of slot 522, blade 518 is advanced past the distal end 643 of channel 641. Alternatively, when slider 516 is retracted toward end 524 of slot 522, blade 518 is retracted into the interior of channel 641 of ceramic tip 640.

In one embodiment, when an inert gas, such as argon or helium is provided via channel 573 of flexible conductive gas flow tube 570 from a gas supply coupled to apparatus 500 via cable 525 and connector 523, the inert gas will flow through channel 641 and through passageways 652 and 653 over blade 518. When blade 518 is in a retracted position (as shown in FIGS. 14D and 14E), the apparatus 500 is suitable for generating plasma. In the retracted position, RF energy is conducted to distal end 644 of blade 518 via flexible conductive gas flow tube 570 (provided by an electrosurgical generator coupled to apparatus 500 via cable 525 and connector 523). As inert gas is supplied via flexible conductive gas flow tube 570 and flows over blade 518 via passageway 562 and 563, blade 518 is held at high voltage and high frequency to generate a cold plasma beam that is ejected from the distal end of tip 506.

When blade 518 is in an advanced position (i.e., slider 516 is advanced toward end 521 of slot 522 to advance blade 518 past distal end 643 of channel 641), apparatus 500 may be used for two cutting modes: mechanical cutting and electrosurgical cutting. In mechanical cutting mode, RF or electrosurgical energy is not applied to flexible conductive gas flow tube 570 or blade 518, and therefore, the blade 518 is in a de-energized state. In this mode, the blade 518 can be used to excise tissue via mechanical cutting. In electrosurgical cutting mode, the blade 518 is advanced and used both while being electrically energized and enveloped with inert gas flow.

Referring again to FIGS. 14A, 14B, and 14D, O-ring or gas seal 604 is disposed around distal end 578 of heat shrink 576 and distal end 572 of gas flow tube 570. As best seen in FIG. 14D, seal 604 is disposed around heat shrink 576 and tube 570 and between the proximal end 642 of ceramic tip 640 and a spherical tab 647 disposed within the inner surface of channel 631 of inner tip housing 630. Seal 604 is configured to prevent the back-flow of gas provided to blade 518 via channel 573 of flexible conductive gas flow tube 570 into channel 583 of conduit 580.

As described above, outer tube 504, conduit 580, heat shrink 576, and tube 570 are each configured to be flexible to allow tip 506 to achieve a plurality of positions relative to handle 502 of apparatus 500. In one embodiment, outer tip housing 606 is configured to be grasped by a grasping tool, such as forceps 900. For example, as shown in FIGS. 14A, 14B, 14E, 14F, and 14G, tip housing 606 includes a pair of grasping slots 660 and 661. Grasping slots 660 and 661 are configured to receive engaging members of a grasping tool such as jaws 906 of forceps 900. In this way, grasping slots 660 and 661 enable tip 506 to be grasped by a grasping tool. Referring to FIGS. 11B and 14H, jaws 906 of forceps 900 are shown grasping slots 660 and 611 in accordance with the present disclosure. Once jaws 906 of grasping tool or forceps 900 securely grip slots 660 and 661 of tip 506, the forceps 900 may then be used to manipulate the position of tip 506 relative to housing 502 as the user desires.

It is to be appreciated that shaft 902 of forceps 900 may be configured as a rigid linear shaft or alternatively as multiple linked sections configured to be manipulated into different positions. In one embodiment, the shaft 902 may include one or more pivoting or rotational members 908 configured to allow jaws 906 to rotate tip 506 of apparatus 500 in a plurality of direction (e.g., rotational directions B, C, and D shown in FIG. 14H. In one embodiment, forceps 900 is controlled via control interface 904, where control interface 904 may be a manual control interface (e.g., including one or more controls for a human to manually control forceps 900) or a computer or robotic control interface (e.g., forceps 900 is computer operated).

In an exemplary embodiment, the grasping tool used to manipulate the orientation of tip 505 may be a robotic arm, such as, but not limited to, ProGrasp™ Forceps of the da Vinci® Surgical System made by Intuitive Surgical®, however other robotic arm systems may also be used with apparatus 500 to control tip 506.

It is to be appreciated that, in one embodiment, apparatus 500 and/or forceps 900 may be used with a trocar, such as trocar 370, described above. In this embodiment, a first trocar or canula and a second trocar or canula may each be disposed through a portion of a patient's body (e.g., through the abdomen of a patient) to provide access to a desired tissue site within the patient's body. The distal tip 506 and at least a portion of outer tube 504 are disposed through the first trocar and a portion of the grasping tool or forceps 900 (including jaws 906) is disposed through the second trocar, such that both the distal tip 506 of apparatus 500 and the jaws 906 of forceps 900 have access to the tissue site. Within the patient's body, slots 660, 661 of distal tip 506 receive jaws 906 and forceps 900 are used to control the distal tip 506 and perform a surgical procedure (e.g., mechanical cutting, electrosurgical cutting, ablation, coagulation, fulguration, application of a cold plasma beam, etc.) at the tissue site. In another embodiment, the distal tip 506 and at least a portion of outer tube 504 may be disposed in the same trocar or canula as the grasping tool or forceps 900.

In another embodiment, apparatus 500 may be used in open surgery.

Figure 15A:
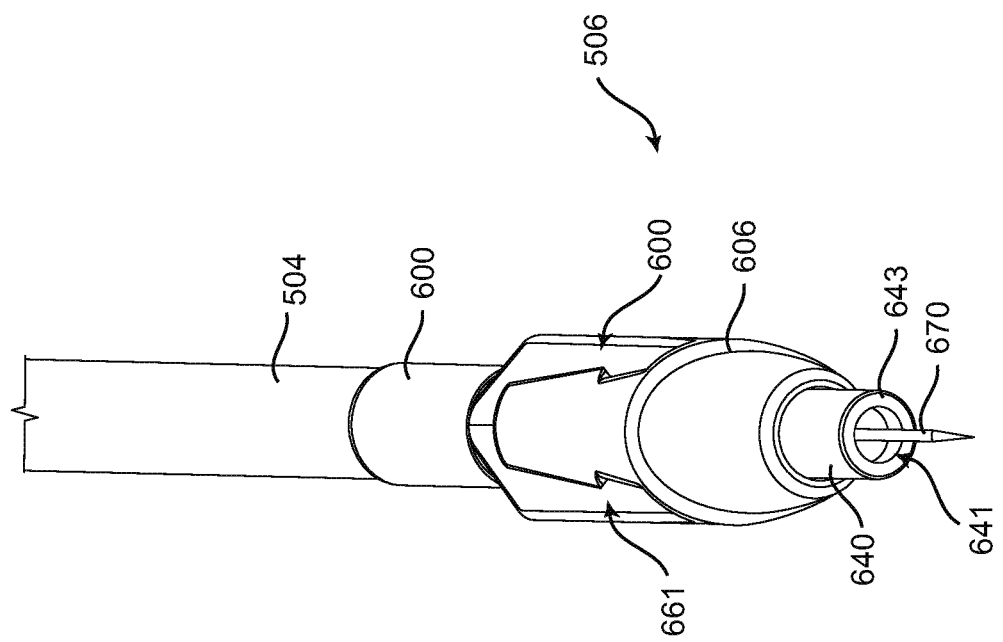
FIGS. 15A and 15B are partial perspective views of the distal portion of the electrosurgical apparatus of FIG. 11A including an electrosurgical needle in accordance with another embodiment of the present disclosure.
Figure 15B:
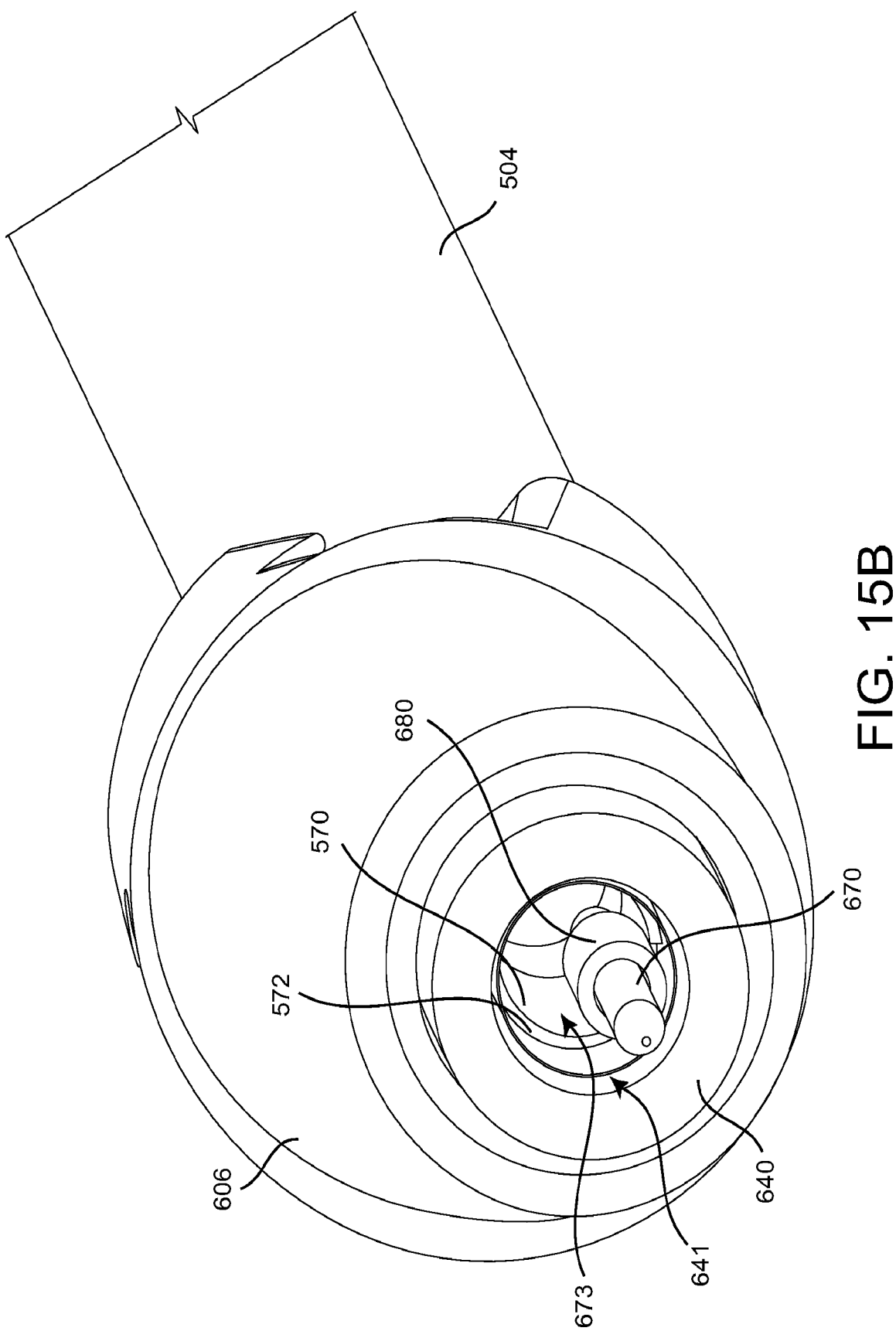

It is to be appreciated that in another embodiment of the present disclosure, electrode 518 of apparatus 500 may be configured as an electrosurgical needle instead of a planar electrosurgical blade. For example, referring to FIG. 15A, a partial perspective view of apparatus 500 is shown with an electrosurgical needle 670 disposed through ceramic tip 640 of tip 506. Referring to FIG. 15B, another partial perspective view of apparatus 500 is shown, where electrosurgical needle 670 is shown in more detail. As shown in FIG. 15B, needle 670 is fixedly coupled to distal end 572 of flexible conductive gas flow tube 570 via conductive tube or retaining member 680, where conductive tube 680 is disposed around needle 670. In the embodiment shown in FIG. 15B, distal end 643 of ceramic tip 640 does not include slots 651, 655 or gas passageways 652 and 653, but includes a single passageway 673. It is to be appreciated that when slider 516 is advanced in a distal direction toward end 521 of slot 522, conductive gas flow tube 570 is also advanced within outer tube 504 and gas flow tube conduit 580, thereby advancing needle 670 past the distal end of tip 506. Alternatively, when slider 516 is retracted in a proximal direction toward end 524 of slot 522, conductive gas flow tube 570 is also retracted, thereby retracting needle 670 into the interior of tip 506. Furthermore, it is to be appreciated that RF energy applied to conductive gas flow tube 570 is conducted to conductive tube 608 and to needle 670 to apply RF energy to a surgical site as described above.

Figure 16A:
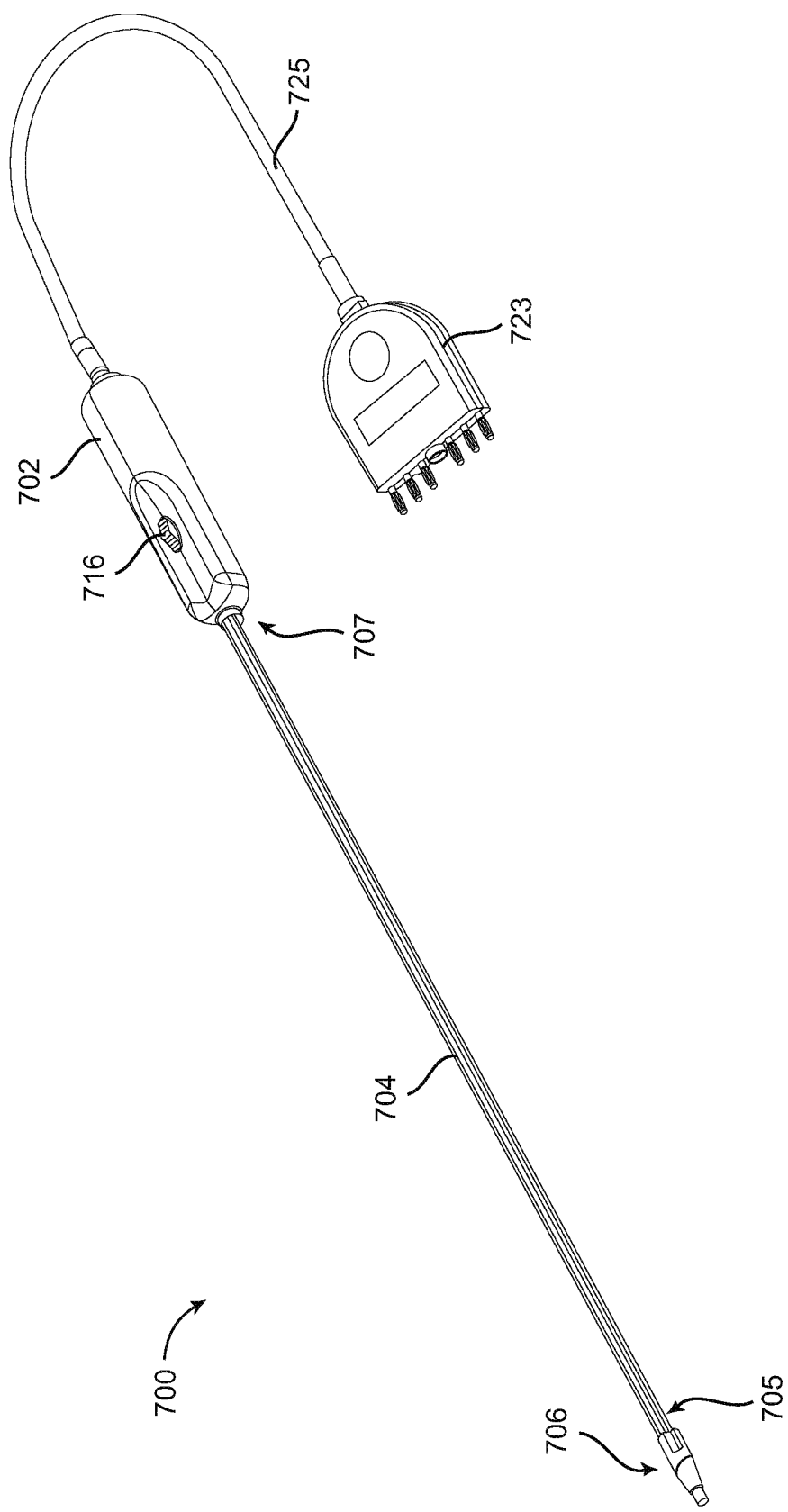
FIG. 16A is a perspective view of another electrosurgical apparatus in accordance with an embodiment of the present disclosure.

In another embodiment of the present disclosure, buttons 512 and 514 of apparatus 500 may be removed. For example, referring to FIG. 16A, apparatus 700 is shown in accordance with the present disclosure. Apparatus 700 includes tip 706, shaft or tube 704, housing 702, cable 725, and connector 723. Connector 723 is coupled to a housing 702 via a cable 725. Furthermore, a distal end 705 of shaft 704 is coupled to tip 706 and a proximal end 707 of shaft 704 is coupled to housing 702. A slider 716 is disposed on housing 702, where slider 716 functions in a manner similar to slider 516, i.e., slider 716 controls the advancement and retraction of an electrode (e.g., an electrosurgical blade or needle) disposed in a channel of tip 706. In one embodiment, apparatus 700 is coupled to an electrosurgical generator (not shown), where the electrosurgical generator is further coupled to one or more foot pedals or switches (such as foot switches 852, 854, described above) that, when pressed, are configured to perform the functions of buttons 512 and 514 described above (e.g., control the characteristics of the RF energy and/or gas provided to the electrode disposed in tip 706). It is to be appreciated that connected 723 may be coupled to an electrosurgical generator, such as ESU 12, and one or more gas supplies (not shown).

In one embodiment, shaft 704 may be configured as a multi-lumen shaft, where multi-lumen shaft 704 does not include a gas tube conduit, heat shrink, and gas flow tube, such as 580, 576, 570, which are included in apparatus 500. Referring to FIG. 16B, a perspective view of distal end 705 of multi-lumen shaft 704 is shown in accordance with the present disclosure. As shown in FIG. 16B, multi-lumen shaft 704 includes channels or lumens 708, 709, and 710. It is to be appreciated that, in one embodiment, multi-lumen shaft 704 is made of a flexible insulative or non-conductive material to allow tip 706 to achieve various positions.

Figure 16C:
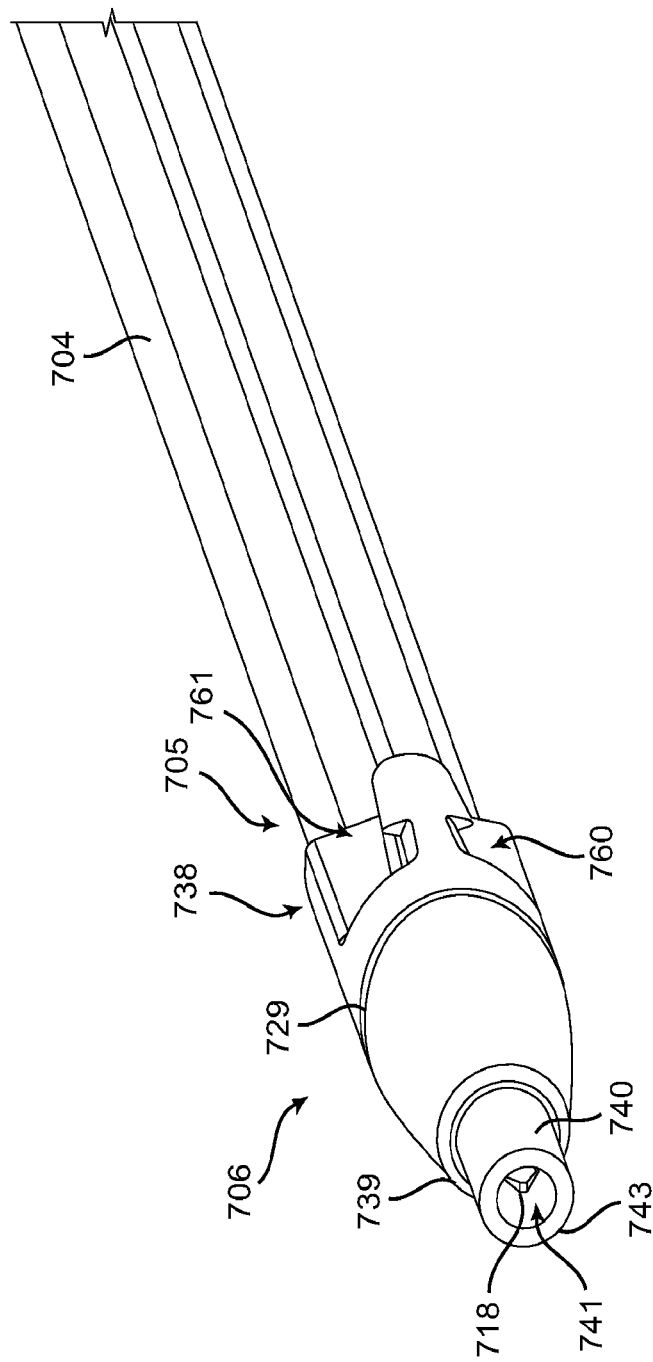
FIG. 16C is a partial perspective view of a distal portion of the electrosurgical apparatus of FIG. 16A in accordance with the present disclosure.

Referring to FIG. 16C, a partial perspective view of apparatus 700 is shown in accordance with the present disclosure. As shown in FIG. 16C, tip 706 includes a tip housing 729, where tip housing 729 has a distal end 739 and a proximal end 738. Proximal end 738 of tip housing 729 is coupled to distal end 705 of multi-lumen shaft 704. A ceramic tip 740 (similar to ceramic tip 640) is disposed in and coupled to the distal end 739 of a channel of tip housing 729, the channel extending from the distal end 739 of tip housing 729 to the proximal end 738 of tip housing 729. It is to be appreciated that, although not shown, distal end 705 of multi-lumen shaft 704 is disposed in the proximal end 738 of the channel within tip housing 729. The ceramic tip 740 includes a channel 741 extending from distal end 743 of ceramic tip 740 to a proximal end of ceramic tip 740 disposed within tip housing 729. An electrosurgical blade or needle 718 is disposed within channel 741 of ceramic tip 740. In one embodiment, tip housing 729 also includes griping slots 760 and 761 that are configured to be gripped by a gripping tool, such as forceps 900, to move tip 706 into various positions (as described above in relation to tip 706).

Referring again to FIG. 16B, in one embodiment, channel 710 of shaft 704 includes a flexible conductive rod 711. One end of flexible conductive rod 711 is coupled to slider 716 and the other end of the flexible conductive rod 711 is coupled to electrosurgical blade or needle 718. Similar to slider 516, slider 716 is configured such that when slider 716 is advanced toward shaft 704, rod 711 is advanced toward tip 706, thereby advancing electrosurgical blade or needle 718 past distal end 743 of channel 741 of ceramic tip 740. Furthermore, slider 516 is configured such that when slider 716 is retracted in a direction away from shaft 704, rod 711 is retracted within channel 711, thereby retracting electrosurgical blade or needle 718 into channel 741 (as shown in FIG. 16C).

It is to be appreciated that, although not shown, rod 711 is coupled to one or more wires of cable 725 within housing 702, such that electrosurgical energy can be applied to rod 711, thereby applying electrosurgical energy to electrosurgical blade or needle 718. In one embodiment, the proximal end of rod 711 is coupled to the one or more wires of cable 725 via slider 716, in similar manner as tube 570 is coupled to cable 562, as described above. Furthermore, although not shown rod 711 includes a plurality of laser cuts throughout rod 711 (similar to laser cuts 401) that enable rod 711 to be flexible.

Although not shown, in one embodiment, channel 710 is coupled to cable 725 within housing 702, such that an inert gas, such as helium or argon is provided via channel 710 to channel 741.

In another embodiment, rod 711 may be replaced by a flexible conductive gas flow tube and a heat shrink disposed around the flexible conductive gas flow tube, such as flexible conductive gas flow tube 570 and heat shrink 576. In this embodiment, flexible conductive gas flow tube 570 and heat shrink 576 are slidably disposed within channel 710 and the distal ends of tube 570 and heat shrink 576 are coupled to electrosurgical needle or blade 718 and the proximal ends of tube 570 of heat shrink 576 are coupled to slider 716. It is to be appreciated that, in this embodiment, tube 570 is coupled to blade 718 and slider 716 in a manner similar to that described above in relation to blade 518 and slider 516. In this embodiment, slider 716 controls the advancement and retraction of electrosurgical blade or needle 718. Furthermore, tube 570 is coupled to cable 725 within housing 702, such that, gas and RF energy may be provided to an electrosurgical blade or needle within tip 706.

Referring again to FIG. 16B, in another embodiment, each of channels 708 and 709 may be coupled to a gas supply to provide gas to tip 706. For example, in one embodiment, channels 708 and 709 are coupled to the same gas supply as channel 710. In another embodiment, channels 708 and 709 may be coupled to a gas supply that is different from the inert gas supply coupled to channel 710. For example, in one embodiment, channels 708 and 709 are coupled to an oxygen gas supply. In another embodiment, each of channels 708, 709, and 710 may be coupled to a different gas supply from each other. In another embodiment, a vacuum may be coupled to the proximal ends of one or more of channels 708, 709 to provide suction or aspiration to a surgical site. In one embodiment, cable 725 may include an aspiration tube coupled to a vacuum to provide the suction or aspiration.

Figure 16D:
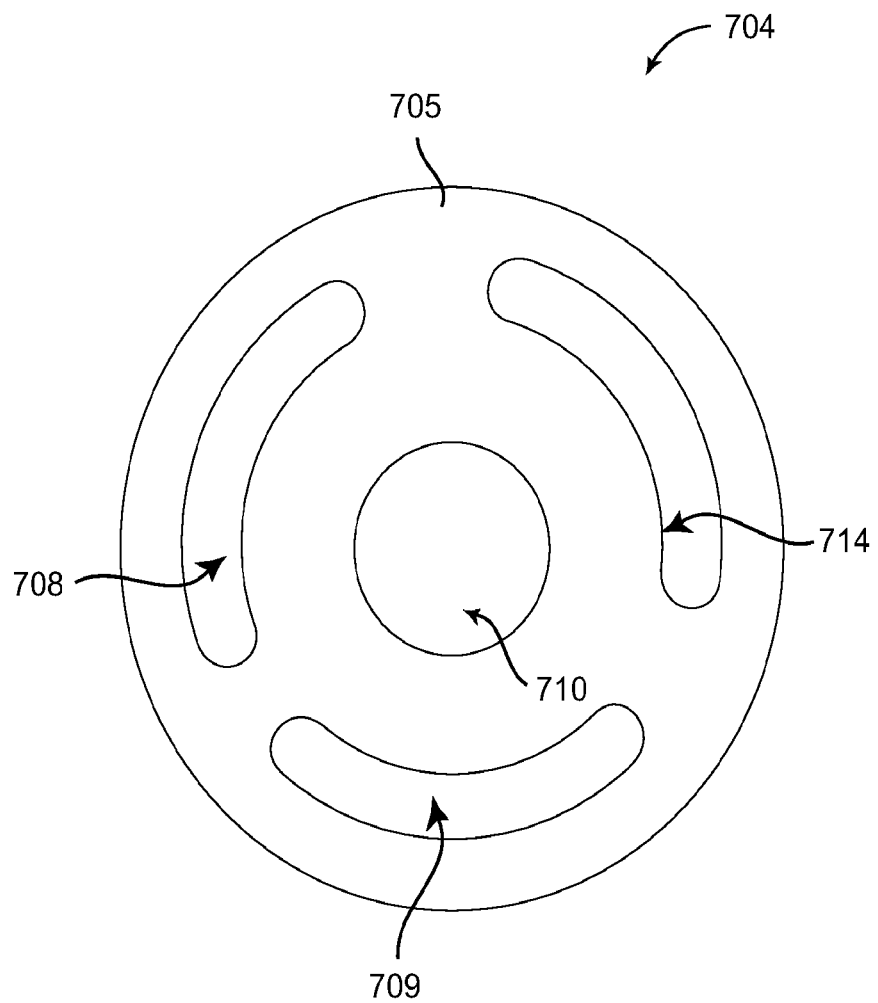
FIG. 16D is a front view of a distal end of the multi-lumen shaft of the electrosurgical apparatus of FIG. 16A in accordance with another embodiment of the present disclosure.

It is to be appreciated, in another embodiment, multi-lumen shaft 704 may include more than three channels. For example, referring to FIG. 16D, a front view of the distal end 705 of multi-lumen shaft 704 is shown, where multi-lumen shaft 704 includes a fourth channel 714. The fourth channel 714 may be coupled to the same gas supply as channels 708 and 709 or to a different gas supply.

Although in the embodiments described above, electrodes 518, 718 of apparatuses 500, 700 are slidable distally and proximally with respect to distal tips 506, 706, in other embodiments, electrodes 518, 718 may be configured to be fixed with respect to distal tips 506, 706. In this embodiment, flexible conductive tube 570 and flexible conductive rod 711 are immovable or fixed in relation to outer tubes 504, 704. In various embodiments, the position of electrodes 518, 718 may be fixed in a fully extended, partially extended, or a fully retracted position to support various electrosurgical procedures. For example, in one embodiment, electrodes 518, 718 are fixed with respect to distal tips 506, 706 in a retracted or substantially retracted position. In this embodiment, apparatuses 500, 700 are configured for ablation but not mechanical cutting.

In another embodiment, outer tubes 504 and/or 704 may be configured as rigid linear shafts (i.e., tubes 504, 704 are not flexible), where conduit 580, tube 570, and rod 711 may also be configured to be rigid and linear without tubes 504, 704. In this embodiment, apparatuses 500, 700 are configured for use without a grasping tool, such as forceps 900.

It is to be appreciated that the various features shown and described are interchangeable, that is, a feature shown in one embodiment may be incorporated into another embodiment.

For example, with either the electrode, e.g., a blade, needle, etc., extended or retracted, various additional electrosurgical plasma beam effects can be achieved by modifying the applied high voltage and high frequency waveform provided to the electrodes of apparatuses 100, 200, 300, 500, 700 via an ESU, such as, ESU 12. In addition to the generation of cold plasma, these effects include several forms of monopolar coagulation and gas assisted coagulation, also known as Cool Coag effects. It is to be appreciated that in one of these gas assisted coagulation modes, a coagulation waveform is applied to the electrode while an inert gas is present, e.g., Helium, thereby forming a plasma. In this coagulation mode, the plasma beam is applied to the target tissue to perform coagulation. In another coagulation mode, coagulation is performed by applying a monopolar coagulation waveform to the electrode of the electrosurgical apparatus and contacting the target tissue with the electrosurgical apparatus. While the electrode is contacting the target tissue, an inert gas, such as helium or argon is provided to the target tissue to provide a cooling effect (i.e., to decrease the temperature of the target tissue). Cool Coag™ combines the power of a monopolar coagulation waveform with the cooling flow of an inert gas, such as Helium, although other gases may be used such as Argon. In this manner, a single electrosurgical apparatus, such as apparatuses 100, 200, 300, 500, 700, in accordance with the present disclosure, may generate 1.) cold plasma discharges, 2.) monopolar coagulation effects and 3.) various gas assisted coagulation discharges, or plasma.

It is to be appreciated that in various embodiments two high voltage step up output transformers disposed in the ESU coupled to apparatuses 100, 200, 300, 500, 700 are utilized to generate the necessary waveforms. An exemplary system including embodiments two high voltage step up output transformers are shown and described in commonly owned U.S. Pat. No. 9,144,453 to Rencher, et al., the contents of which are hereby incorporated by reference. One transformer is optimized for high voltage and low current and is utilized in generating the cold plasma beam with the blade retracted, such with blades 118, 218, 318, 518, 718 of electrosurgical apparatuses 100, 200, 300, 500, 700, respectively, described above. The other transformer is optimized for somewhat lower voltage but higher current required by electrosurgical procedures such as monopolar, bipolar, and coagulation. To affect the various operational modes described herein, both of these transformers may be disposed in the generator power supply unit or ESU for the electrosurgical apparatus being used. Buttons on a hand held applicator, such as buttons 512, 514 of electrosurgical apparatus 500, or selection of an appropriate foot switch, such as foot switches 852, 854, may be configured to control which transformer is activated for the required procedure to generate the appropriate waveform.

Figure 17A:
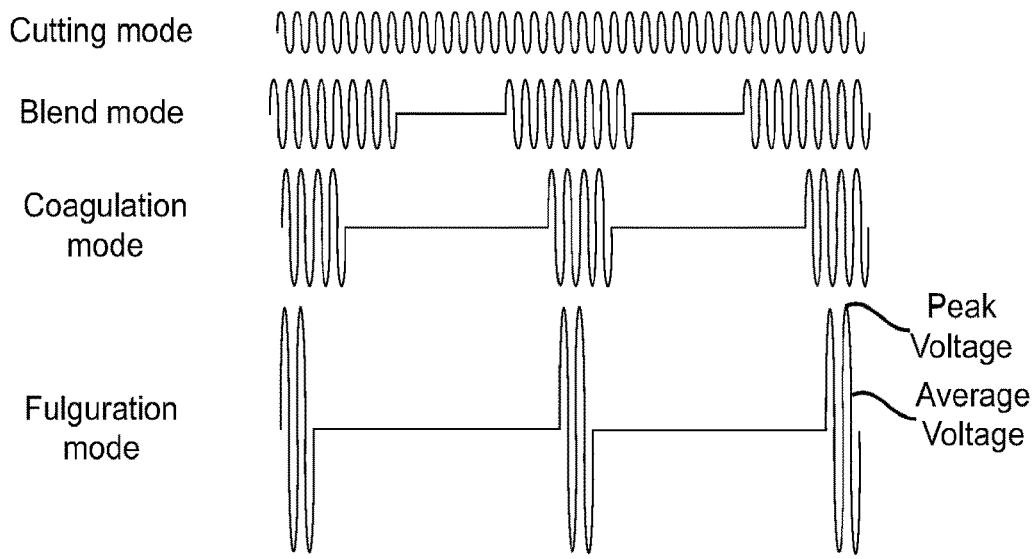
FIG. 17A illustrates various waveforms to be applied to an electrosurgical apparatus in accordance with the present disclosure.

In the monopolar coagulation mode, (e.g., activated by pressing button 514 of electrosurgical apparatus 500 or an appropriate foot switch 852, 854, as described above), a coagulation waveform is applied to the electrode and coagulation effects may be applied to target tissue by making contact between the electrode of the electrosurgical device and the target tissue. Some examples of typical coagulation waveforms are illustrated in FIG. 17A. In this mode, while an inert gas is present, e.g., Helium, the inert gas does not generate a plasma but provides a cooling effect to the target tissue.

In the plasma coagulation mode, (e.g., activated by pressing button 514 of electrosurgical apparatus 500 or an appropriate foot switch 852, 854, as described above) several forms of gas assisted coagulation (or plasma coagulation) can be affected by spacing the tip of the electrode a distance away from the target tissue, including a pinpoint coagulation mode, a gentle coagulation mode, and a spray coagulation mode. A high crest factor, or ratio of peak voltage to RMS voltage, assures ignition of the flowing inert gas in the various gas assisted coagulation modes. In one embodiment, the coagulation mode to be employed during plasma coagulation (e.g., when button 514 or an appropriate foot switch 852, 854 is pressed) is selected at an electrosurgical generator or ESU that is providing electrosurgical energy to the apparatus. Some examples of typical coagulation waveforms are illustrated in FIG. 17A. In this way, after a coagulation mode is selected at the generator (e.g., pinpoint, gentle, or spray coagulation mode), when the coagulation button (e.g., button 514) or appropriate foot switch 852, 854 of the electrosurgical apparatus (e.g., apparatus 500) is activated, the selected coagulation mode is employed in the plasma beam emitted by the electrosurgical apparatus.

In the pinpoint and gentle gas assisted coagulation modes, a relatively short period exists between the plasma generating pulse groups. Residual ions from the previous discharge path ensure that subsequent discharges follow the same path, providing a plasma beam with the same pointing accuracy as the cold plasma beam, but with substantially higher current and enhanced coagulation capability.

Figure 18:
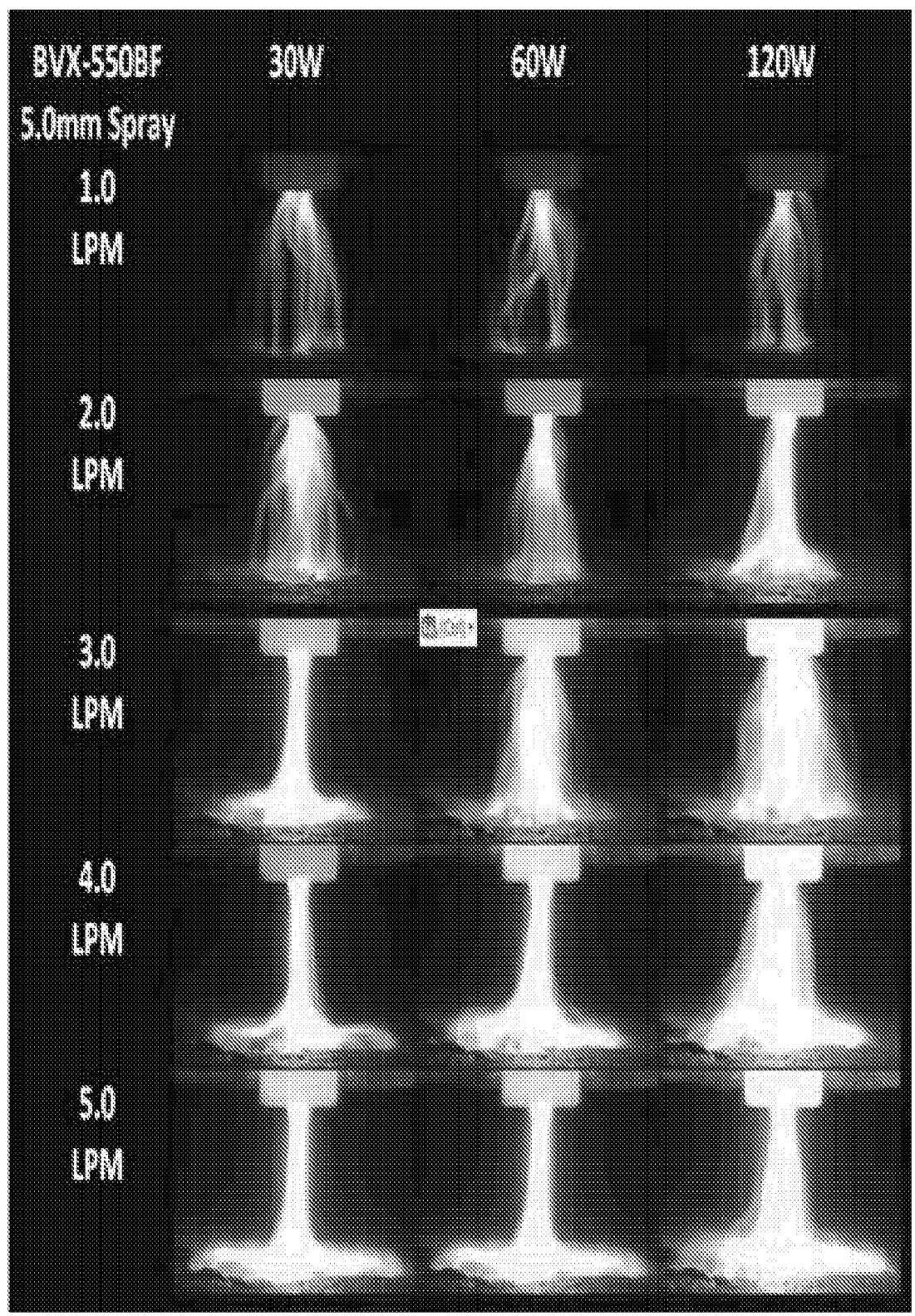
FIG. 18 illustrates various discharge beams produced during a gas assisted spray coagulation mode of an electrosurgical apparatus in accordance with the present disclosure for various power settings and gas flow rates.

The gas assisted spray mode, by contrast, has a much longer period between pulses (e.g., by applying the fulguration mode waveform shown in FIG. 17A to the electrode), permitting any residual ions to recombine. There is, therefore, no preferential residual discharge path and the individual discharges randomly cover a much larger area. Examples of discharges generated during the gas assisted spray coagulation mode are shown in FIG. 18 for various power settings and gas flow rates, where the power settings are indicated along the upper x-axis and the gas flow rates are indicated along the left y-axis. It is to be appreciated that the discharges shown were generated at a fixed distance from a target surface of about 5.0 mm.

Figure 17B:
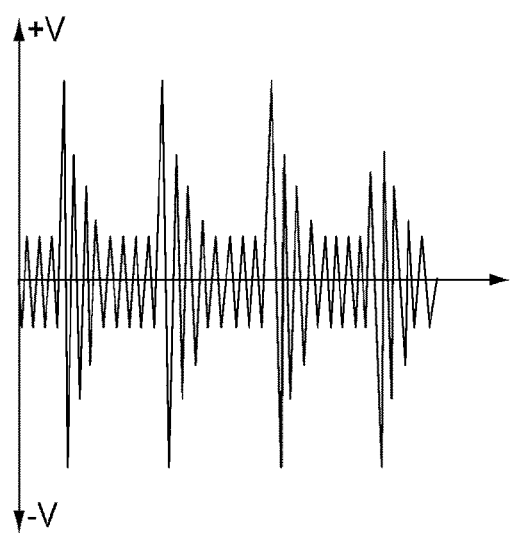
FIG. 17B illustrates another waveform to be applied to an electrosurgical apparatus in accordance with the present disclosure.

FIG. 17B shows a waveform employed during the cold plasma beam mode or J-plasma mode of the electrosurgical apparatus. When the electrosurgical apparatus is in J-plasma mode (as selected via buttons 512, 514 and/or footswitches 852, 854), the waveform shown in FIG. 17B is applied to the electrode of the electrosurgical apparatus and cold plasma or J-plasma is generated when an inert gas such as Helium flows over the distal tip of the electrode.

As in the cold plasma beam mode, a wide range of physiological effects can be affected in the various gas assisted coagulation modes by adjusting the ratio of electrical power in the beam and the inert gas flow rate.

From the above, it is to be appreciated that a single electrosurgical apparatus in accordance with the present disclosure may include at least three activation modes including a cold plasma mode, a monopolar coagulation mode (where an electrode of the electrosurgical apparatus is touching target tissue) and a gas assisted or plasma coagulation mode (where an electrode of the electrosurgical apparatus is space apart from the target tissue without touching the tissue). It is to be appreciated that the parameters for execution of each of the modes described above may be stored in a memory and executed by a processor of the ESU coupled to the electrosurgical apparatus.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
a housing including a proximal end and a distal end;
a flexible insulating outer tube including a proximal end and a distal end, the proximal end of the flexible insulating outer tube coupled to the distal end of the housing;
a distal tip including a proximal end and a distal end, the proximal end of the distal tip coupled to the distal end of the flexible insulating outer tube, the distal tip including an electrode;
a flexible electrically conducting tube disposed through the flexible insulating outer tube and including a proximal end and a distal end, the distal end of the flexible electrically conducting tube coupled to the electrode and configured to provide electrosurgical energy thereto and to provide inert gas to the distal tip;
wherein the flexible insulating outer tube and the flexible electrically conducting tube are configured to enable the distal tip to achieve a plurality of positions relative to the housing; and
a slider member slidably coupled to the housing, a first portion of the slider member being disposed in an interior of the housing and coupled to the proximal end of the flexible electrically conducting tube for moving the flexible electrically conducting tube relative to the housing and the outer tube thereby extending and retracting the electrode, the first portion of the slider member includes a first channel having a first side and a second side, the first side coupled to the proximal end of the flexible electrically conducting tube and the second side configured to receive the inert gas such that the inert gas is provided to the flexible electrically conducting tube via the first channel, the first portion of the slider member further including aa second channel that merges with a portion of the first channel, and a conducting wire disposed through the second channel and coupled to the proximal end of the flexible electrically conducting tube provides electrosurgical energy to the flexible electrically conducting tube.

2. The electrosurgical apparatus of claim 1, wherein the distal tip is configured to be grasped by a grasping tool to manipulate the position of the distal tip relative to the housing.

3. The electrosurgical apparatus of claim 2, wherein the distal tip includes a first grasping slot and a second grasping slot, the first and second grasping slots configured to enable the grasping tool to grasp the distal tip.

4. The electrosurgical apparatus of claim 1, wherein the electrode is configured as an electrically conducting needle.

5. The electrosurgical apparatus of claim 1, wherein in a first position of the flexible electrically conducting tube, the electrode extends beyond the distal end of the distal tip for mechanical cutting, and, in a second position of the flexible electrically conducting tube, the electrode is retracted within the distal tip and is energized via the flexible electrically conducting tube to form plasma when the inert gas is provided to the distal tip.

6. The electrosurgical apparatus of claim 5, wherein the electrode is configured as an electrically conducting blade.

7. The electrosurgical apparatus of claim 6, further comprising a generally cylindrical ceramic insert coupled to the distal end of the distal tip, the electrically conducting blade slidably coupled to an inner circumference of the ceramic insert.

8. The electrosurgical apparatus of claim 7, wherein the ceramic insert includes at least one slot disposed on the inner circumference of the ceramic insert for slidably receiving at least a portion of the electrically conducting blade and the ceramic insert is fixedly coupled to the distal tip, such that the ceramic insert and the electrically conducting blade are fixed rotationally with respect to the distal tip.

9. The electrosurgical apparatus of claim 1, wherein the flexible electrically conducting tube includes a plurality of cuts to enable the flexible electrically conducting tube to be flexible.

10. The electrosurgical apparatus of claim 9, further comprising heat shrink material disposed over the flexible electrically conducting tube to prevent gas leakage from the flexible electrically conducting tube.

11. The electrosurgical apparatus of claim 1, wherein the proximal end of the flexible electrically conducting tube is rotatably coupled to the first side of the first portion of the slider member such that the flexible electrically conducting tube is rotatable relative to the slider member.

12. The electrosurgical apparatus of claim 1, further comprising a flexible wire including a proximal end and a distal end, the flexible wire disposed through the flexible insulating outer tube, the proximal end of the flexible wire coupled to an interior of the housing and the distal end of the flexible wire coupled to the distal tip, the flexible wire configured to provide structural integrity to the flexible insulating outer tube when a force is applied to the distal tip in a direction that would cause stretching of the flexible insulating outer tube.

13. The electrosurgical apparatus of claim 1, further comprising a rigid tube including a proximal end and a distal end, the distal end of the rigid tube fixedly coupled to the proximal end of the flexible insulating outer tube and the proximal end of the rigid tube rotatably coupled to the distal end of the housing such that the flexible insulating outer tube and the rigid tube are rotatable relative to the housing, wherein the proximal end of the flexible electrically conducting tube is disposed through the rigid tube and extends into the interior of the housing.

14. The electrosurgical apparatus of claim 1, further comprising at least one foot switch for controlling a waveform applied to the electrode.

15. The electrosurgical apparatus of claim 1, wherein the electrode is fixedly coupled to the distal tip.

16. An electrosurgical apparatus comprising:
a housing including a proximal end and a distal end;
a flexible insulating outer tube including a proximal end and a distal end, the proximal end of the flexible insulating outer tube coupled to the distal end of the housing;
a distal tip including a proximal end and a distal end, the proximal end of the distal tip coupled to the distal end of the flexible insulating outer tube, the distal tip including an electrode;
a flexible electrically conducting member disposed through the flexible insulating outer tube and including a proximal end and a distal end, the distal end of the flexible electrically conducting member coupled to the electrode and configured to provide electrosurgical energy thereto; and
a generally cylindrical ceramic insert fixedly coupled to the distal end of the distal tip, the ceramic insert including at least one slot disposed on the inner circumference of the ceramic insert for slidably receiving at least a portion of the electrode, such that the ceramic insert and the electrode are fixed rotationally with respect to the distal tip,
wherein the flexible insulating outer tube and the flexible electrically conducting member are configured to enable the distal tip to achieve a plurality of positions relative to the housing and the flexible electrically conducting member is movable relative to the housing and the flexible insulating outer tube to extend and retract the electrode relative to the distal tip;
wherein the electrode is an electrically conducting blade and the at least one slot of the ceramic insert includes diametrically opposed slots disposed on the inner circumference of the ceramic insert configured to slidably receive portions of the electrically conducting blade.

* * * * *